United States Patent
Townes et al.

(10) Patent No.: US 11,643,668 B2
(45) Date of Patent: May 9, 2023

(54) CRISPR/CAS9 COMPLEX FOR GENOMIC EDITING

(71) Applicant: THE UAB RESEARCH FOUNDATION, Birmingham, AL (US)

(72) Inventors: Tim Townes, Birmingham, AL (US); Lei Ding, Vestavia, AL (US); Chia-Wei Chang, San Diego, CA (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 503 days.

(21) Appl. No.: 15/737,132

(22) PCT Filed: Jun. 17, 2016

(86) PCT No.: PCT/US2016/038161
§ 371 (c)(1),
(2) Date: Dec. 15, 2017

(87) PCT Pub. No.: WO2016/205703
PCT Pub. Date: Dec. 22, 2016

(65) Prior Publication Data
US 2019/0144888 A1    May 16, 2019

Related U.S. Application Data

(60) Provisional application No. 62/266,316, filed on Dec. 11, 2015, provisional application No. 62/181,138, filed on Jun. 17, 2015.

(51) Int. Cl.
| | |
|---|---|
| *C12N 15/90* | (2006.01) |
| *C12N 15/11* | (2006.01) |
| *C12N 9/22* | (2006.01) |
| *A61K 35/28* | (2015.01) |
| *A61P 7/00* | (2006.01) |
| *C12N 15/00* | (2006.01) |
| *A61K 48/00* | (2006.01) |
| *C12Q 1/6883* | (2018.01) |
| *C12N 15/10* | (2006.01) |
| *C12N 5/0789* | (2010.01) |

(52) U.S. Cl.
CPC ............ *C12N 15/907* (2013.01); *A61K 35/28* (2013.01); *A61K 48/00* (2013.01); *A61K 48/005* (2013.01); *A61P 7/00* (2018.01); *C12N 5/0647* (2013.01); *C12N 9/22* (2013.01); *C12N 15/00* (2013.01); *C12N 15/102* (2013.01); *C12N 15/11* (2013.01); *C12N 15/111* (2013.01); *C12N 15/90* (2013.01); *C12Q 1/6883* (2013.01); *C07K 2319/10* (2013.01); *C07K 2319/60* (2013.01); *C12N 2310/20* (2017.05); *C12N 2510/00* (2013.01); *C12N 2800/80* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,526,784 B2 | 12/2016 | Liu et al. |
| 9,737,604 B2 * | 8/2017 | Liu ................. A61K 38/465 |
| 9,822,370 B2 | 11/2017 | Musunuru et al. |
| 10,208,319 B2 | 2/2019 | Musunuru et al. |
| 10,266,850 B2 | 4/2019 | Doudna et al. |
| 2012/0100569 A1 | 4/2012 | Liu et al. |
| 2014/0120622 A1 | 5/2014 | Gregory et al. |
| 2015/0071889 A1 | 3/2015 | Musunuru et al. |
| 2015/0071903 A1 | 3/2015 | Liu et al. |
| 2016/0009813 A1 | 1/2016 | Themeli |
| 2017/0349914 A1 | 12/2017 | Cox |
| 2018/0141992 A1 | 5/2018 | Cowan et al. |

FOREIGN PATENT DOCUMENTS

| | | |
|---|---|---|
| CN | 104894068 A | 9/2015 |
| EP | 2836226 | 10/2017 |
| WO | 2014/059173 A2 | 4/2014 |
| WO | 2014/191128 A1 | 12/2014 |
| WO | 2014191128 | 12/2014 |
| WO | 2015/006498 A2 | 1/2015 |
| WO | 2015/035136 A2 | 3/2015 |
| WO | 2016/123578 A1 | 8/2016 |
| WO | 2016/160721 A1 | 10/2016 |

(Continued)

OTHER PUBLICATIONS

Sun et al., Mol. BioSyst., 2012, 8, 1255-1263 (Year: 2012).*

(Continued)

*Primary Examiner* — James D Schultz
(74) *Attorney, Agent, or Firm* — Kilpatrick Townsend & Stockton LLP

(57) ABSTRACT

Provided herein are CRISPR/Cas9 complexes and method of using same.

15 Claims, 29 Drawing Sheets
Specification includes a Sequence Listing.

(56) References Cited

FOREIGN PATENT DOCUMENTS

| WO | 2016205680 | 12/2016 |
|---|---|---|
| WO | 2017180989 | 10/2017 |

OTHER PUBLICATIONS

Perez et al. Nat Biotechnol, 2008, 26(7)808-816 (Year: 2008).*
Ramakrishna et al. Genome Research 2014, 24:1020-1027 (Year: 2014).*
Japanese Patent Application No. 2017-565277, "Office Action" dated Jul. 15, 2020, 17 pages with English translation.
Cronican, et al., "Potent Delivery of Functional Proteins into Mammalian Cells in Vitro and In Vivo Using a Supercharged Protein", ACS Chemical Biology, vol. 5, No. 8, 2010, pp. 747-752.
Nouri F.S., et al., "A Recombinant Biopolymeric Platform for Reliable Evaluation of the Activity of pH-Responsive Amphiphile Fusogenic Peptides", Biomacromolecules, vol. 14, 2013, pp. 2033-2040.
Hale M. et al., High-Efficiency Targeted Introduction of an Anti-CDI9-CAR Into the CCR5 Locus in Primary Human T Cells., Molecular Therapy, vol. 23 Supplement 1 (May 2015), p. S113, 284.
Themeli M. et al., Cell Stem Cell, vol. 16 Issue 4 (Apr. 2015), p. 357-366.
Torikai H. et al., Blood, vol. 119 No. 24 (2012), p. 5697-570.
Aiuti et al., Gene Therapy for Immunodeficiency Due to Adenosine Deaminase Deficiency, The New England Journal of Medicine, vol. 360, No. 5, Jan. 29, 2009, pp. 447-458.
Aluigi et al., Nucleofection is an Efficient Nonviral Transfection Technique for Human Bone Marrow-Derived Mesenchymal Stem Cells, Stem Cells, vol. 24, No. 2, Feb. 2006, pp. 454-461.
Bialk et al., Regulation of Gene Editing Activity Directed by Single-Stranded Oligonucleotides and CRISPR/Cas9 Systems, Plos One, vol. 10, No. 6, Jun. 8, 2015, pp. 1-19.
Biffi et al., Lentiviral Hematopoietic Stem Cell Gene Therapy Benefits Metachromatic Leukodystrophy, Science, vol. 341, No. 6148, Aug. 23, 2015, pp. 1233158-1-1233158-11.
Caignard et al., Mouse ENU Mutagenesis to Understand Immunity to Infection Methods, Selected Examples, and Perspectives, Genes, vol. 5, No. 4, Dec. 2014, pp. 887-925.
Chang et al., Broad T-Cell Receptor Repertoire in T-Lymphocytes Derived from Human Induced Pluripotent Stem Cells, PLoS One, vol. 9, No. 5, May 14, 2014, pp. 1-10.
Chang et al., Polycistronic Lentiviral Vector for "Hit and Run" Reprogramming of Adult Skin Fibroblasts to Induced Pluripotent Stem Cells, Stem Cells, vol. 27, May 2009, pp. 1042-1049.
Cong et al., Multiplex Genome Engineering Using CRISPR/Cas Systems, Science, vol. 339, No. 6121, Feb. 15, 2013, pp. 819-823.
Davydov et al., Identifying a High Fraction of the Human Genome to be under Selective Constraint Using GERP++, PLoS Computational Biology, vol. 6, No. 12, Dec. 2010, 13 pages.
De Pooter et al., T-cell Potential and Development in Vitro: The OP9-DL1 Approach, Current Opinion in Immunology, vol. 19, No. 2, Apr. 2007, pp. 163-168.
Dervovic et al., Comparative and Functional Evaluation of in Vitro Generated to Ex Vivo CD8 T Cells, Journal of Immunology, vol. 189, No. 7, Oct. 1, 2012, pp. 3411-3420.
European Application No. 16812552.4, Extended European Search Report dated Dec. 5, 2018, 8 pages.
European Application No. 16812552.4, Office Action dated Jan. 3, 2020, 5 pages.
Eynon et al., Distinct Effects of Jak3 Signaling on $\alpha\beta$ and $\gamma\delta$ Thymocyte Development, Journal of Immunology, vol. 162, No. 3, Feb. 1, 1999, pp. 1448-1459.
Ferrua et al., Update on Gene Therapy for Adenosine Deaminase-Deficient Severe Combined Immunodeficiency, Current Opinion in Allergy and Clinical Immunology, vol. 10, 2010, pp. 551-556.
Forbes et al., The Catalogue of Somatic Mutations in Cancer (COSMIC), Current Protocols in Human Genetics, Apr. 2008, 32 pages.

Fu et al., High-frequency Off-Target Mutagenesis Induced by CRISPR-Cas Nucleases in Human Cells, Nature Biotechnology, vol. 31, No. 9, Sep. 2013, pp. 822-826.
Girl et al., Utilization of the $\beta$ and $\gamma$ Chains of the IL-2 Receptor by the Novel Cytokine IL-15, The EMBO Journal, vol. 13, No. 12, Jun. 15, 1994, pp. 2822-2830.
Hacein-Bey-Abina et al., A Modified $\gamma$-Retrovirus Vector for X-Linked Severe Combined Immunodeficiency, The New England journal of medicine, vol. 371, No. 15, Oct. 9, 2014, pp. 1407-1417.
Hacein-Bey-Abina et al., Insertional Oncogenesis in 4 Patients after Retrovirus-mediated Gene Therapy of SCID-X1, The Journal of Clinical Investigation, vol. 118, No. 9, Sep. 2, 2008, pp. 3132-3142.
Hacein-Bey-Abina et al., LMO2-Associated Clonal T Cell Proliferation in Two Patients after Gene Therapy for SCID-X1, Science, vol. 302, No. 5644, Oct. 24, 2003, pp. 415-419.
Hanna et al., Treatment of Sickle Cell Anemia Mouse Model with iPS Cells Generated from Autologous Skin, Science, vol. 318, No. 5858, Dec. 21, 2007, pp. 1920-1923.
Hare et al., An Essential Role for the II-7 Receptor During Intrathymic Expansion of the Positively Selected Neonatal T Cell Repertoire, Journal of Immunology, vol. 165, No. 5, Sep. 1, 2000, pp. 2410-2414.
Kang et al., Defective Development of $\gamma/\delta$ T Cells in Interleukin 7 Receptor-Deficient Mice is Due to Impaired Expression of T Cell Receptor $\gamma$ Genes, Journal of Experimental Medicine, vol. 190, No. 7, Oct. 4, 1999, pp. 973-982.
Kondo et al., Bcl-2 Rescues T Lymphopoiesis, but Not B or NK Cell Development, in Common $\gamma$ Chain-Deficient Mice, Immunity, vol. 7, Jul. 1, 1997, pp. 155-162.
Landrum et al., ClinVar: Public Archive of Relationships Among Sequence Variation and Human Phenotype, Nucleic Acids Research, vol. 42, No. D1, Jan. 1, 2014, pp. D980-D985.
Lenz et al., Nucleoporation of Dendritic Cells: Efficient Gene Transfer by Electroporation Into Human Monocyte-Derived Dendritic Cells, FEBS Letters, vol. 538, Nos. 1-3, Mar. 13, 2003, pp. 149-154.
Li et al., Fast and Accurate Long-Read Alignment with Burrows-Wheeler transform, Bioinformatics, vol. 26, No. 5, Mar. 1, 2010, pp. 589-595.
Li et al, Interleukin-7 Inactivates the Pro-Apoptotic Protein Bad Promoting T Cell Survival, The Journal of biological chemistry, vol. 279, No. 28, Jul. 9, 2004, pp. 29160-29166.
Lin et al., Enhanced Homology-Directed Human Genome Engineering by Controlled Timing of CRISPR/Cas9 Delivery, Elife, vol. 3, No. e04766, Dec. 15, 2014, pp. 1-13.
Maasho et al., Efficient Gene Transfer Into the Human Natural Killer Cell Line, NKL, Using the Amaxa Nucleofection System, Journal of Immunological Methods, vol. 284, No. 1-2, 2004, pp. 133-140.
Makarova et al., Evolution and Cassification of the CRISPR-Cas Sytems, Nature Reviews Microbiology, vol. 9, No. 6, Jun. 2011, pp. 467-477.
Mali et al., RNA-Guided Human Genome Engineering Via Cas9, Science, vol. 339, No. 6121, Feb. 15, 2013, pp. 823-826.
McKenna et al., The Genome Analysis Toolkit: a Mapreduce Framework for Analyzing Next-generation DNA Sequencing Data, Genome Research, vol. 20, No. 9, Sep. 2010, pp. 1297-1303.
McNaughton et al., Mammalian Cell Penetration, siRNA Transfection, and DNA Transfection by Supercharged Proteins, Proceedings of the National Academy of Sciences of the United States of America, vol. 106, No. 15, Apr. 14, 2009, pp. 6111-6116.
Nosaka et al., Defective Lymphoid Development in Mice Lacking Jak3, Science, vol. 270, 1995, pp. 800-802.
Notarangelo et al., Mutations in Severe Combined Immune Deficiency (SCID) Due to JAK3 Deficiency, Human Mutation, vol. 18, No. 4, Oct. 2001, pp. 255-263.
Ohnuki et al., Generation and Characterization of Human Induced Pluripotent Stem Cells, Current Protocols in Stem Cell Biology, Chapter 4: Unit 4A.2, Jun. 2009.
Pai et al., Transplantation Outcomes for Severe Combined Immunodeficiency, 2000-2009, The New England Journal of Medicine, vol. 371, Jul. 31, 2014, pp. 434-446.
Park et al., Signaling by Intrathymic Cytokines, Not T Cell Antigen Receptors, Specifies CD8 Lineage Choice and Promotes the Dif-

(56) References Cited

OTHER PUBLICATIONS ferentiation of Cytotoxic-Lineage T Cells, Nature Immunology, vol. 11, No. 3, Mar. 2010, pp. 257-264.
International Application No. PCT/US2016/038161, International Preliminary Report on Patentability dated Dec. 28, 2017, 7 pages.
International Application No. PCT/US2016/038161, International Search Report and Written Opinion dated Oct. 27, 2016, 11 pages.
Quinlan et al., BEDTools: A Flexible Suite of Utilities for Comparing Genomic Features, Bioinformatics, vol. 26, No. 6, Mar. 15, 2010, pp. 841-842.
Rice et al., EMBOSS: The European Molecular Biology Open Software Suite, Trends in Genetics, vol. 16, No. 6, Jun. 2000, pp. 276-277.
Rothenberg et al., Launching the T-cell-lineage Developmental Programme, Nature Reviews Immunology, vol. 8, No. 1, Jan. 2008, pp. 9-21.
Russell et al., Mutation of Jak3 in a Patient with SCID: Essential Role of Jak3 in Lymphoid Development, Science, vol. 270, No. 5237, Nov. 3, 1995, pp. 797-800.
Sauer et al., Progress in Gene Therapy for Primary Immunodeficiencies Using Lentiviral Vectors, Current Opinion in Allergy and Clinical Immunology, vol. 14, Dec. 2014, pp. 527-534.
Schmitt et al., Induction of T Cell Development and Establishment of T Cell Competence from Embryonic Stem Cells Differentiated in Vitro, Nature Immunology, vol. 5, No. 4, Apr. 2004, pp. 410-417.
Schmitt et al., Induction of T Cell Development from Hematopoietic Progenitor Cells by delta-like-1 in Vitro, Immunity, vol. 17, No. 6, Dec. 2002, pp. 749-756.
South African Application No. 2018/00026, Notice of Allowance dated Feb. 20, 2019, 1 page.
Smith et al., Whole-Genome Sequencing Analysis Reveals High Specificity of CRISPR/Cas9 and TALEN-Based Genome Editing in Human iPSCs, Cell Stem Cell, vol. 15, No. 1, Jul. 3, 2014, pp. 12-13.
Takahashi et al., Efficient Introduction of a Gene into Hematopoietic Cells in S-phase by Electroporation, Experimental Hematology, vol. 19, No. 5, Jun. 1991, Abstract.
Takahashi et al., Induction of Pluripotent Stem Cells from Adult Human Fibroblasts by Defined Factors, Cell, vol. 131, No. 5, Nov. 30, 2007, pp. 861-872.
Takahashi et al., Induction of Pluripotent Stem Cells from Mouse Embryonic and Adult Fibroblast Cultures by Defined Factors, Cell, vol. 126, No. 4, Aug. 25, 2006, pp. 663-676.
Thomis et al., Defects in B Lymphocyte Maturation and T Lymphocyte Activation in Mice Lacking Jak3, Science, vol. 270, No. 5237, Nov. 3, 1995, pp. 794-797.
Timmermans et al., Generation of T Cells from Human Embryonic Stem Cell-Derived Hematopoietic Zones, The Journal of Immunology, vol. 182, No. 11, Jun. 1, 2009, pp. 6879-6888.
Veres et al., Low Incidence of Off-Target Mutations in Individual CRISPR-Cas9 and TALEN Targeted Human Stem Cell Clones Detected by Whole-Genome Sequencing, Cell Stem Cell, vol. 15, No. 1, Jul. 3, 2014, 8 pages.
Von Freeden-Jeffry et al., The Earliest T Lineage-Committed Cells Depend on IL-7 for Bcl-2 Expression and Normal Cell Cycle Progression, Immunity, vol. 7, No. 1, Jul. 1, 1997, pp. 147-154.
Welter et al., The NHGRI GWAS Catalog, A Curated Resource of SNP-Trait Associations, Nucleic Acids Research, vol. 42, Jan. 1, 2014, pp. D1001-D1006.
Wen et al., Jak3 Selectively Regulates Bax and Bcl-2 Expression to Promote T-Cell Development, Molecular and Cellular Biology, vol. 21, No. 2, Jan. 2001, pp. 678-689.
Yu et al., Induced Pluripotent Stem Cell Lines Derived from Human Somatic Cells, Science, vol. 318, No. 5858, Dec. 21, 2007, pp. 1917-1920.
Zou et al., Site-specific Gene Correction of a Point Mutation in Human iPS Cells Derived from an Adult Patient with Sickle Cell Disease, Blood, vol. 118, No. 17, Oct. 27, 2011, pp. 4599-4608.
Zuris et al., Cationic Lipid-Mediated Delivery of Proteins Enables Efficient Protein-Based Genome Editing in Vitro and in Vivo, Nature Biotechnology, vol. 33, No. 1, Jan. 2015, pp. 73-80.
Application No. CN201680048445.4, Office Action, dated Oct. 23, 2020, 9 pages with English translation.
Mansilla-Soto et al., "Repair of the Sickle-cell Disease Mutation in Human Stem Cells Using Crispr/cas9 and Single-Stranded Oligodeoxynucleotides", Molecular Therapy, vol. 23, No. 1, May 2015, S137.
Themeli, et al., "Generation of tumor-targeted human T lymphocytes from induced pluripotent stem cells for cancer therapy", Nature Biotechnology, vol. 31, No. 10, Oct. 2013, pp. 928-935.
Barrangou et al., "CRISPR-Cas Systems: Prokaryotes Upgrade to Adaptive Immunity", Molecular Cell, vol. 54, No. 2, 2014, pp. 234-244.
Application No. EP 16812552.4, Office Action, dated Mar. 18, 2021, 5 pages.
Application No. JP 2017565277, Office Action, dated Mar. 8, 2021, 18 pages with English translation.
Indian Application No. 201817001944, First Examination Report dated Nov. 26, 2021, 6 pages.
Application No. EP16812552.4, Office Action, dated May 19, 2022, 5 pages.
EP Application No. 16812552.4, Communication pursuant to Article 94(3) EPC, dated Oct. 10, 2022, 5 pages.

* cited by examiner

FIGURE 3A
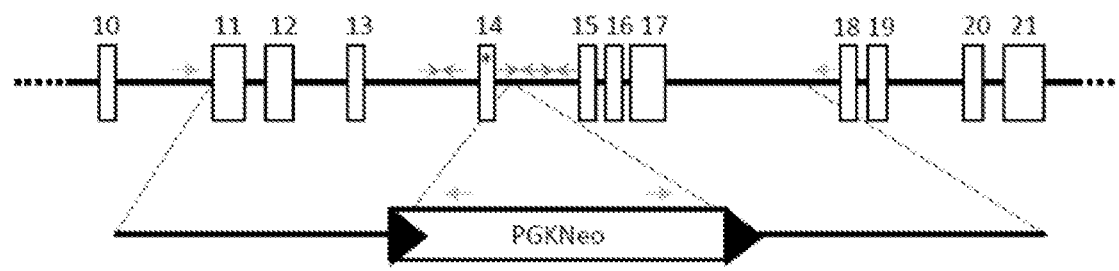
FIGURE 3B
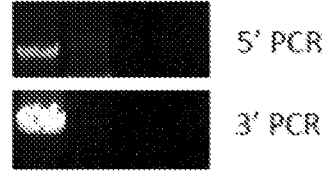
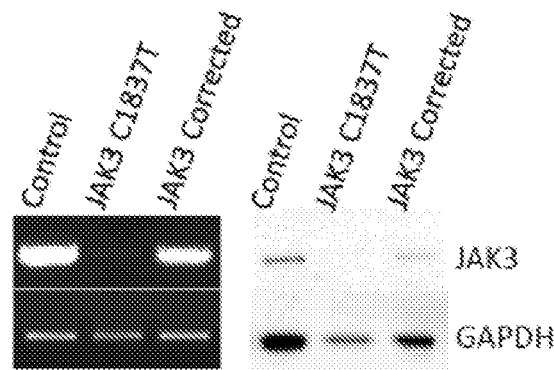

|  | Colonies examined | PCR positive colonies | % |
|---|---|---|---|
| gRNA #1 | 39 | 9 | 23 |
| gRNA #2 | 45 | 33 | 73.3 |
| gRNA #3 | 16 | 1 | 6.25 |
| gRNA #4 | 9 | 3 | 33.3 |
| gRNA #5 | 3 | 0 | 0 |
| gRNA #6 | 7 | 0 | 0 |
| gRNA #1 + #2 | 14 | 14 | 100 |
| gRNA #3 + #4 | 3 | 0 | 0 |
| gRNA #5 + #6 | 4 | 0 | 0 |

JAK3 patient C1837T   Heterozygous corrected   Homozygous corrected

FIGURE 20
A
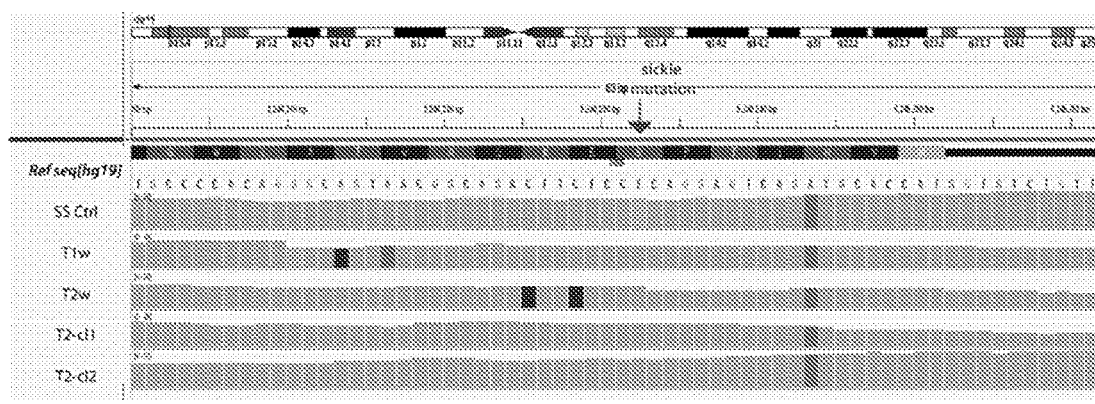
B
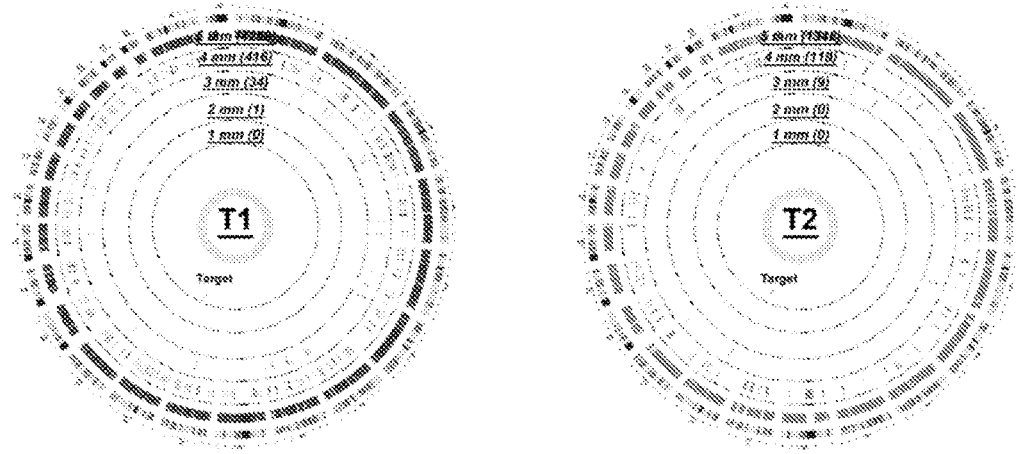

FIGURE 22
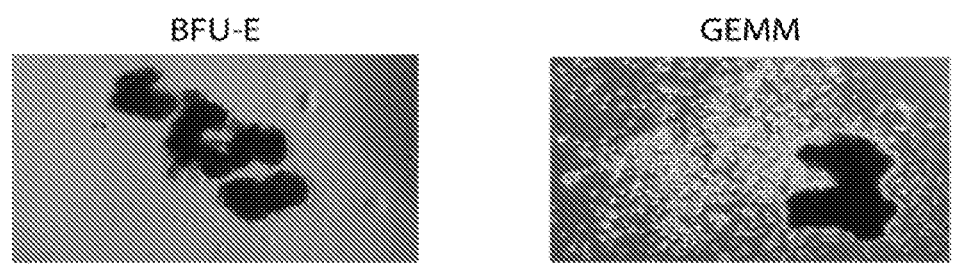
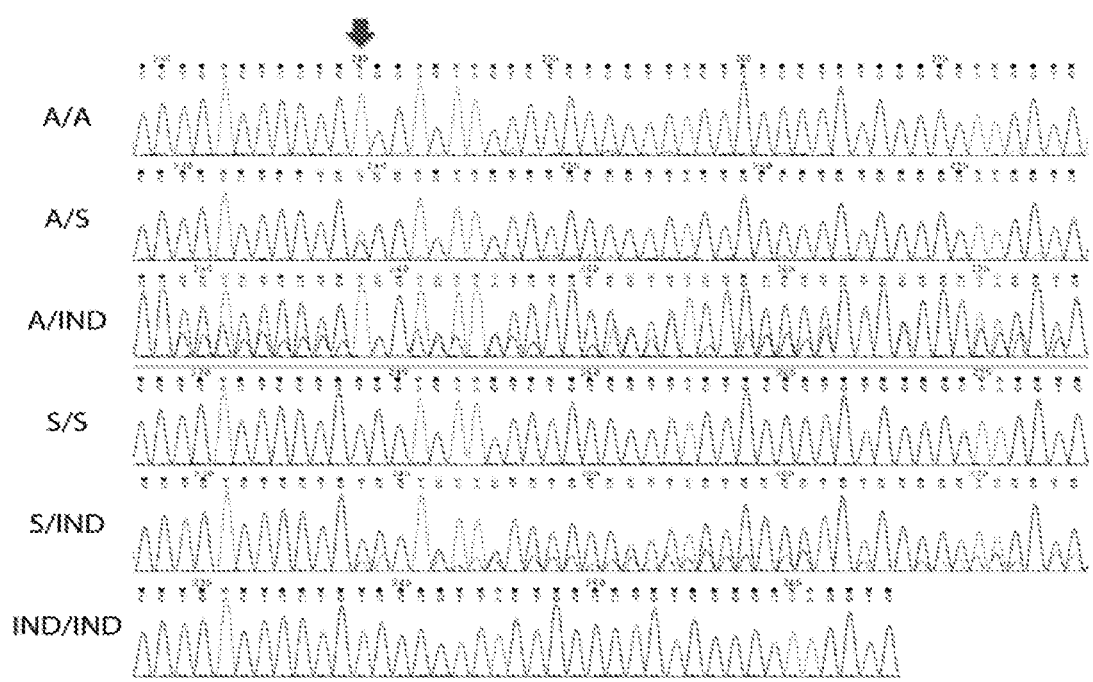
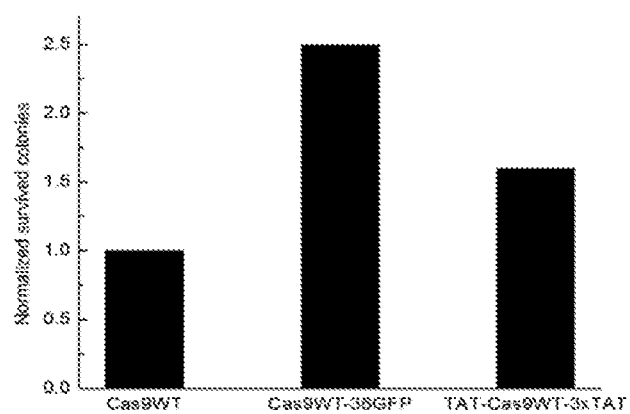

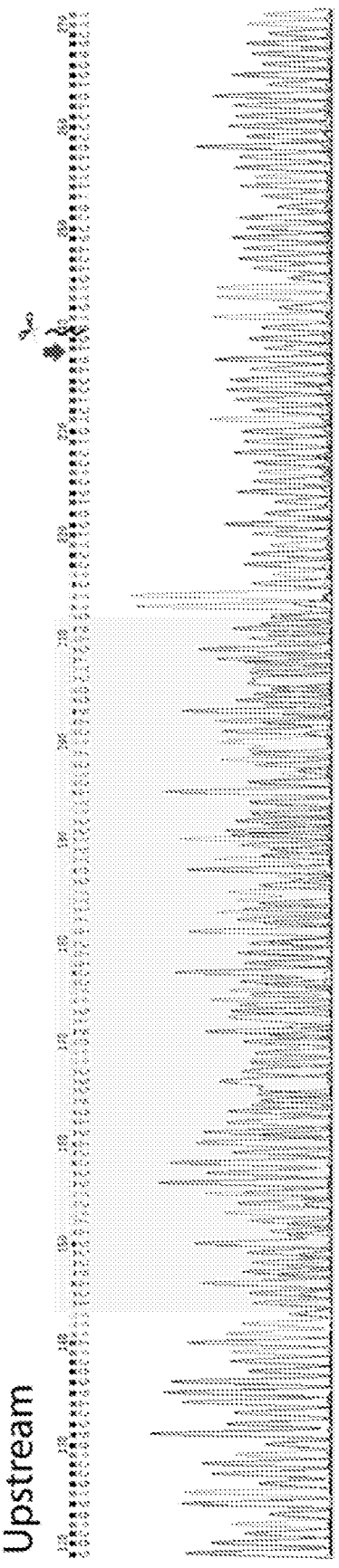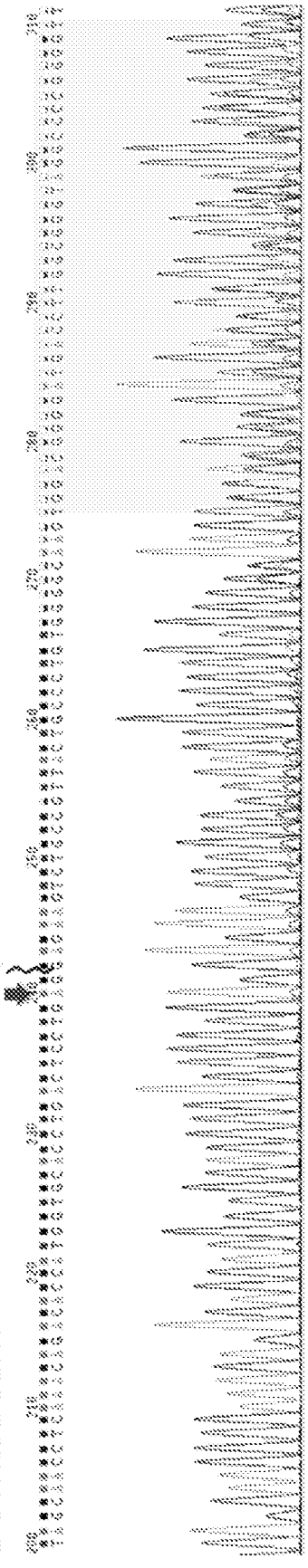
FIGURE 24

CRISPR/CAS9 COMPLEX FOR GENOMIC EDITING

This application claims the benefit of U.S. Provisional Application No. 62/181,138, filed Jun. 17, 2015, and U.S. Provisional Application No. 62/266,316, filed Dec. 11, 2015, both of which are hereby incorporated herein in their entireties by this reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1071098_SeqList.txt, created on May 29, 2018, and having a size of 44 KB. The sequence listing contained in this ASCII formatted document is part of the specification and is herein incorporated by reference in its entirety.

BACKGROUND

Clustered regularly interspaced short palindromic repeats (CRISPR)-associated (Cas) systems (CRISPR-Cas9 systems) are used for gene editing at desired genomic sites in mammalian cells. In CRISPR-Cas9 systems, a Cas9 nuclease is targeted to a genomic site by complexing with a guide RNA that hybridizes to a target site in the genome. This results in a double-strand break that initiates either non-homologous end-joining (NHEJ) or homology-directed repair (HDR) of genomic DNA via a double-strand or single-strand DNA repair template. However, repair of a genomic site via HDR is inefficient.

SUMMARY

Provided herein is a complex for correcting a mutation in the genome of a cell or populations of cells. The complex comprises a guide RNA (gRNA) comprising a first nucleotide sequence that hybridizes to a target DNA in the genome of the cell, wherein the target DNA comprises a mutation, and a second nucleotide sequence that interacts with a site-directed nuclease. The complex further comprises a recombinant site-directed nuclease operably linked to a supercharged protein, wherein the site-directed nuclease comprises an RNA-binding portion that interacts with the second nucleotide sequence of the guide RNA and wherein the site-directed nuclease specifically binds and cleaves the target DNA to create a double stranded break. The complex also comprises a single-stranded donor oligonucleotide (ssODN) that hybridizes to a genomic sequence flanking the double stranded break in the target DNA and integrates into the target DNA to correct a mutation in the target DNA.

Methods of site-specific modification of a target DNA in a cell or a population of cells are also provided. The methods comprise introducing a complex for correcting a mutation in the genome of the cell, wherein the complex is introduced into the cells under conditions that allow homology-directed repair (HDR) and integration of the ssODN into the target DNA. The method further provides for a high rate of cell survival in corrected cells.

Further provided is a method of treating a disease associated with a mutation in the genomic sequence encoding hemoglobin in a subject. The method comprises introducing into a population of cells obtained from the subject a complex for correcting a mutation in the genomic sequence encoding hemoglobin under conditions that allow homology-directed repair (HDR) to correct the mutation in the genomic sequence encoding hemoglobin and transplanting the corrected cells into the subject.

DESCRIPTION OF THE FIGURES

FIGS. 1A and 1B show flow cytometry of iPSC-derived T cells. JAK3 WT iPSCs (Control) and JAK3-deficient iPSCs (JAK3 C1837T) were differentiated into CD34+ cells on OP9 stromal cells and, subsequently, into T cells on OP9-DL4 monolayers. T-cell differentiation from JAK3-deficient iPSCs was absent compared to controls; no CD3+ T cells or CD3−CD16+CD56+ NK cells were observed (FIG. 1A), and no CD4+CD8+ double positive (DP), CD4+ single positive (SP), or CD8+ single positive (SP) T cells were detected (FIG. 1B). FIG. 1C shows the results of RT-qPCR assays for transcripts of key genes that regulate early events during specification of the T cell lineage. RNA levels are shown relative to GAPDH expression.

FIG. 2A shows apoptosis of JAK3-deficient, iPSC-derived T cells compared to JAK3 WT controls. Annexin V-positive cells were analyzed at T cell induction day 10 (TD10) and 17 (TD17). Four independent experiments were performed with control JAK3 WT cells (Control) and 5 independent experiments were performed with JAK3-deficient cells (JAK3 C1837T). *P<0.005. FIG. 2B shows the results of RT-qPCR assays for anti-apoptotic BCL2 and proapoptotic BAX expression in two lines (1 and 2) from JAK3 WT (Control) and JAK3-deficient cells (JAK3 C1837T). ND, not determined (due to insignificant JAK3 qPCR signal). RNA levels are shown relative to GAPDH expression. FIG. 2C shows flow cytometry of JAK3-deficient iPSC derived T cells transduced with BCL2-2A-GFP lentivirus to assess effects on NK (CD16+56+) and T cell (CD3+) development and DP (CD4+CD8+) to SP (CD4+ or CD8+) T cell maturation.

FIGS. 3A-3D show that CRISPR/Cas9 enhanced correction of the JAK3 C1837T mutation in patient-specific iPSCs. FIG. 3A depicts the strategy for genome modification using CRISPR/Cas9 to induce double-strand breaks in the JAK3 locus and a template for homology directed repair. Top line, structure of the JAK3 gene. Open boxes, exons. Asterisk, C1837T mutation. Arrows, guide RNAs. FIG. 3B, top, shows PCR analysis demonstrating homologous recombination; primers for 5' and 3' analysis are indicated. (Lower Left) RT-PCR analysis demonstrating JAK3 mRNA expression in JAK3 WT (Control), JAK3-deficient (JAK3 C1837T), and corrected (JAK3 Corrected) T cells. (Lower Right) Western Blot analysis demonstrating JAK3 protein expression in JAK3 WT (Control), JAK3-deficient (JAK3 C1837T), and corrected (JAK3 Corrected) T cells. FIG. 3C provides a summary of targeting efficiencies of guide RNAs. (FIG. 3D) Sanger sequencing of the PCR amplicons from parental JAK3 iPSCs (Left), heterozygous corrected (Middle) and homozygous corrected iPSCs (Right). The two heterozygous clones were corrected with gRNA2+wild type Cas9, and the homozygous clone was corrected with gRNA1+gRNA2+nickase Cas9 (D10A).

FIG. 4A shows the expression of T cell developmental markers in JAK3 WT (Control, n=3), JAK3-deficient (JAK3 C1837T, n=5) and JAK3-corrected (JAK3 Corrected, n=6) T cells. Cells were stained with indicated antibodies and analyzed by flow cytometry at T cell induction Day 14, 21, 28 and 35 (TD 14, 21, 28 and 35). FIG. 4B shows T cell receptor (TCR) Vβ analysis of JAK3-corrected T cells. A highly diverse repertoire of TCR Vβ is represented in T cells derived from corrected SCID patient iPSCs. FIG. 4C shows flow cytometry demonstrating T cell activation in JAK3-corrected T cells. T cells derived from JAK3 WT (Control) and JAK3-corrected iPSCs were stimulated with anti-CD3/28 beads for 3 days before analysis of activation markers CD25 and CD69. The data were gated on CD3+ populations.

FIGS. 20A and 20B show the results of whole genome sequencing (WGS) analysis of 4 iPSC clones corrected with TAT-Cas9WT-36GFP-INF7 RNP/ssODNs. (A) On-target sequence analysis demonstrates sickle correction and wobble-base substitution. (B) WGS off-target analysis of 45 genomic loci with homology to T1 and T2 sgRNA is shown.

FIGS. 22A-C show correction of colonies derived from single CD34+ progenitors. (A) BFU-E and CFU-GEMM colonies derived from nucleoporated human sickle CD34+ cells. (B) Representative Sanger Sequencing results of colonies obtained from human sickle CD34+ cells after nucleoporation with TAT-Cas9WT-36GFP-INF7 RNP/ssODN. (C) Colony survival after nucleoporation with Cas9WT, Cas9WT-36GFP, and TAT-Cas9WT-3×TAT RNPs plus ssODNs.

FIG. 24 shows non-specific modifications near Cas9WT RNP targeting site. BFU-E colonies from Cas9WT RNP/ssODN nucleoporated sickle CD34+ cells contain indels that do not appear to be initiated at the cutting site. The top sequence labeled 'Upstream' is representative of non-specific modifications upstream of the expected cleavage site. The bottom sequence labeled 'Downstream' represents non-specific modifications observed downstream of the expected cleavage site. Arrows indicate the position of the sickle mutation and scissors indicate the expected cleavage site of Cas9WT RNP.

DETAILED DESCRIPTION

Figure 1A:
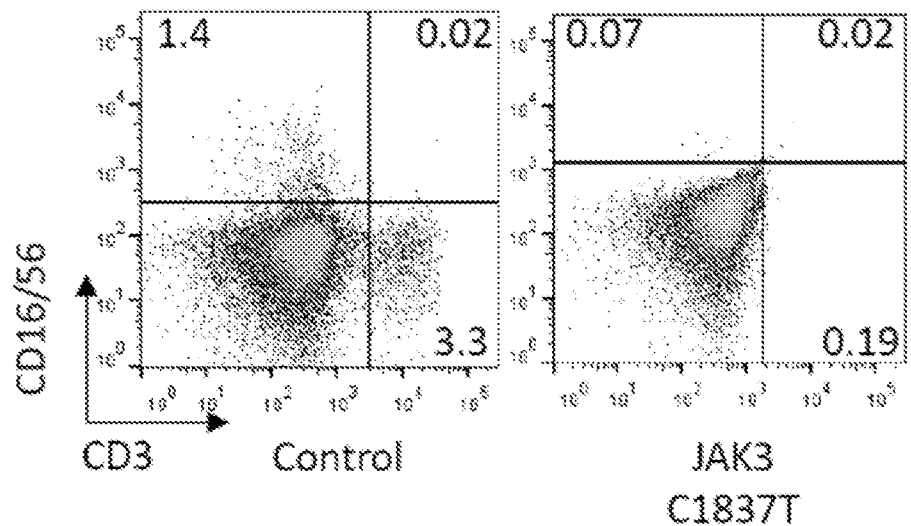
FIGS. 1A-1C show that in vitro differentiation of JAK3 C1837T patient induced pluripotent stem cells (iPSCs) recapitulates SCID phenotypes.

Provided herein are CRISPR/Cas9 complexes for genomic modification of cells. Methods of using the complexes provided herein result in increased efficiency of modification, an increased cell survival ratio and/or an increased ratio of HDR to NHEJ in the cells. These complexes and methods can be used for therapeutic purposes, for example, to correct a mutation in cells, wherein the mutation is associated with a disease or disorder.

Provided herein is a complex for correcting a mutation in the genome of a cell comprising (a) a guide RNA (gRNA) comprising a first nucleotide sequence that hybridizes to a target DNA in the genome of a cell, wherein the target DNA comprises a mutation, and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the guide RNA and wherein the site-directed nuclease specifically binds and cleaves the target DNA to create a double stranded break; and (c) a single-stranded donor oligonucleotide (ssODN) that hybridizes to a genomic sequence flanking the double stranded break in the target DNA and integrates into the target DNA to correct a mutation in the target DNA.

It is understood that the complex comprising a guide RNA (gRNA), a recombinant site-directed nuclease and a donor nucleotide described herein does not occur in nature. The complex, however, provides the elements necessary with the required configuration and stoichiometry to efficiently and effectively modify cells. The gRNA molecule binds to the site-directed nuclease and targets the nuclease to a specific location within the target DNA. A gRNA comprises a first nucleotide sequence that hybridizes to a target DNA in the genome of a cell, wherein the target DNA comprises a mutation, and a second nucleotide sequence that interacts with a site-directed nuclease. The complexes described herein can comprise one or two separate gRNAs. Therefore, the term guide RNA includes both a single guide RNA and a double guide RNA. An example of a guide sequence that can be used to correct a mutation associated with sickle cell anemia is set forth herein as TAACGGCAGACTTCTCCAC (SEQ ID NO: 1). An example of a guide sequence comprising a stem loop for Cas9 binding is provided herein as GTAACGGCAGACTTCTCCACGTTTTAGAGCTA-GAAATAGCAAGTTAAAATAAGG CTAGTCCGTTAT-CAACTTGAAAAAGTGGCACCGAGTCGGTGCTT-TTTTT (SEQ ID NO: 2). It is noted that the 5'G of SEQ ID NO: 2 was added by T7 during in vitro transcription.

In the complexes described herein, the recombinant site-directed nuclease can be an RNA-guided site-directed nuclease, for example, a Cas protein from any bacterial species or a functional fragment thereof. For example, the Cas protein can be a Cas9 protein or a functional fragment thereof. As used herein, the term "Cas9" means a Cas9 protein or a fragment thereof present in any bacterial species that encodes a Type II CRISPR/Cas9 system. See, for example, Makarova et al. *Nature Reviews*, Microbiology, 9: 467-477 (2011), including supplemental information, hereby incorporated by reference in its entirety. For example, the Cas9 protein or a fragment thereof can be from *Streptococcus pyogenes*. Full-length Cas9 is an endonuclease that includes a recognition domain and two nuclease domains (HNH and RuvC, respectively). In the amino acid sequence, HNH is linearly continuous, whereas RuvC is separated into three regions, one left of the recognition domain, and the other two right of the recognition domain flanking the HNH domain. Cas9 from *Streptococcus pyogenes* is targeted to a genomic site in a cell by interacting with a guide RNA that hybridizes to a 20-nucleotide DNA sequence that immediately precedes an NGG motif recognized by Cas9. This results in a double-strand break that is repaired via HDR by a donor nucleotide, for example, a ssODN or a double stranded DNA construct that hybridizes to a genomic sequence flanking the double stranded break in the target DNA and integrates into the target DNA to correct a mutation in the target DNA.

In the complexes provided herein, the molar ratio of gRNA to site-directed nuclease operably linked to a supercharged protein to ssODN can be from about 1:1:0.2 to about 1.5:1:2.0. For example, the molar ratio of gRNA to site-directed nuclease operably linked to a supercharged protein to ssODN can be about 1:1:1, 1.1:1:1, 1:1:1.15, 1:1:1.25, 1:1:1.30; 1:1:1.35; 1:1:1.40; 1:1:1.50, 1.2:1:1, 1.3:1:1. 1.4:1:1, 1.5:1:1, 1.5:1:1.15, 1.5:1:1.25, 1.5:1:1.35; 1.5:1:1.40, 1.5:1:1.45; 1.5:1:1.50; 1.5:1:1.55; 1.5:1:1.60; 1.5:1:1.65; 1.5:1:1.70; 1.5:1:1.75; 1.5:1:1.80; 1.5:1:1.85; 1.5:1:1.90; 1.5:1:1.95; 1.5:1:2.0 or any ratio in between these ratios. Complexes having these molar ratios can be used in any of the methods described herein. Methods for preparing a complex prior to introducing the complex into a cell or a population of cells are set forth in the Examples.

As used herein, a supercharged protein can be a superpositively charged protein that has an overall positive charge that is greater than its corresponding unmodified protein. For example, the superpositively charged protein can be a superpositively charged green fluorescent protein (GFP) that has an overall positive charge from about +5 to about +40. For example, the overall positive charge can be about +5, +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39 or +40.

The supercharged protein can be operably linked to the amino-terminus or the carboxy-terminus of the nuclease. It is also contemplated that the supercharged protein can be associated with the nuclease, without necessarily being covalently linked to the nuclease. An example of a supercharged protein is a superpositively charged GFP, for example, +36 GFP. +36 GFP can be operably linked to the amino or carboxy-terminus of Cas9 or a functional fragment thereof. See, for example, McNaughton et al., "Mammalian cell penetration, siRNA transfection, and DNA transfection by supercharged proteins," PNAS 106(15): 6111-6116. An example of a polypeptide comprising +36 GFP operably linked to the carboxy-terminus of Cas9 is provided herein as SEQ ID NO: 3.

The nuclease can also be operably linked to a supercharged protein and one or more positively charged peptides, for example, one or more transactivating transcriptional activator (TAT) peptide can be operably linked to the amino-terminus or the carboxy-terminus of the nuclease. For example, and not to be limiting, a superpositively charged protein can be operably linked to the carboxy-terminus of the nuclease and one or more TAT peptides (for example, 1×TAT, 2×TAT, 3×TAT, 4×TAT, etc.) can be operably linked to the amino-terminus of the nuclease. An example of polypeptide comprising a TAT peptide operably linked to the amino-terminus of the nuclease and a superpositively charged GFP operably linked to the carboxy-terminus of the nuclease is provided herein as SEQ ID NO: 4. Polypeptide sequences that are at least about 75% identical to SEQ ID NO: 3 or SEQ ID NO: 4 are also provided. For example, polypeptide sequences that are at least about 75%, 80%, 85%, 90%, 95%, 99% or any percentage in between are also provided.

The nuclease can also be operably linked to a supercharged protein and one or more negatively charged peptides, for example, a negatively charged peptide of about 10 to about 25 amino acids in length, for example, SEQ ID NO: 50, can be operably linked to the carboxy-terminus of the site-directed nuclease. For example, and not to be limiting, a superpositively charged protein can be operably linked to the carboxy-terminus of the nuclease and a negatively charged peptide can be operably linked to the carboxy-terminus of the superpositively charged protein.

As used throughout, recombination is a process of exchange of genetic information between two polynucleotides. Homology-directed repair (HDR) refers to DNA repair that takes place, for example, during repair of double-strand breaks in cells. This process requires nucleotide sequence homology and uses a donor molecule, for example, a single stranded or a double stranded nucleotide sequence as a template for repair of a target genomic sequence, i.e., the genomic sequence with the double-strand break, and leads to the transfer of genetic information from the donor to the target genomic sequence. Homology-directed repair can result in a modification of the sequence of the target genomic sequence. For example, HDR can result in an insertion, a deletion or a mutation in the target genomic sequence. Part or all of the sequence of the donor polynucleotide can be incorporated into the target DNA. It is also contemplated that the donor polynucleotide, a portion of the donor polynucleotide, a copy of the donor polynucleotide, or a portion of a copy of the donor polynucleotide integrates into the target DNA.

As used throughout, by non-homologous end joining (NHEJ) is meant the repair of double-strand breaks in DNA by direct ligation of the break ends to one another without the need for a homologous template (in contrast to homology-directed repair, which requires a homologous sequence to guide repair).

The complexes and methods provided herein can be used to correct any mutation in a target DNA by HDR. For example, and not to be limiting, the complexes can be used to replace an incorrect nucleotide sequence with a correct nucleotide sequence (e.g., to restore function to a target polynucleotide sequence that is impaired due to a loss of function mutation, i.e., a SNP) at a specific site in the genome. These mutations can be associated with an autoimmune disorder, a genetic disease, a blood disorder, a T cell disorder, a monogenic disorder, cancer, a neurodegenerative disease, a cardiovascular disease or an infectious disease, to name a few. For example, and not to be limiting, the complexes and methods provided herein can be used to correct a mutation associated with sickle cell disease (i.e., a mutation in a hemoglobin gene, for example, a GAG to GTG mutation at codon 6 of the beta-globin gene that results in a glutamic acid to valine substitution), severe combined immunodeficiency (SCID) (for example, a mutation in JAK3), beta thalassemia or Wiskott-Aldrich Syndrome.

Correction of single mutations or multiple mutations can be performed with one or more complexes. The complexes and methods provided herein can also be used to insert sequences into a specific site in the genome to correct a deletion, as opposed to making a correction or a substitution. The complexes and methods provided herein can also be used to insert a nucleotide sequence that encodes an a functional polypeptide into a specific site in the genome of the cell, in order to express the functional polypeptide in the cell. The functional polypeptide can be a polypeptide that is endogenous (i.e., normally expressed by the cell) or exogenous to the cell (i.e. not normally expressed by the cell). For example, chimeric antigen receptor (CAR) sequences can be inserted into the genome of a T cell precursor in order to generate cancer specific T cells for the treatment of cancer. In another example, the complexes and methods provided herein can be used to inhibit the activity of a gene at a specific site in the genome of the cell. For example, the complexes and methods provided herein can be used to insert sequences into the CXCR4 or CCR5 receptor to treat or prevent HIV infection.

The complexes provided herein can modify or alter target DNA with surprisingly high efficiency as compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% or 80% or higher or any percentage in between these percentages. The efficiency of alteration can also be greater than or equal to about 80%. Therefore, also provided herein are populations of cells, wherein at least 5%, 10%, 15%, 20%, 25%, 30%, 35%, 40%, 45%, 50%, 55%, 60%, 65%, 70%, 75% or 80% or higher or any percentage in between are altered. For example, a mutation associated with sickle cell disease or another disorder has been corrected. If a population of cells comprising a mutation associated with sickle cell disease is contacted with a CRISPR/Cas complex described herein and the mutation is corrected in about 5% of the cells, the efficiency of modification or alteration is about 5%. Optionally, a population of cells wherein the mutation associated with sickle cell disease is corrected in about 30% of the cells, including, for example, 27%, 28% and 29% is sufficient to treat sickle cell disease, upon transplantation in a subject with sickle cell disease. Optionally, a mutation associated with sickle cell disease is corrected in about 40%, 50%, 60%, 70%, 80%, 90% or higher or any percentage in between, of the cells in the population.

In addition to altering the target DNA with high efficiency, the complexes provided herein can also increase the ratio of HDR to NHEJ in a population of cells contacted with the complex. The HDR/NHEJ ratio can be from about 10 to about 0.5. For example, the HDR/NHEJ ratio can be about 10, 9, 8, 7, 6, 5, 4, 3, 2, 1, 0.5 or less or any ratio in between these ratios. In addition to high efficiency of correction and high rate of HDR to NHEJ, the cell survival rate for corrected cells can be at least about 50%, 60%, 70%, 80%, 90% or higher and any percentage in between.

Any cell(s) can be modified or derived using the complexes described herein. Introduction of the complex into the cells can be cell cycle dependent or cell cycle independent. Methods of synchronizing cells to increase the proportion of cells in a particular phase, for example, the S-phase, are known in the art. See, for example, Takahashi et al. "Efficient introduction of a gene into hematopoietic cells in S-phase by electroporation," *Exp. Hematol.* 19(5):343-346 (1991). Depending on the type of cell to be modified, one of skill in the art can readily determine if cell cycle synchronization is necessary.

The cell(s) can be a eukaryotic cell, for example, a mammalian cell. The cell can also be prokaryotic or a plant cell. The cell can be a human cell. The cell can be a germ cell, a somatic cell, a stem cell, a precursor cell or a progenitor cell. The precursor cell can be, for example, a pluripotent stem cell or a multipotent stem cell, like a hematopoietic stem cell. As used throughout, pluripotent cells include induced pluripotent stem cells. Methods of making induced pluripotent stem cells and known in the art and described in the Examples. The cell can also be CD34+ cell, optionally derived from an induced pluripotent stem cell. The CD34+ cell can be selected from the group consisting of a primary CD34+ hematopoietic progenitor cell, a CD34+ peripheral blood cell, a CD34+ cord blood cell and a CD34+ bone marrow cell. The cell can also be a primary cell, for example, a primary CD34+ hematopoietic progenitor cell. The cells are cells that are not cancer cells, cells that are not tumor cells or cells that are not transformed cells. Cells can be screened before or after correction for evidence of undesirable genetic characteristics. Further provided is a cell comprising any of the complexes described herein. The cell can be in vitro, ex vivo or in vivo.

Further provided is a method of site-specific modification of a target DNA in a population of cells comprising introducing into the cells any of the complexes described herein, wherein the complex is introduced into the cells under conditions that allow homology-directed repair (HDR) and integration of a donor nucleotide, for example, a ssODN or double stranded nucleotide sequence into the target DNA. The complex can be introduced into the cell via nucleoporation. Methods for nucleoporation are known in the art. See, for example, Maasho et al. "Efficient gene transfer into the human natural killer cell line, NKL, using the amaxa nucleofection system," *Journal of Immunological Methods* 284(1-2): 133-140 (2004); and Aluigi et al. "Nucleofection is an efficient non-viral transduction technique for human bone marrow derived mesenchymal stem cells," *Stem Cells* 24(2): 454-461 (2006)), both of which are incorporated herein in their entireties by this reference.

In some of the methods provided herein, the donor nucleotide, for example, a ssODN or a double stranded nucleotide sequence integrates into a target DNA and corrects a mutation in the target DNA. In the methods provided herein the ratio of HDR to NHEJ in a population of cells is increased relative to other CRISPR-Cas9 delivery methods. The HDR/NHEJ ratio can be from about 10 to about 0.5. For example, the HDR/NHEJ ratio can be about 10, 9, 8, 7, 6, 5, 4, 3, 2, 1, 0.5 or less or any ratio in between these ratios. In the methods provided herein, the efficiency of alteration by HDR can be at least about 5%, 10%, 15%, 20%, 25%, 30%, 35%, 40%, 45%, 50%, 55%, 60%, 65%, 70%, 75%, 80% or greater or any percentage in between these percentages. The efficiency of alteration by HDR can also be greater than or equal to about 80%. For example, if a population of cells comprising a mutation associated with sickle cell anemia is contacted with a CRISPR/Cas complex described herein and the mutation is corrected in about 5% of the cells, the efficiency of alteration by HDR is about 5%. The population of cells can be obtained from the subject having a disorder such that at least about 5%, 10%, 15%, 20%, 25%, 30%, 35%, 40%, 45%, 50%, 55%, 60%, 65%, 70%, 75% or 80% or greater or any percentage in between these percentages, of the cells undergo HDR to correct a mutation associated with the disorder. In some cases greater than 80% of the cells from the subject will undergo HDR to correct a mutation associated with the disorder. In the methods described herein, between about 50% and 99% of the cells survive after introduction of the complex. For example, great than about 50%, 60%, 70%, 80%, 90%, 95%, 99% or any percentage in between these percentages, of corrected cells survive after introduction of the complex.

Further provided is a method of treating a disease associated with a mutation in the genomic sequence encoding hemoglobin in a subject comprising: (a) introducing into a population of cells obtained from the subject a complex comprising (1) a guide RNA (gRNA) comprising a first nucleotide sequence that hybridizes to a target DNA in the genome of a cell, wherein the target DNA is a hemoglobin gene that comprises a mutation, and a second nucleotide sequence that interacts with a site-directed nuclease; (2) a recombinant site-directed nuclease operably linked to a supercharged protein, wherein the site-directed nuclease comprises an RNA-binding portion that interacts with the second nucleotide sequence of the guide RNA and wherein the site-directed nuclease specifically binds and cleaves the target DNA to create a double stranded break; and (3) a single-stranded donor oligonucleotide (ssODN) that hybridizes to a genomic sequence flanking the double stranded break in the target DNA and integrates into the target DNA to correct the mutation in hemoglobin gene; and (b) transplanting the corrected cells into the subject.

In the methods for treating a disease associated with a mutation in the genomic sequence encoding hemoglobin in a subject, for example, sickle cell anemia, the subject with sickle cell anemia can optionally be a transfusion dependent subject or a subject with at least one silent infarction. The subject can also be less than about twelve months, eleven months, ten months, nine months, eight months, seven months, six months, five months, four months, three months, two months, or one month in age. As infants are routinely screen for sickle cell disease, infants can be treated before symptoms of the disease manifest. The methods provided herein can further comprise diagnosing a subject with a disorder, for example, sickle cell disease.

As set forth above, cells can be obtained from the subject with the disease or from a related donor. For example, bone marrow cells can be obtained or harvested from the subject. Bone marrow harvesting involves collecting stem cells with a needle placed into the soft center of the bone, the marrow. Bone marrow can be harvested for example, from the hip bones or sternum of the subject. From about 500 ml to about 1 liter of bone marrow can be obtained from the subject.

In any of the methods provided herein the cell(s) can be a eukaryotic cell, for example, a human cell. The cell can be a germ cell, a stem cell, a precursor cell. The precursor cell can be, for example, a pluripotent stem cell or a hematopoietic stem cell. As used throughout, pluripotent cells include induced pluripotent stem cells. Methods of making induced pluripotent stem cells and known in the art and described in the Examples. The cell can also be CD34+ cell. The CD34+ cell can be selected from the group consisting of a primary CD34+ hematopoietic progenitor cell, a CD34+ peripheral blood cell, a CD34+ cord blood cell and a CD34+ bone marrow cell. The cell can also be a primary cell, for example, a primary CD34+ hematopoietic progenitor cell. The cells are that are not cancer cells, cells that are not tumor cells or cells that are not transformed cells. The cell can be in vitro or ex vivo. The cells can also be in a pharmaceutically acceptable composition.

The methods provided herein can further comprise culturing the cells corrected with HDR. For example, the cells can be cultured under conditions for expansion or under conditions that promote differentiation of the corrected cells into T-cells. For example, and not to be limiting, using the methods provided herein, after a mutation has been corrected in induced pluripotent stem cells via HDR, the corrected cells can be co-cultured with human bone marrow stromal cells to generate CD34+ cells. The CD34+ cells can then be cultured under conditions that differentiate the CD34+ cells into T cells.

The methods provided herein can further comprise screening the corrected cells for the proper correction, other mutations, or NEJ prior to transplantation. Optionally cells can be screened to detect cells with one or more corrections.

In the methods provided herein, the cells can be transplanted into the subject after modification, for example, after correction of a mutation by HDR. The cells can be transplanted into the subject with or without differentiation. For example, modified hematopoietic stem cells (HSCs) can be administered in a bone marrow transplant, wherein the HSCs are allowed to differentiate and mature in vivo in a subject Alternatively, the modified cells can be differentiated into a desired population of cells prior to transplantation.

As used herein, transplanting, introducing or administering cells to a subject refers to the placement of cells into a subject. For example, the cells described herein comprising a target DNA sequence corrected or modified according to the methods described herein can be transplanted into a subject, by an appropriate route which results in at least partial localization of the transplanted cells at a desired site. The cells can be implanted directly to the desired site, or alternatively can be administered by any appropriate route which results in delivery to a desired location in the subject where at least a portion of the implanted cells remain viable. For example, the cells can be administered systemically, via intravenous infusion. The period of viability of the cells after administration to a subject can be as short as a few hours, e.g. twenty-four hours, to a few days, to as long as several years.

For ex vivo methods, cells can be autologous cells, i.e., a cell or cells taken from a subject who is in need of modification of a target DNA in the cell or cells (i.e., the donor and recipient are the same individual). As described herein, the modification can be, for example correction of a mutation, insertion of a sequence that inhibits activity of a protein or insertion of a sequence that increases expression of a protein, for example, insertion of a sequence encoding a chimeric antigen receptor that can be used to target cancer cells. Autologous cells can be used to avoid immunological reactions that can result in rejection of the cells. In other words, when using autologous cells, the donor and recipient are the same subject. Alternatively, the cells can be heterologous, e.g., taken from a donor, preferably a related donor. The second subject can be of the same or different species. Typically, when the cells come from a donor, they will be from a donor who is sufficiently immunologically compatible with the recipient to reduce the chances of transplant rejection, and/or to reduce the need for immunosuppressive therapy. The cells can also be obtained from a xenogeneic source, i.e., a non-human mammal that has been genetically engineered to be sufficiently immunologically compatible with the recipient, or the recipient's species. Any of the methods of treating a disorder described herein can further comprise administering one or more immunosuppressants to the subject.

In the methods involving transplantation, a subject optionally undergoes myeloablative therapy prior to transplantation of any of the cells described herein. The myeloablative therapy can include administering one or more doses of chemotherapy, radiation therapy, or both, that results in severe or complete depletion of healthy bone marrow cells. In another example, the subject can undergo submyeloablative therapy that includes administering one or more doses of chemotherapy, radiation therapy, or both, that depletes a portion of the healthy bone marrow cells. The cells can also be transplanted into subjects that have undergone nonablative chemotherapy. For example, the cells can be transplanted into a subject that has been treated with Busulfan, Fludarabine and/or Treosulfan.

In the methods involving transplantation, an effective dose or amount of corrected cells is administered to the subject. The terms effective amount and effective dosage are used interchangeably. The term effective amount is defined as any amount necessary to produce a desired physiologic response. In some methods, about $1 \times 10^6$ to about $7 \times 10^6$ corrected cells/kg can be administered, but this amount can vary depending on the associated disorder. The percentage of corrected cells that Effective amounts and schedules for administering the cells may be determined empirically, and making such determinations is within the skill in the art. The dosage ranges for administration are those large enough to produce the desired effect (e.g., treatment of a disease, for example, sickle cell anemia). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and the agent can be administered in one or more dose administrations daily, for one or multiple days as needed.

As used throughout, a subject can be a vertebrate, more specifically a mammal (e.g., a human, horse, cat, dog, cow, pig, sheep, goat, mouse, rabbit, rat, and guinea pig). The term does not denote a particular age or sex. Thus, adult and newborn subjects, whether male or female, are intended to be covered. As used herein, patient or subject may be used interchangeably and can refer to a subject with or at risk of developing a disorder. The term patient or subject includes human and veterinary subjects.

As used herein the terms treatment, treat, or treating refers to a method of reducing one or more of the effects of the disorder or one or more symptoms of the disorder, for example, sickle cell disease, by eliciting an immune response in the subject. Thus in the disclosed method, treatment can refer to a 10%, 20%, 30%, 40%, 50%, 60%, 70%, 80%, 90%, or 100% reduction in the severity of sickle cell disease and other disorders. For example, a method for treating sickle cell disease is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disorder or symptoms of the disorder.

Also provided is a method of correcting a mutation associated with a T-cell disorder comprising introducing into a population of cells obtained from a subject with the T-cell disorder a complex comprising: (a) a guide RNA (gRNA) comprising a first nucleotide sequence that hybridizes to a target DNA in the genome of a cell, wherein the target DNA comprises the mutation associated with the T-cell disorder, and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the gRNA and wherein the site-directed nuclease specifically binds and cleaves the target DNA that comprises the mutation associated with the T-cell disorder to create a double stranded break in the target DNA; and (c) a single stranded donor oligonucleotide (ssODN) comprising a third nucleotide sequence that hybridizes to a genomic sequence flanking the double stranded break in the target DNA and that integrates into the target DNA to correct the mutation associated with the T-cell disorder, wherein the complex is introduced into the cell under conditions that allow homology-directed repair (HDR) to correct the mutation associated with the T-cell disorder.

In the methods provided herein, the target DNA comprising a mutation associated with a T-cell disorder can be a target DNA that encodes a protein associated with T-lymphocyte development. For example, the target DNA can encode JAK3. Such corrected cells can be used, for example, in the treatment of SCID.

In addition to correcting mutations in the genome of a cell, the complexes and methods provided herein can also be used to insert functional polypeptides at specific sites in the genome of a cell, such that the polypeptide is expressed by the cell. The polypeptide can be expressed in the cell or on the cell surface.

Also provided is a method of making tumor-specific T-cell precursor cells comprising introducing into a population of T-cell precursor cells a complex comprising: (a) a guide (gRNA) comprising a first nucleotide sequence that hybridizes to a target DNA in the genome of the T cell precursor cells and a second nucleotide sequence that interacts with a site-directed nuclease; (b) a recombinant site-directed nuclease operably linked to a supercharged protein, wherein the site-directed nuclease comprises an RNA-binding portion that interacts with the second nucleotide sequence of the gRNA and wherein the site-directed nuclease specifically binds and cleaves the target DNA to create a double stranded break; and (c) donor nucleotide sequence comprising a third nucleotide sequence that encodes a chimeric antigen receptor (CAR) and a fourth nucleotide sequence that hybridizes to a genomic sequence flanking the double stranded break in the target DNA, wherein the complex is introduced into the T-cell precursor cells under conditions that allow homology-directed repair (HDR) and integration of the third nucleotide sequence into the target DNA to form modified T-cell precursor cells that express the CAR.

The T cell precursor cells can be obtained from a subject with cancer. As set forth above, the HDR/NHEJ ratio can be from about 10 to about 0.5. For example, the HDR/NHEJ ratio can be about 10, 9, 8, 7, 6, 5, 4, 3, 2, 1, 0.5 or any ratio in between these ratios. In the methods provided herein, the efficiency of alteration by HDR can be at least about 5%, 10%, 15%, 20%, 25%, 30%, 35%, 40%, 45%, 50%, 55%, 60%, 65%, 70%, 75%, 80% or any percentage in between these percentages. The efficiency of alteration by HDR can also be greater than or equal to about 80%. For example, when using the methods described herein, if a nucleotide sequence encoding an functional polypeptide, for example, a nucleotide sequence that encodes a CAR, is inserted in about 5% of the cells, the efficiency of alteration by HDR is about 5%. The population of cells can be obtained from the subject that has cancer such that at least about 5%, 10%, 15%, 20%, 25%, 30%, 35%, 40%, 45%, 50%, 55%, 60%, 65%, 70%, 75% or 80% or any percentage in between these percentages, of the cells undergo HDR to insert a nucleotide sequence that encodes a chimeric antigen receptor (CAR) and form cells that express the CAR. In some cases greater than 80% of the cells from the subject will undergo HDR to correct a mutation associated with the disorder.

The modified T-cell precursor cells that express the CAR can be transplanted into a subject with cancer. As used herein, cancer is a disease characterized by the rapid and uncontrolled growth of aberrant cells. Cancer cells can spread locally or through the bloodstream and lymphatic system to other parts of the body. Examples of cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The modified T-cell precursor cells that express the CAR exhibit anti-tumor immunity when the antigen binding domain binds to its corresponding antigen.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Correction of SCID by CRISPR/Cas9 Enhanced Gene Replacement

Mutations of the Janus family kinase JAK3 gene cause severe combined immunodeficiency (SCID). JAK3 deficiency in humans is characterized by the absence of circulating T cells and natural killer (NK) cells with normal numbers of poorly functioning B cells (T−B+NK−). As shown herein, using SCID patient-specific induced pluripotent stem cells (iPSCs) and a T cell in vitro differentiation system, a complete block in early T cell development of JAK3-deficient cells was demonstrated. Correction of the novel JAK3 mutation by CRISPR/Cas9 enhanced gene replacement restores normal T cell development, including the production of mature T-cell populations with a broad T Cell Receptor (TCR) repertoire. Whole genome sequencing of corrected cells demonstrated no CRISPR/Cas9 off-target modifications. Thus, provided herein is a novel approach for the study of human lymphopoiesis and a method for gene replacement therapy in humans with immunodeficiencies.

Allogeneic hematopoietic stem cell (HSC) transplantation is currently the only established therapy for SCID; however, delayed immune recovery and risk of graft-vs-host disease present significant risks. Treatment by retroviral-based gene therapy has been successfully demonstrated for X-linked SCID. However, severe adverse effects of insertional mutagenesis have been observed with retroviral gene therapy. Self-inactivating lentiviral vectors have been used effectively in recent clinical trials, but long-term follow-up is needed to thoroughly address safety concerns.

Provided herein is an alternative therapeutic strategy in which patient-specific induced pluripotent stem cells (iPSCs) are derived, and disease-causing mutations are corrected by gene replacement using a CRISPR-Cas9 complex. These corrected iPSCs could optionally be differentiated into hematopoietic progenitors for transplantation into patients to treat the disease (Hanna et al., "Treatment of sickle cell anemia mouse model with iPS cells generated from autologous skin," *Science* 318: 1920-1923 (2007)). As shown herein, differentiation of JAK3-deficient human T cells is blocked at an early developmental stage. Also demonstrated is that correction of the human JAK3 mutation by CRISPR/Cas9 enhanced gene replacement restores the differentiation potential of early T cell progenitors. These corrected progenitors are capable of producing NK cells and mature T cell populations expressing a broad repertoire of T-cell antigen receptors (TCR). These studies establish a powerful system for determining the mechanism of immunodeficiency in human SCID patients and for testing pharmacological and genetic therapies for the disorder.

Patient Information

The male patient was enrolled in an Institutional Review Board-approved study in accordance with the Declaration of Helsinki. The family history was negative for immune deficiencies. For the first 8 months of age he had poor weight gain, diarrhea, and recurrent bronchiolitis requiring frequent hospitalization. He was admitted to the hospital at 8 months of age with severe respiratory distress and oral thrush. Bronchoscopy with bronchial alveolar lavage demonstrated bacterial (*pseudomonas*, H flu, *S. pneumonia*) and viral organisms (respiratory syncytial virus). Immunologic evaluations demonstrated severe hypogammaglobulinemia, with an IgE<3, IgA<4, IgG=29, IgM=26. Immune phenotyping of peripheral blood demonstrated complete absence of CD3+ T cells and NK cells, though B cells were present (absolute B cell count=875). Mitogen studies demonstrated a complete lack of response to concanavalin A, poke weed mitogen and phytohemagglutinin A. The diagnosis of SCID was confirmed by genetic testing, with a homozygous C>T nucleotide substitution in exon 14 of the JAK3 gene, resulting in the replacement of an arginine codon (CGA) with a stop codon (TGA) at amino acid position 613. This is the first report linking this JAK3 variant (rs149316157) to a clinical case of SCID. The patient underwent a reduced intensity conditioning matched unrelated bone marrow transplant, and is doing well now two years off therapy with complete immune reconstitution.

Human iPSC Reprogramming and Characterization

For iPSC induction, $5 \times 10^4$ primary keratinocytes were seeded into one well of a 6-well plate. On the following day, keratinocytes were transduced with 1 mL of virus supernatant and 1 mL of human keratinocyte medium containing polybrene at a final concentration of 4 µg/mL. The keratinocytes were spinfected at 800×g for 45 minutes (day 1). The transduction procedure was repeated again the next day. On day 3, cells were changed to fresh human keratinocyte medium and cultured for two more days. On day 5, the keratinocytes were trypsinized and transferred to a 10 cm dish pre-seeded with mitomycin C-treated murine embryonic fibroblasts (MEFs) and cultured in human keratinocyte medium. On day 7, cells were changed to human ES medium and continuously cultured in the same dish for 3-4 weeks. ES medium was changed daily. Potential iPSC colonies were visible after 2-3 weeks. These colonies were individually picked and expanded on MEFs for analysis. To remove the integrated lentiviral and polycistronic sequences, iPSCs were infected with a Cre-expressing adenovirus (rAd-Cre-IE). Individual colonies were picked and Cre-mediated removal of floxed sequences was verified by PCR using the primers gctaattcactcccaaagaagacaag (SEQ ID NO: 5) and cttcagcaagccgagtcctg (SEQ ID NO: 6).

Generation of CD34+ Cells and T Cells with OP9 Co-Culture

The procedure was described previously (Chang et al., "Broad T-cell receptor repertoire in T-lymphocytes derived from human induced pluripotent stem cells," PloS one 9, e97335 (2014)). This method was used with the following modifications. Cultures of hiPSCs in one well of a 6 well plate were treated as described by Ohnuki et al (Ohnuki M, "Generation and characterization of human induced pluripotent stem cells. *Curr Protoc Stem Cell Biol* Chapter 4: Unit 4A 2 (2009)) with CTK solution to make small cell clumps. Cell clumps were then transferred to a 10 cm plate that was pre-seeded with 2-day old OP9 cells in α-MEM-based medium containing 10% FBS, 1× penicillin/streptomycin and 100 µM mono-thioglycerol. The medium was changed every other day, and cells were cultured for 18 days without splitting. After 18 days of co-culture, cells were harvested by treating with dissociation solution (0.15% collagenase IV and 0.015% hyaluronidase in α-MEM medium) for about 30 minutes and followed by 0.25% trypsin for another 30 minutes. CD34+ cells were then purified on anti-CD34+ magnetic beads (MicroBead Kit; Miltenyi Biotec, Bergisch Gladbach, Germany). For T cell differentiation, these CD34+ cells were plated onto OP9-DL4 cells and cultured with α-MEM medium containing 20% FBS, 5 ng/mL hFlt3-L, 5 ng/mL hIL-7, and 10 ng/mL hSCF. The medium was changed every other day, and cells were transferred to new OP9-DL4 plates every 4 days.

T Cell Stimulation

In vitro derived T cells from hiPSCs were stimulated by incubation with CD3/28 beads (Invitrogen, Carlsbad, Calif.) according to the manufacturers' protocol for 3 days prior to analysis by flow cytometry, as previously described (Chang et al., 2014).

Flow Cytometry

Cells were harvested and washed before analysis with an LSRFortessa cell analyzer (BD Bioscience, San Jose, Calif.). For cell surface staining, propidium iodide (PI, Sigma-Aldrich, St. Louis, Mo.) was used to exclude dead cells. For apoptosis assay, harvested cells were first stained with cell surface antibodies for 30 min. After washing once with 1×PBS, the cells were resuspended in 100 µL of Annexin Binding Buffer (Invitrogen, Carlsbad, Calif.) containing Annexin V-647 (Invitrogen, Carlsbad, Calif.) and PI and incubated for 15 min before adding 400 µL of Annexin Binding Buffer with PI. Antibodies were obtained from BD Biosciences unless otherwise indicated: CD3 (Percp-Cy5-5, clone UCHT1), CD4 (PE-Cy7, clone SK3), CD7 (APC, BV510, clone M-T701), CD8 (APC-Cy7, clone SK1), CD16 (PE, clone B73.1), CD25 (FITC, clone 2A3), CD34 (PE-Cy7, clone WM59), CD43 (PE, clone 1G10), CD56-PE (clone MY31), CD69 (FITC, clone L78), NKG2D-PE (clone 1D11), TCR-αβ (FITC, PE, clone T10B9.1A-31), TCR-Vδ1-FITC (Fisher Scientific, Pittsburgh, Pa., Clone TS8.2), TCR-Vδ2-PE (clone B6), TCRVγ9-FITC (clone B3), TNF-α-PE-Cy7 (clone MAB11), Beta Mark TCR Repertoire Kit (Beckman Coulter, Atlanta, Ga.).

Vector Construction

The polycistronic OSKM vector was previously described (Chang et al., "Polycistronic lentiviral vector for "hit and run" reprogramming of adult skin fibroblasts to induced pluripotent stem cells," *Stem cells* 27: 1042-1049 (2009)). The Lenti-hDL4-mCherry plasmid was constructed by cloning a PCR-amplified human DL4 cDNA (Open Biosystems, LaFayette, Colo.), an IRES fragment (Open Biosystems) and mCherry cDNA into a lentiviral vector (pDL171) which contains the EFla promoter. PCR reactions were performed using PrimeStar polymerase (Takara, Mountain View).

To construct CRISPR plasmids, gRNA oligos were designed and introduced into pX330 and pX335 plasmids following the Zhang lab protocol (Addgene, Cambridge, Mass.). To construct the JAK3 repair plasmid, wild type human genomic DNA was PCR amplified using JAK3 primer sets (5' arm: gtcgacgtcgacgctcagtgaagctgaagtat-tccttctgcttcacagggcgaccactac (SEQ ID NO: 7) and att-taaatcctcccctcgaacccttaccaaactcctatgcatactacag (SEQ ID NO:8); 3' arm: ttaattaattaattagcattttaggttcaggttgt-gagaacactagaagagaacaagtca (SEQ ID NO: 9) and gtatacgtatacgcatacctggagaggggacaaggtcttgagatgcgagggt (SEQ ID NO: 10). After digesting with enzymes (5' arm: SalI and SwaI; 3' arm: PacI and BstZ17I), the PCR products were cloned into a plasmid containing a LoxP-PGK-Neo-LoxP fragment. All of the oligos used in this study were synthesized by Integrated DNA Technologies (IDT, Coralville, Iowa). To construct the BCL2 lentiviral plasmid, a primer set (forward: agccaccttaattaagccaccatggcgcacgctgg-gagaacggggtacgata (SEQ ID NO: 11) and reverse: taacagagagaagttcgtggctccggatcccttgtggcccaga-taggcacccagggtgat (SEQ ID NO: 12)) was used to amplify the human BCL2 cDNA (Open Biosystems) fragment. The product was linked with GFP through a 2A sequence by PCR and cloned into the pDL171 vector. gRNA-F1 caccGTG AGA TAC AGA TAC AGA CA (SEQ ID NO: 13) gRNA-R1 aaacTGT CTG TAT CTG TAT CTC AC (SEQ ID NO: 14) gRNA-F2 caccgAAT GAT TTG CCT GGA ATG CC (SEQ ID NO: 14) gRNA-R2 aaacGGC ATT CCA GGC AAA TCA TTc (SEQ ID NO: 15) gRNA-F3 caccgCAG CCT AGG CAA AGG CCT GC (SEQ ID NO: 16) gRNA-R3 aaacGCA GGC CTT TGC CTA GGC TGc (SEQ ID NO: 17) gRNA-F4 caccgTGC CAA CAG AAC TGC CTG AT (SEQ ID NO: 18) gRNA-R4 aaacATC AGG CAG TTC TGT TGG Cac (SEQ ID NO: 19) gRNA-F5 caccGAC CAG GGT GCA AGT GTG GA (SEQ ID NO: 20) gRNA-R5 aaacTCC ACA CTT GCA CCC TGG TC (SEQ ID NO: 21) gRNA-F6 caccGCT CCT CAG CCT GGC ATT CA (SEQ ID NO: 22) gRNA-R6 aaacTGA ATG CCA GGC TGA GGA GC (SEQ ID NO: 23)

Cell Culture

IPSCs were cultured on mitomycin C-treated MEFs derived from E14.5 CF-1 embryos in ES cell media consisting of DMEM F-12 supplemented with 1× non-essential amino acids, 1× penicillin-streptomycin, 1× L-glutamine (all from Mediatech, Corning, N.Y.), 20% KnockOut Serum Replacement (Invitrogen), 2-βME (Sigma) and 5-10 ng/mL bFGF (Invitrogen). Human primary keratinocytes were cultured in DermaLife K Medium Complete Kit (LifeLine Cell Technology, Frederick, Md.). OP9 cells were purchased from ATCC and grown in α-MEM medium with 20% FBS and penicillin-streptomycin. OP9-DL4 cells were established by transducing OP9 cells with a lentivirus containing hDL4 and mCherry.

Virus Production

For preparation of lentivirus, 10 μg of the lentiviral vector, 2.5 μg of the envelope plasmid (pMDG), and 7.5 μg of the packaging plasmid (pCMBVdR8.9.1) were co-transfected into 5×106 293T cells by Fugene 6 (Roche, Nutley, N.J. or Promega, Madison, Wis.). Virus-containing supernatant was collected 2 days after transfection and passed through a 0.45 μm filter.

Gene Targeting

IPSCs were treated with 0.25% trypsin for 5 minutes to generate single cell suspensions. After washing twice with 1×PBS, 1 to 2 million cells were mixed with 5 μg of JAK3 repair plasmid and 5 μg of pX330-JAK3 or pX335-JAK3 plasmids for Nucleofection (Human Stem Cell Nucleofector Kit, program A-023, Lonza, Alpharetta, Ga.) and plating onto MEFs. Two to four days later, hES medium containing 30 μg/mL of G418 was added to the plates to select for drug resistant colonies. The colonies were picked 3 to 4 weeks later and expanded for genomic DNA extraction. For PCR genotyping, a 5' primer set (tgctaaagcgcatgctccagact (SEQ ID NO: 24) and gtcttcatctcagggtcggct (SEQ ID NO: 25) and a 3' primer set (cctctctgtgcattatggcag (SEQ ID NO: 26) and gccttctatcgccttcttg (SEQ ID NO: 27)) were used. To remove the Neo selection marker, hiPSCs were infected with a Cre-expressing adenovirus (rAd-Cre-IE).

RT-PCR

Total RNA was isolated from in-vitro derived cells with Trizol reagent (Invitrogen, Carlsbad, Calif.). cDNA was synthesized with 0.5 to 2 μg of total RNA using Superscript First-strand Synthesis System (Invitrogen) according to the manufacturer's instructions. SYBR Green PCR Master Mix (Life Technologies, Carlsbad, Calif.) was used for qPCR according to the manufacturer's instructions. Primer sets used for qPCR are GAPDH (F: actcctccacctttgacgct (SEQ ID NO: 28), R: tcccctcttcaagggtctacatg (SEQ ID NO: 29)); PU.1 (F: gtgcaaaatggaagggtttc (SEQ ID NO: 30), R: ggagctccgtgaagttgttc (SEQ ID NO: 31)); GATA3 (F: tgtttcctttcactggccaca (SEQ ID NO: 32), R: aacggcaactggt-gaacggta (SEQ ID NO: 33)); BCL11B (F: ggcgatgccagaata-gatgccg (SEQ ID NO: 34), R: ccaggccacttggctcctctatctccaga (SEQ ID NO: 35)); RAG1 (F: ccttactgttgagactgcaatatcc (SEQ ID NO: 36), R: ctgaagtcccagtatatacttcacac (SEQ ID NO: 37)); RAG2 (F: cccagaagcagtaataatcatcgag (SEQ ID NO: 38), R: atgtgggatgtagtagatcttgc (SEQ ID NO: 39)); pTa (F: gggtcttacctcagcagttac (SEQ ID NO: 40), R: cct-cacacagtgtgacgcag (SEQ ID NO: 41)); BCL2 (F: gact-gagtacctgaaccggc (SEQ ID NO: 42), R: gggccaaact-gagcagagtc (SEQ ID NO: 43)); BAX (F: aagaccagggtggttgggac (SEQ ID NO: 44), R: gtaagaaaaatgcc-cacgtc (SEQ ID NO: 45)); and JAK3 (F: agtcagacgtctg-gagcttc (SEQ ID NO: 46), R: gtgagcagtgaaggcatgagtc (SEQ ID NO: 47)). All values were normalized relative to GAPDH expression.

Whole Genome Sequencing and Analysis

DNA from iPSCs was sheared using a Covaris S2 Focused-ultrasonicator: 130 μL samples in microTUBEs were subjected to two 40-second cycles of 10% Duty Cycle, Intensity of 4, and 200 Cycles per Burst in Frequency Sweeping Mode. DNA Chip (DNA 1000 Kit; Agilent Technologies, Santa Clara, Calif.) analysis using an Agilent 2100 Bioanalyzer indicated an average fragment size of 400 bp. Library preparation was performed using an NEBNext Ultra DNA Library Prep Kit for Illumina (NEB #E7370), and the final library concentration was determined by qPCR using a KAPA Illumina Library Quantification Kit (KK4835; KAPA Biosystems, Wilmington, Mass.) and an Applied Biosystems ViiA 7 Real-Time PCR System (Life Technologies). Sequencing clusters were produced on the flow cell using an Illumina TruSeq PE Cluster Kit v3-cBot-HS (PE-401-3001) and an Illumina cBot. WGS was performed using an Illumina TruSeq SBS Kit v3-HS-200 cycles (FC-401-3001) and an Illumina HiSeq 2500 upgrade to generate 2×100 single-index paired-end reads for bioinformatic analysis. Probable off-target sites were identified by aligning the CRISPR/Cas9 guide sequences to the hg19 reference genome using EMBOSS fuzznuc software (v6.6.0.0) (Rice et al., "EMBOSS: the European Molecular Biology Open Software Suite," *Trends in Genetics*: TIG 16: 276-277 (2000)) and allowing for a maximum of three mismatches; 1193 sites were predicted for the first guide sequence (GTGAGATA-CAGATACAGACA) (SEQ ID NO: 48) and 257 sites for the second guide sequence (AATGATTTGCCTGGAATGCC) (SEQ ID NO: 49). All of the reads from the WGS for each sample were mapped to the hg19 reference genome using the BWA (v0.7.5a) mem algorithm (Li and Durbin, "Fast and accurate long-read alignment with Burrows-Wheeler transform," *Bioinformatics* 26: 589-595 (2010)) and duplicate reads were removed using Picard-tools (v1.100) (http://picard.sourceforge.net). Local realignment and base quality re-calibration were performed using GATK (v2.7-2) (McKenna et al., "The Genome Analysis Toolkit: a MapReduce framework for analyzing next-generation DNA sequencing data," Genome research 20: 1297-1303 (2010)). Both SNVs and indels were called using the GATK HaplotypeCaller. Additionally, SNVs and indels were separately re-calibrated as described in GATK Best Practices and quality filters were applied. The variants from the reference genome that were common to all four iPSC samples were excluded from CRISPR/Cas9 off-target analysis. The non-excluded variants were screened using Bedtools (v2.17.0) (Quinlan and Hall, "BEDTools: a flexible suite of utilities for comparing genomic features," Bioinformatics 26: 841-842 (2010)) to determine if they fell within the probable off-target sites. The analysis shows that none of these variants reside in the off-target sites and suggests these mutations were randomly accumulated. All of the functional variants (excluded and non-excluded) with a low allele frequency (<1%, dbSNP 138) were then annotated using the ANNOVAR software package and screened for known associations with diseases in HGMD and ClinVar (v20140902); additionally, all of the hits with a high CADD score (CADD>=20) were also screened for associations with complex diseases using the GWAS Catalog and COSMIC (v70). No validated disease-associated variants were identified in the databases queried. Of particular interest, the JAK3 C1837T (p.R613X) mutation was also not validated to associate with a disease, though the SNP (rs149316157) is predicted to be significantly deleterius, with a GERP score of 3.85 and a CADD score (CADD phred-like score) of 38. Therefore, the JAK3 C1837T variant was associated for the first time with a clinical case of SCID.

Accession Codes

The WGS data can be accessed at the NCBI SRA database with the accession number SRP056149.

Figure 1B:
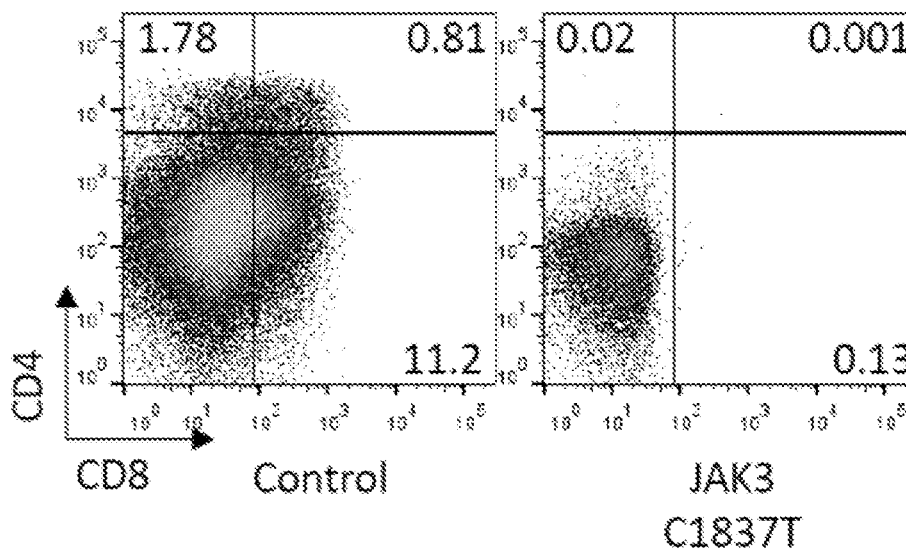
Figure 1C:
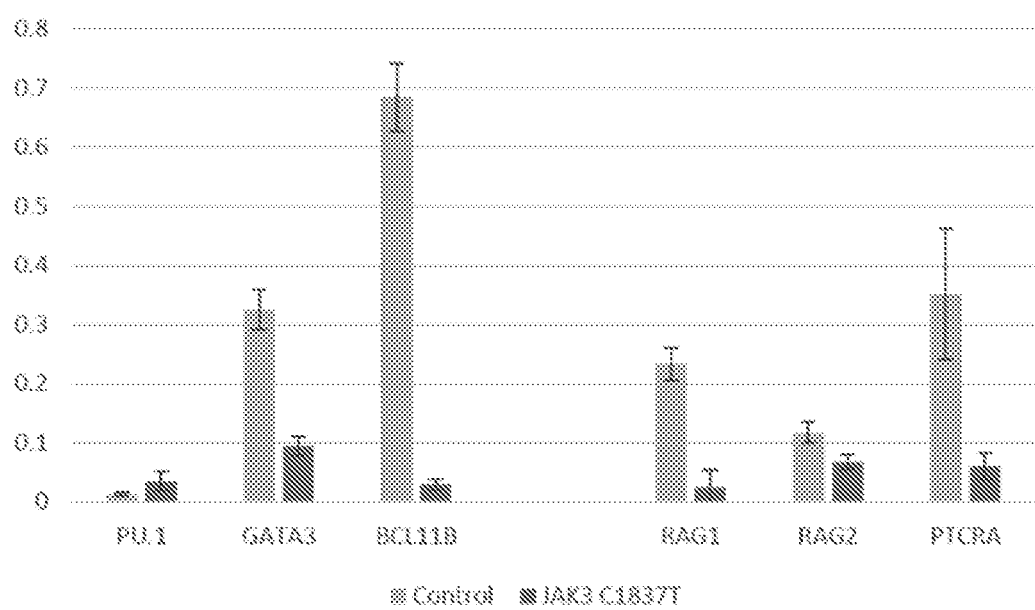
Figure 2A:
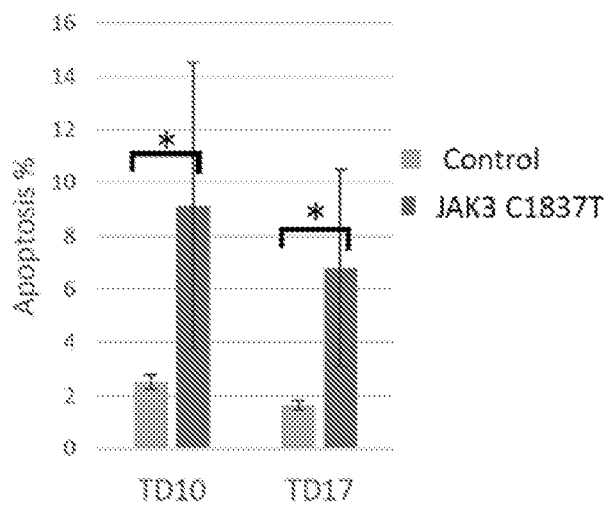
FIGS. 2A-2C show that BCL2 partially rescues T cell developmental defects in JAK3-deficient, in-vitro derived cells.
Figure 2B:
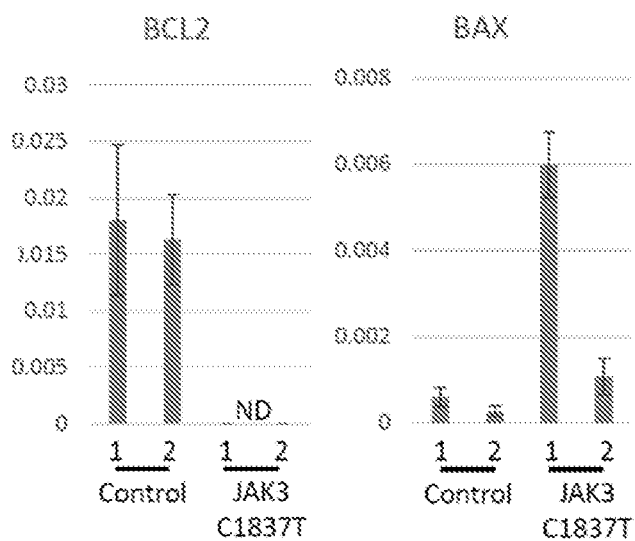
Figure 2C:
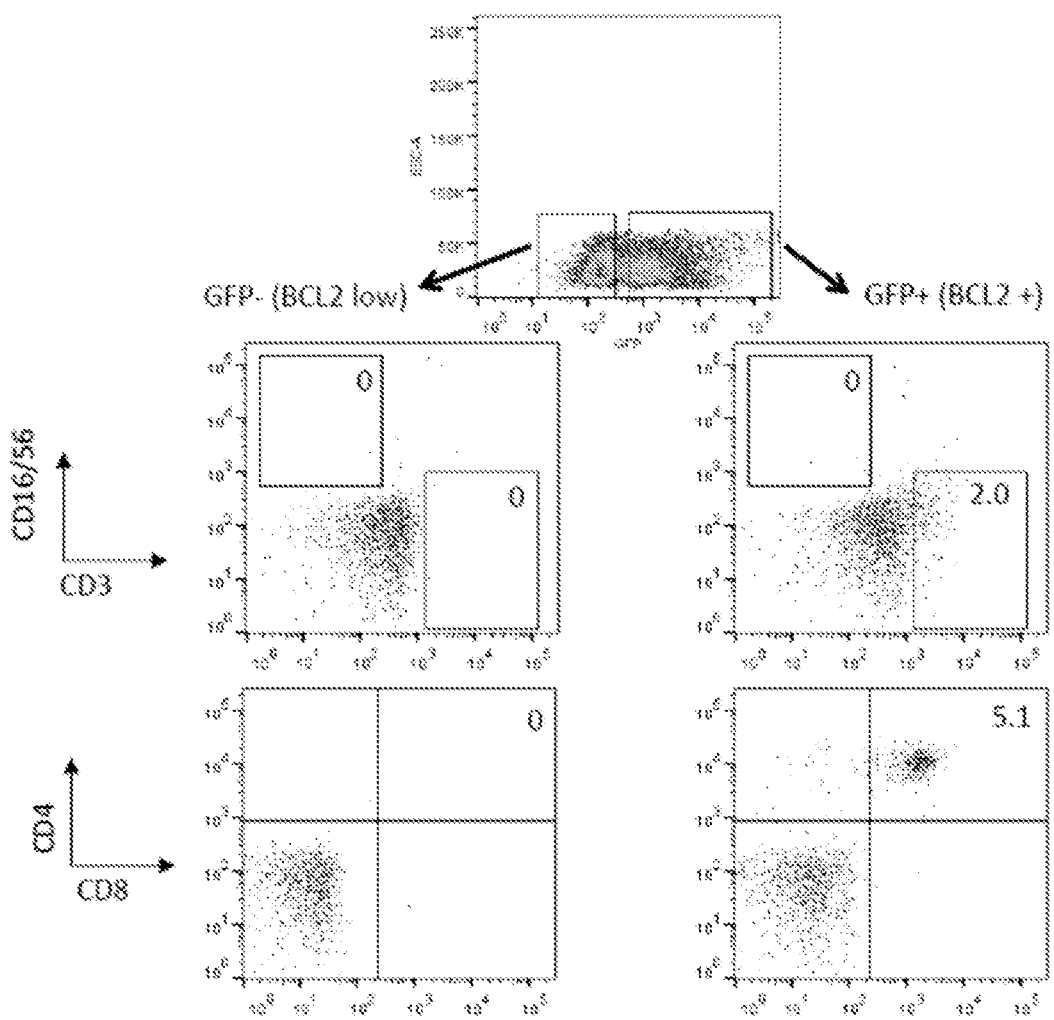
Figure 4A:
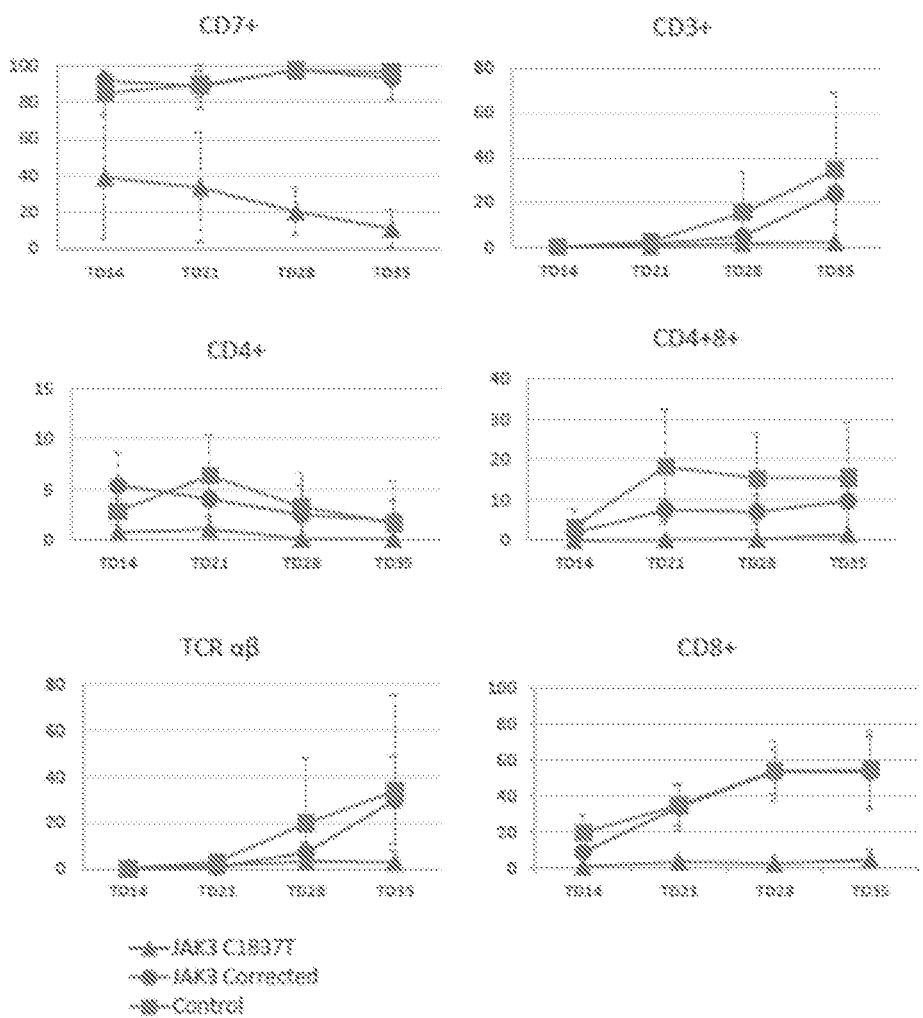
FIGS. 4A-4C show in vitro differentiation of JAK3 corrected patient iPSCs produces T cells with phenotypic and functional characteristics of mature T cells.

JAK3-Deficient Human T Cells Express Low Levels of BCL2 and Die at an Early Developmental Stage IPSCs were generated from skin keratinocytes (Chang et al., 2009) of a SCID patient homozygous for a C>T nucleotide substitution in exon 14 of the JAK3 gene. This mutation replaces a CGA codon (arginine at 613) with a TGA stop codon (p.R613X). As described above, the four-month-old patient presented with a T−B+NK− clinical phenotype. To determine whether this SCID phenotype can be recapitulated in vitro, differentiation of patient-specific iPSCs to T lymphocytes using a two-step OP9 and OP9-DL4 system (Chang et al., 2014) was attempted. JAK3-deficient iPSCs grew at a rate comparable to control iPSCs derived from healthy donors, and these iPSCs efficiently differentiated into CD34+ hematopoietic progenitors (HPs) on OP9 stromal cell monolayers. However, when the JAK3-deficient, iPSC-derived CD34+ HPs were plated on OP9-DL4 stromal monolayers, T-cell differentiation was absent compared to controls (FIG. 1). No CD3+ T cells or CD3-CD16+CD56+ NK cells were observed (FIG. 1A), and no CD4+CD8+ double positive (DP), CD4+ single positive (SP), or CD8+ single positive (SP) T cells were detected (FIG. 1B). Jak3 knockout (KO) mice have a small thymus due to a block in thymocyte differentiation at the CD4−CD8− double negative (DN) stage prior to productive TCR rearrangement. To further understand the developmental defects resulting from a JAK3 mutation in humans, T lineage commitment and maturation of JAK3-deficient cells compared to normal JAK3 WT controls was assayed. IPSC-derived CD34+ cells were plated on OP9-DL4 monolayers, and cells were harvested and analyzed for lymphocyte markers at T-cell induction day (TD) 14, 21, 28 and 35 (FIG. 4A). In normal controls, 1.2×107 CD7+ cells (84% of cells counted in the lymphoid gate) were generated at TD14 from 1-2×10⁶ CD34+ cells. T cell markers CD4, CD8, CD3 and TCR αβ were sequentially detected upon T cell maturation. At TD35, more than 50% of the population was CD8 SP cells. In JAK3-deficient cells, only 4.5×104 CD7+ cells (38.9% of cells counted in lymphoid gate) were generated at TD14 from 1-2×10⁶ CD34+ cells. The number of CD7+ cells decreased during extended culture and T cell markers CD3, CD4, CD8 and TCR αβ were not significantly expressed. During the transition through early T cell progenitors (ETPs), the CD4−CD8− (DN) to CD4+CD8+ (DP) stages are directed by precise activation and repression of specific transcription factors. In control cells, the silencing of PU.1 and induction of GATA3 and BCL11B (FIG. 1C) suggest that these cells proceed to the onset of T lineage commitment (DN2 to DN3) followed by TCR rearrangement. In contrast, in JAK3-deficient cells PU.1 accumulates and GATA3 and BCL11B levels are reduced (FIG. 1C). These data suggest that human JAK3-deficient cells arrest before or at the DN2 stage, which is similar to the stage at which T cells die in Jak3 KO mice. Interestingly, human JAK3-deficient cells may express sufficient RAG1, RAG2 and PTCRA (FIG. 1C) to perform TCR rearrangement, but the cells do not survive long enough to proceed to this important developmental stage. These profound defects in lymphocyte development of JAK3-deficient cells can be explained by the absence of IL-7 signaling which plays an important role in lymphoid progenitor survival and differentiation. IL-7/JAK3 signaling maintains thymocyte homeostasis by regulating the BCL2 family of apoptotic regulators. Thymocytes and peripheral T cells from Jak3 KO mice have a high apoptotic index in part through selectively elevating BAX, a pro-apoptotic factor, and by reducing expression of BCL2, an anti-apoptotic factor. Similarly, in these studies, an increase in apoptosis of in vitro-derived human JAK3-deficient cells compared to controls at TD10 (9% to 2.2%) and TD17 (7% to 1.9%) (FIG. 2A). Consistent with this phenotype, BAX levels were increased and BCL2 levels were reduced in JAK3-deficient cells compared to controls (FIG. 2B). Forced expression of Bcl2 rescues T, but not B or NK cell development in γc-deficient mice (Kondo et al., Immunity 7: 155-162 (1997)). Transplantation of Jak3 KO mice with Bcl2-expressing Jak3 KO bone marrow cells also improves peripheral T cell numbers (Wen et al., Molecular and cellular biology 21: 678-689 (2001)). To determine whether overexpression of BCL2 will rescue T cell developmental defects of human JAK3-deficient cells, in vitro-derived, JAK3-deficient CD34+ cells were transduced with a lentivirus containing a BCL2-2A-GFP polycistron driven by EFla promoter. After transduction, CD34+ cells were plated on OP9-DL4 monolayers and assayed for NK and T cell markers at TD 28. No CD3−CD16+CD56+ NK cells were found in GFP− (JAK3−; BCL2 low) or GFP+ cells (JAK3−; BCL2+) (FIG. 2C). These findings suggest that BCL2 released the blockage at the DN stage in JAK3-deficient cells. Interestingly, a second developmental arrest was evident at the DP stage; no further differentiation of CD8+CD4+ DP positive cells was observed in GFP+ cells (FIG. 2C). In summary, the studies described above demonstrate that human SCID phenotypes can be recapitulated in vitro with patient-derived iPSCs. JAK3 deficiency results in proliferative defects in DN thymocytes. Forced expression of BCL2 enhances survival of DN cells, which further differentiate into DP thymocytes. Nevertheless, DP thymocytes fail to mature to SP T cells, and this defect may result from the absence of IL7/JAK3 signaling.

Figures 3C, 3D:
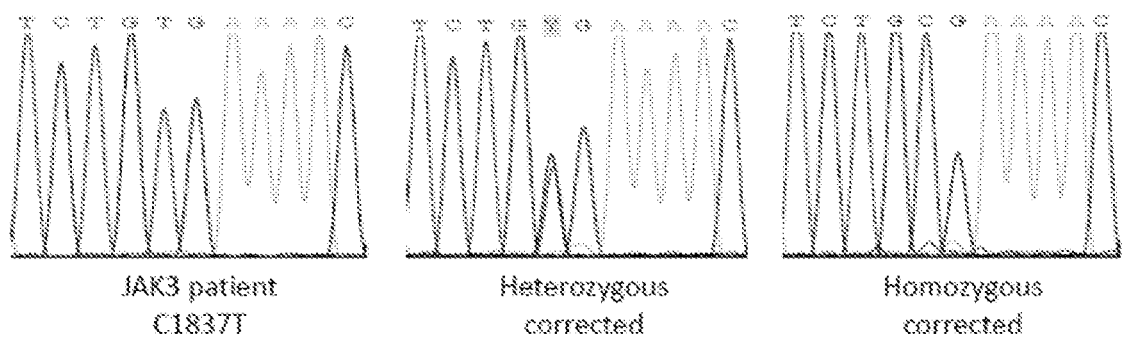

Correction of the JAK3 Deficiency in SCID hiPSCs by CRISPR/Cas9 Enhanced Gene Replacement To determine whether normal T cell development can be restored in JAK3-deficient SCID patient cells, the JAK3 mutation was corrected in iPSCs by CRISPR/Cas9 enhanced gene replacement. Six guide RNAs within introns upstream and downstream of exon 14 were designed to target wtCas9 or nCas9 near the C1837T mutation, and a correction template was used for gene replacement (FIG. 3A). IPSCs were nucleofected with two plasmids expressing the D10A Cas9 nickase and paired guide RNAs or a single plasmid expressing wild-type Cas9 and a single guide RNA. Cells were grown in medium containing G418 for 2 weeks post nucleofection. Individual colonies were picked, expanded, and genotyped by PCR (FIG. 3B Top). The efficiency of CRISPR/Cas9-mediated JAK3 gene correction is shown in FIG. 3C. Three clones from WT Cas9+gRNA #1, 3 clones from WT Cas9+gRNA #2 and 6 clones from Cas9 nickase+ paired gRNAs #1 and #2 were further verified by Sanger sequencing. In 12 sequenced clones, 2 homozygous corrected clones (1 clone from Cas9 nickase+paired gRNA #1 and #2, and 1 clone from WT Cas9+gRNA #1) and 10 heterozygous corrected clones were identified (FIG. 3D). Restoration of JAK3 gene expression was demonstrated by RT-PCR (JAK3 mRNA) (FIG. 3B; lower left panel) and western blot (JAK3 protein) (FIG. 3B; lower right).

Specificity of CRISPR/Cas9 Directed JAK3 Correction

The potential for off-target, CRISPR/Cas9 directed genome modifications raises some concerns about the use of this approach for therapy in humans. In cancer cell lines, relatively high levels of off-target mutagenesis by Cas9-gRNAs have been described. To determine the specificity of CRISPR/Cas9 directed JAK3 correction in human SCID iPSCs, Whole genome sequencing was performed before and after gene replacement. The genomes of two heterozygous and one homozygous corrected clones were sequenced. The two heterozygous clones were corrected with gRNA #2+wild type Cas9, and the homozygous clone was corrected with gRNA #1+gRNA #2+nickase Cas9 (D10A). The 20-base CRISPR guide sequences were mapped to the human reference genome, allowing up to 3 mismatches in order to identify possible off-target sites. These sites were then analyzed for variations in the iPSC samples following CRISPR/Cas9 directed gene replacement. WGS analysis of one homozygous and two heterozygous corrected iPSC lines demonstrated that no mutations (SNVs nor indels) were introduced into the predicted off-target sites, suggesting a strong specificity for the CRISPR/Cas9 directed gene replacement.

Restoration of T Cell Development after CRISPR/Cas9 Directed JAK3 Correction

Figure 4B:
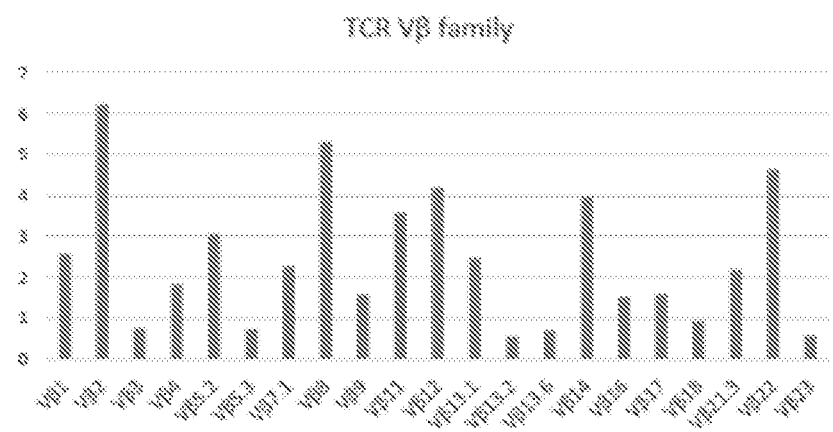
Figure 4C:
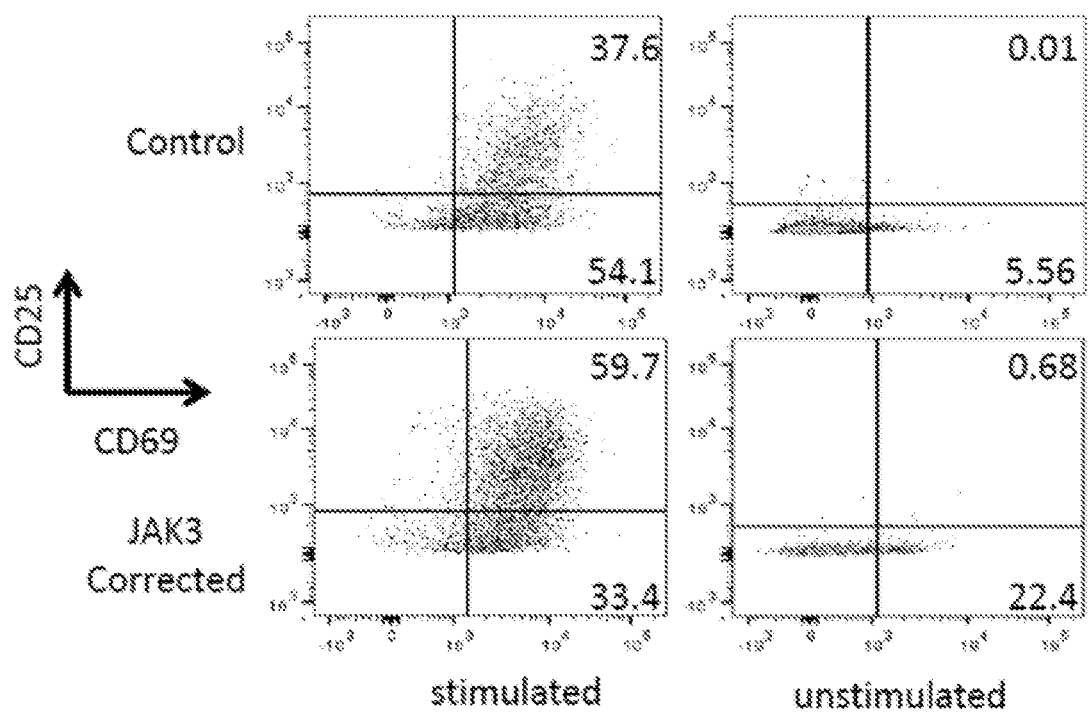

To determine whether T cell development is restored after JAK3 gene correction, T cell lineage commitment and maturation were assayed. T cell differentiation sequentially passes through intermediates observed in vivo: CD34+ CD7+ T/NK committed stage; CD7+CD4+CD8− immature, SP stage; CD4+CD8+ DP stage; and finally, CD3+CD8+ TCRαβ mature stage. Mature T cells are polyclonal, proliferate, and secrete cytokines in response to mitogens. Therefore, JAK3 corrected hiPSCs were differentiated into hematopoietic progenitors on OP9 monolayers, and CD34+ cells were positively selected on anti-CD34 magnetic beads. These cells were plated on OP9-DL4 monolayers, and nonadherent cells were analyzed for lymphocyte markers at TD14, 21, 28 and 35 (FIG. 4). Similar to control cells, 1-2×106 CD34+ JAK3 corrected cells differentiated into 4.7×106 CD7+ cells (91% of cells counted in lymphoid gate) at TD14. After further differentiation to TD21, TD28 and TD35, T cell maturation markers CD3, CD4, CD8 and TCR αβ were abundantly observed (FIG. 4A). To determine whether TCR rearrangement is reestablished in JAK3-corrected T cells, TCR Vβ typing was performed by flow cytometry and summarized in FIG. 4B. JAK3-corrected T cells expressed all the Vβ segments that we tested (19 of 25); therefore, a broad TCR repertoire was restored. Finally, the integrity of the TCR signaling pathway, a surrogate of T cell function, in JAK3-corrected T cells, was examined by measuring cell surface activation markers following anti-CD3/CD28 stimulation. On Day 3 post-stimulation, the percentage of CD3+CD25+CD69+ T cells increased from 0.68% to 59.7% in JAK3-corrected T cells similar to the increase observed in control cells (0.01% to 37.6%) (FIG. 4C). These data and results described above demonstrate that correction of the JAK3 C1837T (p.R613X) mutation by CRISPR/Cas9 enhanced gene replacement in an in vitro iPSC model system restores normal T cell development with the capacity to produce functional, mature T cell populations with a broad TCR repertoire.

In humans, the phenotype of lymphocytes in the peripheral blood of SCID patients has been well described, but studies on critical steps of lymphoid commitment and thymocyte development have been difficult to perform. Access to bone marrow and thymocyte samples from untreated patients with SCID is challenging since these conditions are rare and infants typically present with life-threatening infections requiring urgent HSC transplantation to survive. The strategy described herein for studying human SCID bypasses these restrictions; large numbers of hematopoietic progenitors can be produced from patient specific iPSCs in vitro, and the mechanisms responsible for immunodeficiency can be precisely determined. Demonstrated herein is that T cell development in human JAK3-deficient SCID is completely blocked before or at the CD4−CD8− (DN2) stage. Interestingly, forced expression of BCL2 enhances survival of DN cells, which further differentiate into DP thymocytes. However, DP thymocytes fail to mature to SP T cells, and this defect may result from the absence of IL7/JAK3 signaling. It is also demonstrated that correction of the human JAK3 mutation by CRISPR/Cas9 enhanced gene replacement restores the differentiation potential of early T cell progenitors. Corrected progenitors are capable of producing NK cells and mature T cell populations expressing a broad TCR repertoire. Whole-genome sequencing analysis of one homozygous and two heterozygous corrected iPSC lines demonstrates that no mutations (SNVs nor indels) are introduced into the predicted off-target sites, suggesting a strong specificity for the CRISPR/Cas9 directed gene replacement.

Figure 5:
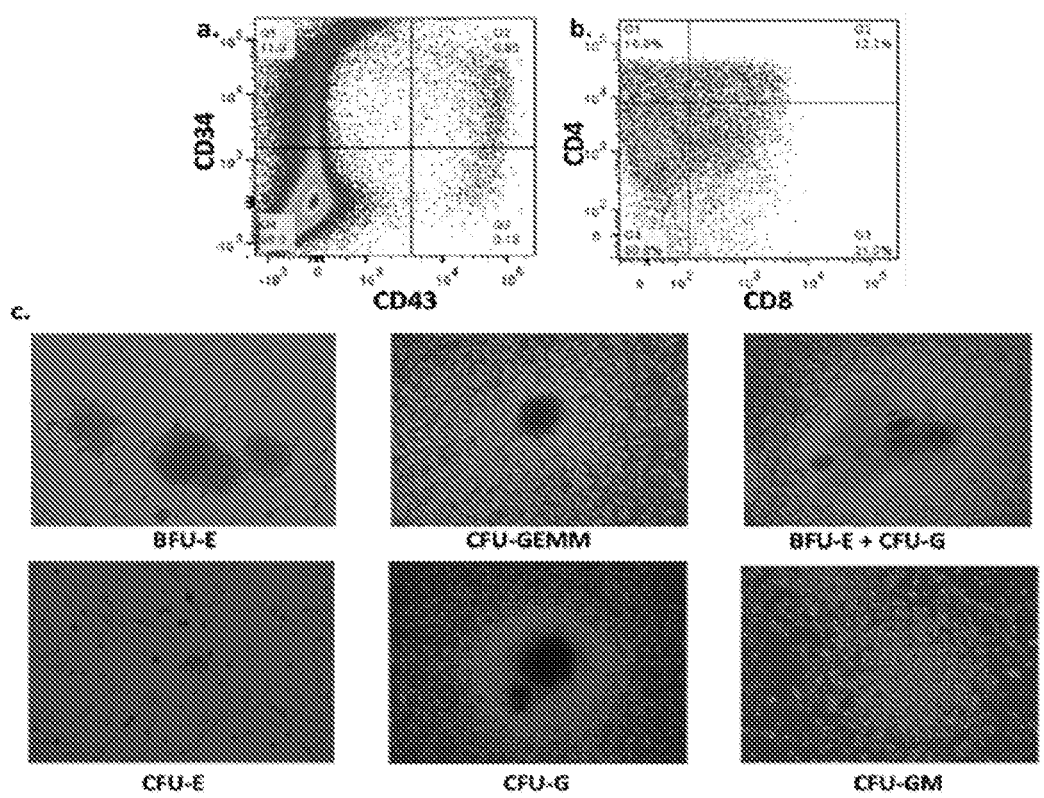
FIGS. 5A-5C show in vitro generation of CD34+ HSCs from hiPSCs by co-culture with human bone marrow stromal cells (hMSC). Human iPSCs were cultured on hMSCs for 18 days before analysis for hematopoietic markers, CD34 and CD43 (Figure A). CD34+ cells were purified on beads and differentiated into T cells (Figure B), erythroid and myeloid cells (Figure C). To generate T cells, purified CD34+ cells were plated on OP9-DL4 cells for 3 to 4 weeks. For the CFC assay to generate myeloid and erythroid cells, purified CD34+ cells were plated in MethoCult H4434 Classic medium according to the manufacturer's protocol. These data demonstrate that hiPSC can be efficiently differentiated into multipotent HSC after co-culture on hMSC.
Figure 6:
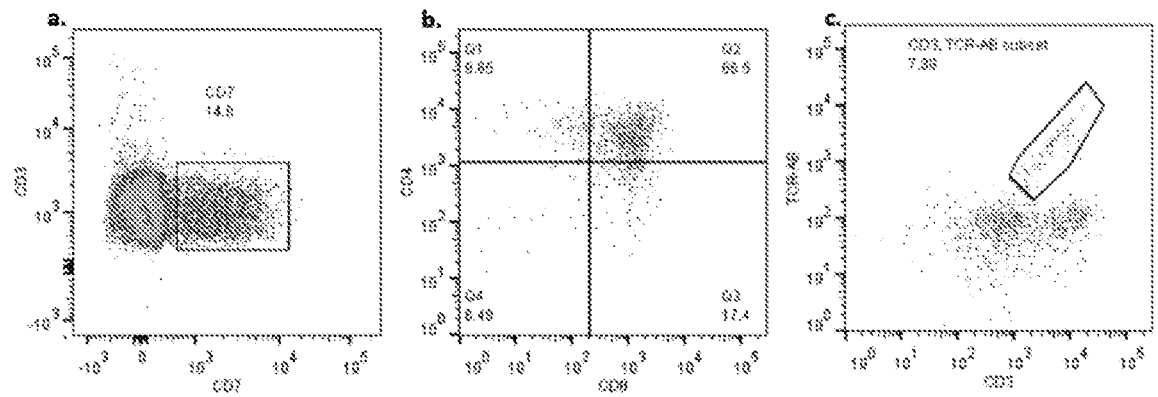
FIG. 6A-6C show in vitro generation of T cells by culturing hiPSC derived CD34+ cells with hMSC-DL4. To generate CD7+T progenitor cells, hiPSC derived CD34+ cells were co-cultured on hMSC-DL4 for 3 to 4 weeks (FIG. 6A). When CD7+ cells from FIG. 6A were purified on magnetic beads and co-cultured on OP9-DL4, fully mature CD4+/CD8+/CD3+/TCR-αβ+ cells were produced in 10 days or less (Figures B and C). These data demonstrate that hiPSC can be efficiently differentiated into CD7+ lymphoid progenitors after co-culture on hMSC-DL4.
Figure 7:
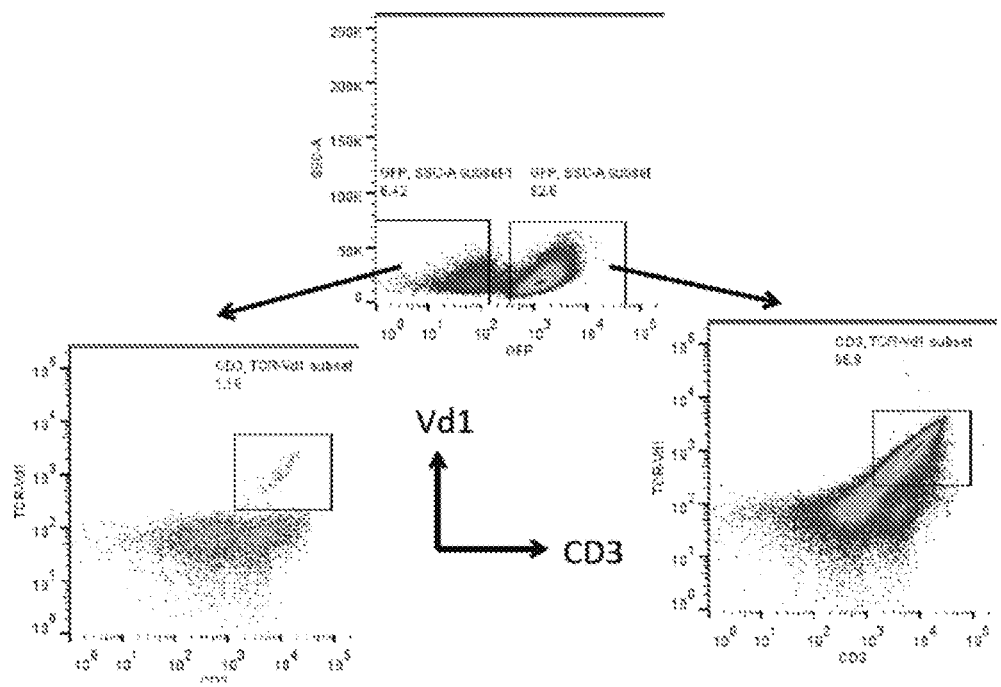
FIG. 7 shows in vitro generation of γδ T cells from hiPSC. Human iPSC were transduced with a lentiviral vector carrying a pre-rearranged human V γδ1 cDNA linked with a 2A-GFP cDNA fragment. After co-culture with OP9 for 18 days, hiPSC derived CD34+ cells were purified on magnetic beads. These cells were subsequently plated on OP9-DL4 cells for T cell differentiation. Cells were harvested at Day 32 and T cell surface markers were analyzed by FACS. The GFP+ population represents Vδ1-2A-GFP lentiviral transduced cells. A high percentage of these GFP positive cells expressed Vδ1 (66%). A low percentage of GFP negative cells expressed Vδ1 (1%). These results demonstrate that Vδ T cells expressing recombinant T Cell Receptors (TCR) can be efficiently produced from genetically modified iPSC. Production of Vδ T cells expressing recombinant T Cell Receptors (TCR) specific for tumor antigens provides a powerful cellular therapy for many types of cancer.

In the methods described herein, CD34+ HSCs can be generated from hiPSCs by co-culturing with human bone marrow stromal stem (hMSC) cells (See FIG. 5). The HSCs produced by this method from patient-specific iPSC after gene correction/modification could be transplanted back into the patient to treat diseases such as sickle cell disease (SCD), SCID or cancer. In the methods described herein, T cells can be generated by culturing hiPSC derived CD34+ cells by co-culturing the hiPSC derived CD34+ cells with hMSC-DL4 (See FIG. 6). HSCs produced by this method from patient-specific iPSC after correction/modification could be transplanted back into the patient to treat diseases. The T cells can comprise γδ T cells. As shown in FIG. 7, γδ T cells expressing recombinant T cell receptor (TCR) can be efficiently produced from genetically modified iPSC. Production of γδ T cells expressing TCR specific for tumor antigens provide a cellular therapy for cancer.

Example 2

Correction of a Mutation Associated with Sickle Cell Anemia by CRISPR/Cas9 Enhanced Gene Replacement Vector Construction The human codon optimized *S. pyogenes* Cas9 with both N-terminal and C-terminal nuclear localization sequences (nls-Cas9-nls) were PCR cloned from px330 vector (Addgene ID: 42230) into a modified pET-28b (EMD Biosciences) vector with a His$_6$-SUMO tag at the N-terminus. A gene block cassette containing a short linker peptide followed by a supercharged GFP with a net charge of +36 and a 23 amino acid influenza virus hemagglutinin HA-2 variant peptide INF7 (GLFEAIEGFIENGWEGMIDGWYG)(SEQ ID NO: 50) was codon optimized for *E. coli* and synthesized (IDT DNA) and cloned to fuse with the C-terminus of the nls-Cas9-nls. An HIV-TAT peptide (YGRKKRRQRRRPPQ)) (SEQ ID NO: 51) coding sequence was also synthesized (IDT DNA) and cloned to fuse with the N-terminus of the nls-Cas9-nls.

Protein Overexpression and Purification

The pET-SUMO-scCas9 plasmid was transformed into *E. coli* strain Rosetta™ 2(DE3) cells (EMD Millipore, Billerica, Mass.) in LB medium. The cells were grown at 37° C. until the optical density reached 0.6 at 600 nm. Induction of protein overexpression was achieved by adding 0.5 mM isopropyl-1-thio-1-D-galactopyranoside (IPTG) and culturing overnight at 18° C. in a shaker. The harvested cells were re-suspended in Ni-binding buffer (20 mM Tris-HCl pH 8.0, 1.5 M NaCl, 25 mM imidazole and 0.2 mM TCEP) and lysed by Emulsiflex C3 high pressure homogenizer (Avestin). Polyethyleneimine (PEI) with final concentration of 0.4% was added into the cleared lysate to precipitate the nucleic acids. The proteins in the supernatant after centrifugation was then precipitated by ammonium sulfate to remove the PEI and re-dissolved in the Ni-binding buffer. The proteins were first purified by a HisTrap nickel affinity column (GE Healthcare) followed by overnight digestion with SUMO protease Ulp1 at 4° C. The cleaved His-SUMO tag was then removed via a second HisTrap column. The flow though containing the scCas9 protein was diluted to reach the final NaCl concentration of 0.5 M and purified on a HiTrap Heparin column (GE Healthcare) by gradient elution with buffer containing 20 mM Tris-HCl pH 8.0, 2.0 M NaCl, and 0.2 mM TCEP. The eluted scCas9 protein was further purified by a size exclusion column Superdex 200 16/600 (GE Healthcare) in gel filtration buffer (20 mM Tris-HCl pH 8.0, 0.5 M NaCl, and 0.2 mM TCEP), sterilized by passing through a 0.22 m filter and concentrated by an Amicon Centrifugal Unit (EMD Millipore) with 100 kDa cutoff. The concentrated protein was quantified by UV spectrophotometer and flash frozen in liquid nitrogen.

Guide RNA Preparation

Template DNA for sgRNA transcription was generated by PCR with primer set adding a T7 promoter and a polyA sequences. sgRNA was in vitro transcribed by T7 RNA polymerase using T7 Ribomax Express System (Promega, Madison, Wis.) according to the manufacturer's manual. The transcribed RNA was purified by phenol: chloroform extraction, ethanol precipitation and followed by column purification with MEGAclear™ Transcription Clean-Up Kit (Ambion, Austin, Tex.). The purified gRNA was quantified by UV spectrophotometer and stored in –80° C. freezer.

Single-Stranded DNA Donors

Single-stranded DNA (ssODN) donors were synthesized by IDT DNA.

| Single-stranded Donor DNAs for HBB sickle correction | |
|---|---|
| HBB-T2-ssODN | ATCCACGTTCACCTTGCCCCACAGGGCAGTAA CGGCAGACTTCTCCtCAGGAGTCAGGTGCACC ATGGTGTCTGTTTGAGGTTGCTAGTGA (SEQ ID NO: 52) |
| HBB-T2-ssODN-wobble | CTTCATCCACGTTCACCTTGCCCCACAGGGCA GTAACGGCAGAtTTtTCCtCAGGAGTCAGGTG CACCATGGTGTCTGTTTGAGGTTGCTAGTGA (SEQ ID NO: 53) |

Cell Culture

Human sickle patient iPSC were derived from skin fibroblasts and were maintained on Matrigel (BD) in mTeSR™1 medium (Stem Cell Technologies, Vancouver, CA) with penicillin/streptomycin.

scCas9-sgRNA-ssODN Complex Preparation and Nucleofection

1/10 volume of 10×PBS was added into sgRNA to reach 1× final concentration. The sgRNA was annealed on PCR thermo cycler with slow decreasing of temperature from 95° C. to 4° C. After annealing, scCas9 protein was added into the sgRNA with a 1:1.5 protein-to-RNA molar ratio and mixed quickly by tapping the tube until all the transient precipitation was gone. The mixture was incubated in room temperature for 10 minutes in dark. Then, 1 molar ratio amount of ssODN was added into the mixture and incubated for additional 10 minutes in dark to form the scCas9-sgRNA-ssODN complex.

One day before nucleofection, cells were detached by Accutase (Stem Cell Technologies) and 1×10$^6$ cells/well cells were seeded on a 6-well plate with 10 μM Rock inhibitor (Y-27632) (EMD Millipore). For each experiment, 5×10$^5$ hsIPSCs were resuspended as single cells in 100 μl supplemented Human Stem Cell Nucleofector Solution 1 (Lonza) and scCas9-sgRNA-ssODN complex was then mixed with the cell solution. The cells were nucleofected with program A-023 using a Nucleofector II device (Lonza, Basel, Switzerland). The efficiency of HBB genome correction was analyzed by ddPCR two days post nucleofection.

Detection of Sickle Correction by ddPCR

The cells nucleofected with the scCas9-sgRNA-ssODN complex were lysed by prepGEM Tissue DNA extraction reagent (ZyGEM, Hamilton, NZ) following manufacturer's manual and 1:3 diluted with water. In a 22 μl ddPCR reaction, 11 μl 2×ddPCR mix (Bio-rad) was mixed with 1 ul each of 5 μM allele-specific FAM or VIC Taqman probes set forth below, 0.2 μl each of a 100 μM forward and reverse primer, and 8.6 μl diluted genomic DNA. Droplets were generated by QX200 Droplet Generator (Bio-rad, Hercules, Calif.) according to the manufacturer's manual. The reaction mix was then transferred into a 96-well PCR plate and the PCR was performed on a standard thermal cycler (Bio-rad). The program for PCR was: Step 1: 95° C. 10 min; Step 2: 95° C. 30s; Step 3: 55° C. 1 min; repeat steps 2-3 for 39 times; Step 4: 98° C. 10 min; Step 5: 8° C. hold. After PCR was done, the plate was then analyzed by QX200 Droplet Reader (Bio-rad).

| T7-sgRNA transcription template primers | |
|---|---|
| T7-T2-F | TAATACGACTCACTATAGGGTAACGGCAGACTTCTCCAC (SEQ ID NO: 54) |
| T7-polyA-R | AAAAAGCACCGACTCGGTGCC (SEQ ID NO: 55) |

Taqman Probes:

| HBB-wb-FAM-TM | FAM-TCCTGaGGAaAAaT-MGB (SEQ ID NO: 56) |
|---|---|
| HBB-wt-FAM-TM | FAM-TGACTCCTGAGGAGAA-MGB (SEQ ID NO: 57) |
| HBB-sk-VIC-TM | VIC-ACTCCTGTGGAGAAG-MGB (SEQ ID NO: 58) | ddPCR Primers:

| R196 | HBB-TaqM-f2 | CAGAGCCATCTATTGCTTACATTTG (SEQ ID NO: 59) |
|---|---|---|
| R197 | HBB-TaqM-r1 | GGCCTCACCACCAACTTCAT (SEQ ID NO: 60) |

Figure 8:
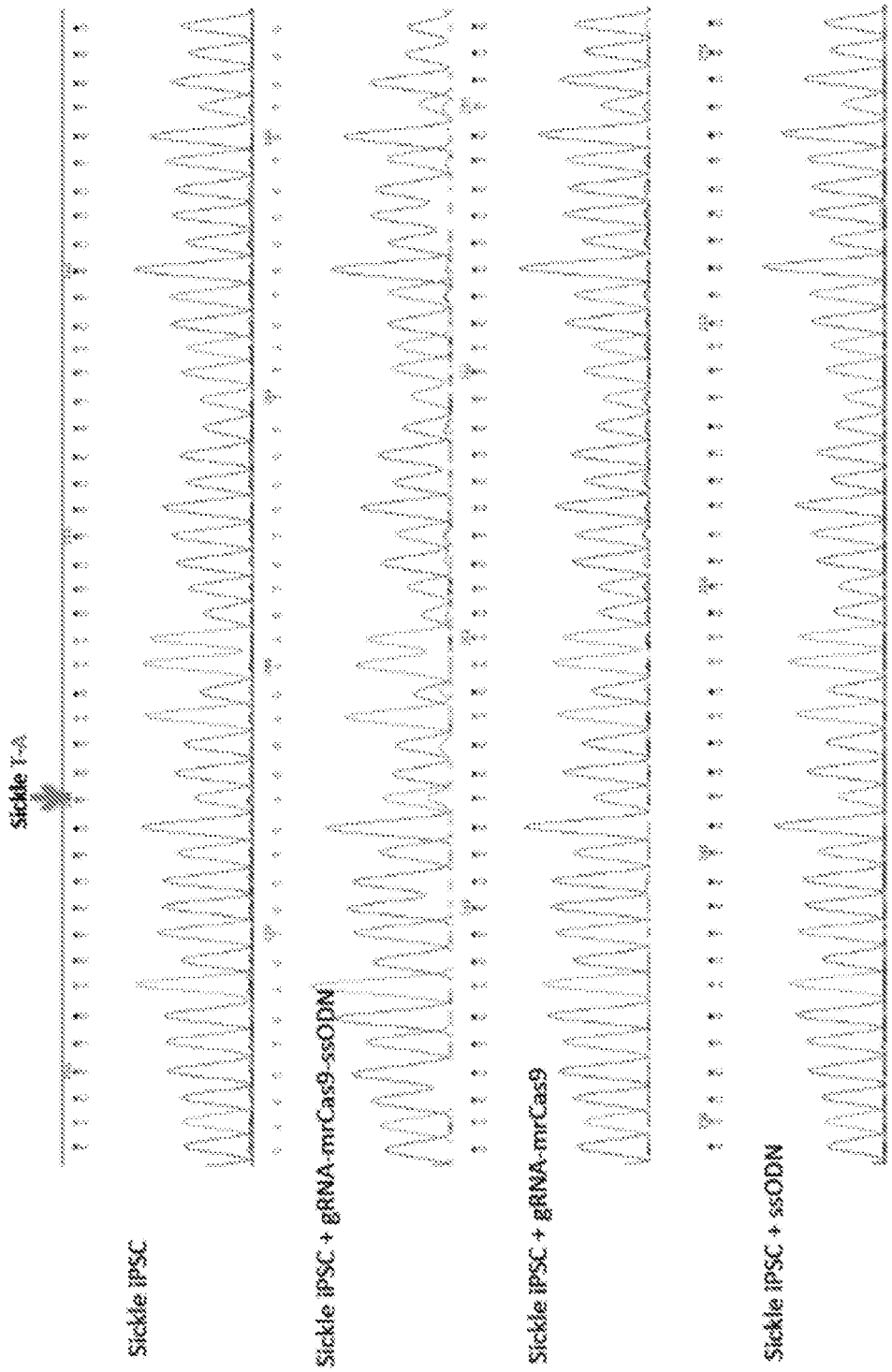
FIG. 8 shows that a correction complex including guide RNA, a modified Cas9 and a single stranded oligonucleotide donor sequence (ssODN) can correct a sickle cell mutation. The complex was introduced into sickle iPSC by nucleoporation, and 2 days later genomic DNA was analyzed by digital PCR (ddPCR) and sequenced. Over 65% of the cells contained at least one corrected gene. The results were confirmed as follows. Two days after introduction of the correction complex, the cells were plated in culture dishes, and 43 individual iPSC colonies were isolated. Genomic DNA was isolated from these colonies and the beta-globin gene was sequenced. Sixty-five percent of the colonies contained at least one corrected beta-globin gene (S corrected to A).

As set forth above, a complex that includes a guide RNA (gRNA), modified recombinant Cas9 protein (mrCas9) and a single-stranded oligodeoxyribonucleotide (ssODN) can be introduced into human stem cells or derivatives thereof to correct a single base mutation that causes disease. Table 1 and FIG. 8 illustrate results from the introduction of a sickle cell correction complex (gRNA-mrCas9-ssODN) into induced Pluripotent Stem Cells (iPSC) derived from skin cells of a sickle cell patient. IPSCs were derived as described in Example 1. The correction complex was introduced into sickle iPSC by nucleoporation and 2 days later genomic DNA was analyzed by digital PCR, using the primers set forth above, and sequenced. Over 65% of the cells contained at least one corrected gene. One corrected gene is sufficient to cure the disease. The results were confirmed as follows. Two days after introduction of the correction complex, the cells were plated in culture dishes, and 43 individual iPSC colonies were isolated. Genomic DNA was isolated from these colonies and the beta-globin gene was sequenced. Sixty-five percent of the colonies contained at least one corrected beta-globin gene (S corrected to A).

TABLE 1

| Pooled ddPCR result (2-day) | gRNA-mrCas9-ssODN | |
|---|---|---|
| | | 68.6% |
| Total colonies picked after 2 weeks | 48 | |
| Mixed colonies | 5 | |
| Total single colonies | 43 | |
| A/A | 14 | 32.6% |
| A/S | 4 | 9.3% |
| S/S | 3 | 7.0% |
| A/indel | 10 | 23.3% |
| S/indel | 6 | 14.0% |
| indel/indel | 6 | 14.0% |
| Clones with at least 1 allele corrected | 28 | 65.1% |
| Clones with indels | 22 | 51.2% |
| Clones with genome modification | 40 | 93.0% |
| Total number of alleles | 86 | |
| Total "A" alleles (corrected) | 42 | 48.8% |
| Total "S" alleles (uncorrected) | 16 | 18.6% |
| Total "indel" alleles | 28 | 32.6% |

TABLE 1-continued

| A: (A + S) | 42/58 = 72.4% |
|---|---|
| *comparable to ddPCR result | |
| HR:NHEJ (A: indel) ratio | 1.50 |

Figure 9:
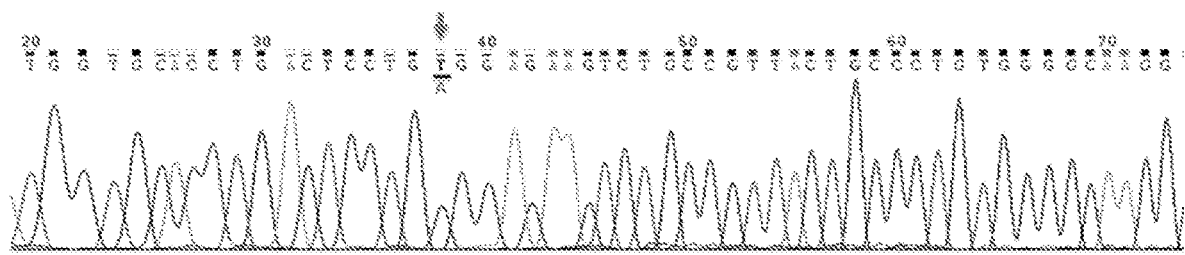
FIG. 9 shows that introduction of a sickle cell correction complex (gRNA-modified recombinant Cas9-ssODN) into patient primary bone marrow CD34+ cells can correct a sickle cell mutation. After twelve days of in vitro differentiation, DNA was analyzed by digital PCR (ddPCR) and sequenced. Approximately equal amounts of betaA and betaS mRNA were observed.
Figure 10:
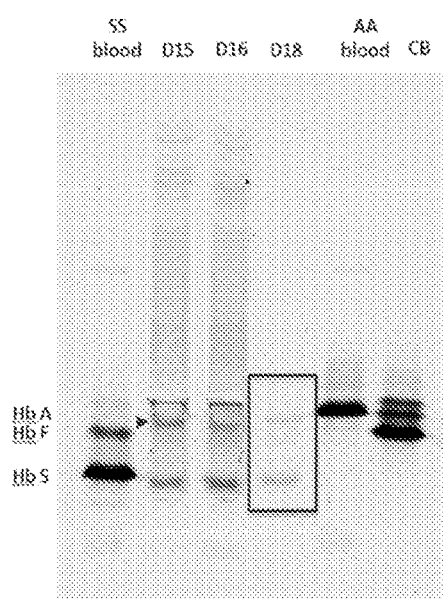
FIG. 10 is an isoelectric focusing (IEF) gel of in vitro differentiated red blood cells from the corrected sickle patient CD34+ cells of FIG. 9, showing an HbA (normal hemoglobin) to HbS (hemoglobin with sickle cell mutation) ratio of about 1:3, which is sufficient to inhibit sickling and treat sickle cell anemia.

Similar studies were performed with patient primary bone marrow CD34+ cells. The protocol was as follows. Bone marrow was obtained from a sickle patient by an IRB approved protocol. CD34+ cells were purified on a Miltenyi anti-CD34+ beads (Miltenyi, Bergisch Gladbach, Germany). The cells were nucleoporated with the complex prepared as described above. After nucleoporation, the cells plated in methycult and BFU-E, CFU-E and CFU-GEMM colonies were picked after two weeks and analyzed for corrected alleles. Table 2 and FIG. 9 illustrate results from the introduction of a sickle cell correction complex (gRNA-mrCas9-ssODN) into patient primary bone marrow CD34+ cells. After twelve days of in vitro differentiation, DNA was analyzed by digital PCR (ddPCR) and sequenced. Approximately equal amounts of betaA and betaS mRNA were observed (See FIG. 9). Immediately after nucleoporation, some of the cells were culture in erythroid differentiation medium for up to eighteen days and enucleated red blood cells were analyzed for HbA. An isoelectric focusing (IEF) gel of in vitro differentiated red blood cells from the corrected sickle patient CD34+ cells showed an HbA (normal hemoglobin) to HbS (hemoglobin with sickle cell mutation) ratio of about 1:3, which is sufficient to inhibit sickling and treat the disease (See FIG. 10).

TABLE 2

| Complex for nucleofection | Cas9wt-36GFP-T2-ssODN | |
|---|---|---|
| Nucleofection Program | P4 DN-100 | |
| BFU-E/CFU-E/GEMM colonies picked on D10 and D15 | 21/23/7 | |
| Total colonies* | 51 | |
| A/A | 2 | 4% |
| A/S | 4 | 8% |
| S/S | 19 | 37% |
| A/indel | 5 | 10% |
| S/indel | 15 | 29% |
| indel/indel | 6 | 12% |
| Clones with at least 1 allele corrected | 11 | 22% |
| Clones with indels | 24 | 47% |
| Clones with genome modification | 29 | 57% |
| Total number of alleles | 102 | |
| Total "A" alleles (corrected) | 13 | 13% |
| Total "S" alleles (uncorrected) | 57 | 56% |
| Total "indel" alleles | 32 | 31% |
| A: (A + S) | 13/70 = 18.6% | |
| *comparable to ddPCR result | | |
| HR:NHEJ (A: indel) ratio | 0.41 | |

Example 3

Correction of a Mutation Associated with Sickle Cell Anemia by CRISPR/Cas9 Enhanced Gene Replacement iPSCs have the potential to generate all cell types including HSPCs (human stem/progenitor cells); therefore, iPSC based gene therapy could provide a curative therapy for sickle cell disease. Correction of sickle iPSCs can provide an unlimited number of cells from which to generate corrected HSPCs, and these corrected HSPCs can be used for autologous transplantation. Importantly, corrected iPSCs and the HSPCs derived from them can be fully characterized and evaluated for safety before transplantation. Described below is CRISPR/Cas9 enhanced gene correction of iPSCs derived from fibroblasts of a sickle patient.

Cell Culture

Human Sickle iPSCs

Human sickle iPSCs were derived from fibroblasts of a skin biopsy obtained from a consented sickle patient at the UAB Kirklin Clinic. The cells were maintained on Matrigel (BD) in mTeSR™1 medium (Stem Cell Technologies) with penicillin/streptomycin. Human sickle iPSCs were passaged every 3-4 days by incubating colonies with Accutase (Stem Cell Technologies), and single cells were seeded on Matrigel coated plates with 10 μM Rock inhibitor (Y-27632) (EMD Millipore). After one day, the media was changed with no rock inhibitor.

Human Sickle Bone Marrow CD34+ Cells

Bone marrow from a consented sickle patient was aspirated in the adult sickle clinic at UAB. The CD34+ cells were purified on anti-Cd34+ beads, aliquoted and stored in liquid nitrogen.

Cas9 Expression Plasmids for E. coli Overexpression

Cas9WT

The S. pyogenes Cas9WT coding sequence with both N-terminal and C-terminal fused nuclear localization sequences (nls-Cas9WT-nls) were PCR cloned from the px330 vector (Addgene ID: 42230) into a modified pET-28b (EMD Biosciences) vector with a His$_6$-SUMO tag at the N-terminus, resulting in a pSUMO-Cas9WT plasmid.

TAT-Cas9 WT-EGFP

Synthesized genes block (IDT DNA) containing a short linker peptide and the coding region of EGFP were ligated to the C-terminus of the nls-Cas9WT-nls and cloned. Coding sequence for a HIV-TAT peptide (YGRKKRRQRRRPPQ) (SEQ ID NO: 51) was also synthesized, ligated to the N-terminus of the nls-Cas9WT-nls and cloned, resulting in the pSUMO-TAT-Cas9WT-EGFP plasmid.

Cas9 WT-36GFP

A synthesized gene block (IDT DNA) containing the E. coli codon optimized coding sequence of supercharged GFP with a net positive charge of +36 (Lawrence et al. "Supercharging Proteins Can Impart Unusual Resilience," J. Am. Chem. Soc. 129(33): 10110 (2007))) and short linker peptide was ligated with the C-terminus of the nls-Cas9WT-nls and cloned, resulting in a pSUMO-Cas9WT-36GFP plasmid.

TAT-Cas9 WT-36GFP

The coding sequence of a HIV-TAT peptide (YGRKKRRQRRRPPQ)(SEQ ID NO: 51) was synthesized, ligated with the C-terminus of Cas9WT-36GFP and cloned, resulting in the pSUMO-TAT-Cas9WT-36GFP vector.

TAT-Cas9 WT-36GFP-INF7

A synthesized gene block (IDT DNA) containing a short linker peptide followed by a supercharged GFP with a net charge of +36 (Lawrence, 2007) and a 23 amino acid influenza virus hemagglutinin HA-2 variant peptide INF7 (GLFEAIEGFIENGWEGMIDGWYG)(SEQ ID NO: 50) (Plank, 1994) was codon optimized for E. coli, ligated with the C-terminus of the nls-Cas9WT-nls and cloned. An HIV-TAT peptide (YGRKKRRQRRRPPQ)(SEQ ID NO: 51) coding sequence was also synthesized, ligated with the N-terminus of nls-Cas9-nls and cloned, resulting in the pSUMO-TAT-Cas9WT-36GFP-INF7 plasmid.

Cas9WT-3×TAT

The coding sequence of 3 tandem repeats of the coding region for HIV-TAT peptide separated with short linkers (YGRKKRRQRRRPPQAGGGSGGSYGRKKRRQRRRP-PQAGGGSGGSYGRKKRRQRR RPPQAG) (SEQ ID NO: 61) was codon optimized for E. coli, synthesized, ligated with the C-terminus of nls-Cas9WT-nls and cloned, resulting in the pSUMO-Cas9WT-3×TAT plasmid.

TAT-Cas9 WT-3×TAT

The coding sequence of a HIV-TAT peptide was (YGRKKRRQRRRPPQ)(SEQ ID NO: 51) synthesized, ligated with the N-terminus of nls-Cas9WT-3×TAT and cloned, resulting in a pSUMO-TAT-Cas9WT-3×TAT plasmid.

Protein Overexpression and Purification

The Cas9WT or Engineered positively charged Cas9 (EpcCas9) expression plasmid was transformed into the E. coli strain Rosetta™ 2(DE3) cells (EMD Millipore) in LB medium. The cells were grown at 37° C. until the optical density reached 0.6 at 600 nm. Induction of protein overexpression was achieved by adding 0.5 mM isopropyl-1-thio-β-D-galactopyranoside (IPTG) and culturing overnight at 18° C. in a shaker incubator. The harvested cells were re-suspended in Ni-binding buffer (20 mM Tris-HCl pH 8.0, 1.5 M NaCl, 25 mM imidazole and 0.2 mM TCEP) and lysed with a Emulsiflex C3 high pressure homogenizer (Avestin). Polyethyleneimine (PEI) was added to the cleared lysate supernatant to a final concentration of 0.4% to precipitate nucleic acids. The supernatant after centrifugation was then precipitated by ammonium sulfate to remove the PEI and the protein pellet was re-dissolved in the Ni-binding buffer. The protein solution was first purified by a HisTrap nickel affinity column (GE Healthcare, Atlanta, Ga.) followed by overnight digestion with SUMO protease Ulp1 at 4° C. The cleaved His-SUMO tag was then removed by passing through a second HisTrap column. The flow through containing the Cas9 protein was diluted to reach a final NaCl concentration of 0.5 M and purified on a HiTrap Heparin column (GE Healthcare) by gradient elution with buffer containing 20 mM Tris-HCl pH 8.0, 2.0 M NaCl, and 0.2 mM TCEP. The eluted Cas9 protein was further purified by a size exclusion column Superdex 200 16/600 (GE Healthcare) in gel filtration buffer (20 mM Tris-HCl pH 8.0, 0.5 M NaCl, and 0.2 mM TCEP), sterilized by passing through a 0.22 m filter and concentrated by an Amicon Centrifugal Unit (EMD Millipore) with a 100 kDa cutoff. The concentrated protein was quantified by UV spectrophotometer, flash frozen in liquid nitrogen and stored at −80° C.

Single Guide RNA Preparation

The DNA template for sgRNA in vitro transcription was generated by PCR with primers adding a T7 promoter at 5' end and a polyA sequence at the 3' end. The sgRNAs was in vitro transcribed by T7 RNA polymerase using a T7 Ribomax Express Kit (Promega) according to the manufacturer's manual. The transcribed RNA was then isolated by phenol: chloroform extraction, ethanol precipitation and column purification with the MEGAclear™ Transcription Clean-Up Kit (Ambion). The sgRNA was eluted in nuclease free water, and the concentration was measured by UV spectrophotometer. The stock sgRNA was then aliquoted and stored in a −80° C. freezer.

Cas9 RNP/ssODN Assembly

Before complexing with Cas9 protein, 10×PBS was added into the stock sgRNA solution to reach 1×PBS final salt concentration. The sgRNA was annealed on a thermo-cycler by slowly decreasing the temperature from 95° C. to 4° C. To form Cas9 RNP, stock Cas9 protein was added to the annealed sgRNA at a 1:1.5 protein:RNA molar ratio and mixed thoroughly by quickly tapping the tube until all the transient precipitation was gone. The mixture was incubated at room temperature for 10 minutes in the dark. Subsequently, ssODN was added at a 1:1 molar ratio with Cas9 RNP for nucleoporation.

Nucleoporation of Human Sickle iPSCs with Cas9 RNP/ssODN

One day before nucleoporation, human sickle iPSCs were detached by accutase (Stem Cell Technologies) and incubated to obtain a single cell suspension in mTesR1 media supplemented with 10 µM Rock inhibitor (Stem Cell Technologies). This single cell suspension was seeded into 6-well plate at density of 5×10⁵ cells/well. On the day of nucleoporation, 5×10⁵ human sickle iPSC cells were prepared with Accutase as described above and resuspended in 100 µl of Human Stem Cell Nucleofector Solution 1 (Lonza) and 7.5 µM of Cas9RNP/ssODN was mixed with the cell suspension in the nucleoporation cuvette. The cells were nucleoporated with program A-023 using a Nucleofector II (Lonza) and transferred into pre-warmed media immediately. The correction efficiencies for the cell population were assayed 2 days after nucleoporation.

Detection of Sickle Correction by ddPCR

Two to five days after nucleoporation, Cas9 RNP/ssODN nucleoporated cells were lysed by prepGEM Tissue DNA extraction reagent (ZyGEM) following the manufacturer's manual and the cell lysate was diluted 1:3 with water. In a 22 µl ddPCR reaction, 11 µl 2×ddPCR mix (Bio-Rad) was mixed with 1 ul each of 5 M allele-specific FAM or VIC Taqman probes, 0.2 µl each of a 100 µM forward and reverse primer, and 8.6 µl diluted cell lysate. Droplets were generated by a QX200 Droplet Generator (Bio-Rad) according to the manufacturer's instructions. The reaction mix was then transferred into a 96-well PCR plate, and PCR was performed on a standard thermal cycler (Bio-Rad). The program for PCR was: Step 1: 95° C. 10 min; Step 2: 95° C. 30s; Step 3: 55° C. 1 min; repeat steps 2-3 for 39 times; Step 4: 98° C. 10 min; Step 5: 8° C. hold. After PCR was completed, the plate was analyzed on a QX200 Droplet Reader (Bio-Rad).

Generation of Single iPSC Clone after Cas9 RNP/ssODN Nucleoporation

To generate single iPSC clones, Cas9 RNP/ssODN nucleoporated sickle iPSCs were seeded in BD matrix gel coated 96-well plates after serial dilution to a density of 20, 10 and 5 cells/well. Fresh mTesR1 media with 10 µM rock inhibitor was changed every 2 days during the first 6 days of culture. mTesR1 media without rock inhibitor was changed every day after day 6. Ten to twelve days after seeding, single iPSC colonies were picked, and the cell lysates were analyzed by Sanger sequencing for genome modification.

Activation and Nucleoporation of Human Patient Bone Marrow Sickle CD34+ Cells

To activate the cell cycle, frozen human sickle bone marrow CD34+ cells were thawed and resuspended into pre-warmed Stemspan media supplemented with CC110 cytokine cocktail (STEMCELL Technology). The cells were cultured in a 37° C. incubator with 5% $CO_2$ and fresh media was partially changed every day for 2 days before nucleoporation. On the day of nucleoporation, 5×10⁵ live CD34+ cells were rinsed with 1×PBS and harvested by centrifugation at 150 g for 15 mins. The cell pellet was resuspended in 100 µl P4 primary cell nucleofection solution (Lonza) and 15 µM of Cas9 RNP/ssODN complex was mixed with the cell suspension in the nucleoporation cuvette. The cells were nucleoporated with program DN-100 using a 4D-Nucleofector (Lonza) and transferred into pre-warmed media immediately. The efficiency of gene correction was analyzed 6 days after nucleoporation.

Erythroid Colony Forming Unit (CFU) Assay for Cas9 RNP Nucleoporated CD34+ Cells After nucleoporation with Cas9 RNP/ssODN complex, CD34+ cells were seeded into Methocult media (Stem Cell Technologies) at a density of 500-1000 cells/mL in 35 mm tissue culture plates. Cells were grown in a 37° C. incubator with 5% $CO_2$ for 12-15 days until the colonies were large enough to pick individually for analysis.

In Vitro Erythroid Differentiation of CD34+ HSPCs into RBCs

One day after the nucleoporation of CD34+ cells with Cas9 RNP/ssODN complex, the media was changed to Erythroid expansion media (Stemspan SFEM (STEMCELL Technologies) supplemented with 1 u/mL erythropoietin (EPO), 2 nM dexamethasone (DEX), 1 nM β-Estradiol, 20 ng/mL human SCF, and 5 ng/mL human IL-3.) The media was changed every 2 days. After the first 7 days of expansion and differentiation, the media were supplemented with a higher concentration of EPO (2 u/mL) until differentiated RBCs are harvested at day 15-18.

Mass Spectrometry Analysis of Corrected Hemoglobin Beta Protein in RBCs

Hemolysates of RBCs differentiated from human sickle bone marrow CD34+ HSPCs were separated by PAGE. The globin band was cut out of the gel and trypsinized. Peptides were separated and analyzed by LC-MS/MS.

```
Sequences
In vitro transcribed sgRNA sequences:
T1 sgRNA:
                                      (SEQ ID NO: 62)
GGGUCUGCCGUUACUGCCCUGGUUUUAGAGCUAGAAAUAGCAAGUUAAAA

UAAGGCUAGUCCGUUAUCAACUUGAAAAAGUGGCACCGAGUCGGUGCUUU

UUUU

T2 sgRNA:
                                      (SEQ ID NO: 63)
GGGUAACGGCAGACUUCUCCACGUUUUAGAGCUAGAAAUAGCAAGUUAAA

AUAAGGCUAGUCCGUUAUCAACUUGAAAAAGUGGCACCGAGUCGGUGCUU

UUUUU 91-nt correction ssODN:
                                      (SEQ ID NO: 52)
ATCCACGTTCACCTTGCCCCACAGGGCAGTAACGGCAGACTTCTCCtCAG

GAGTCAGGTGCACCATGGTGTCTGTTTGAGGTTGCTAGTGA 95-nt T2 wobble ssODN:
                                      (SEQ ID NO: 53)
CTTCATCCACGTTCACCTTGCCCCACAGGGCAGTAACGGCAGAtTTtTC CtCAGGAGTCAGGTGCACCATGGTGTCTGTTTGAGGTTGCTAGTGA 90-nt T1 wobble ssODN:
                                      (SEQ ID NO: 64)
ACCTCAAACAGACACCATGGTGCACCTGACTCCTGAGGAGAAGTCTGCC

GTCACAGCTCTGTGGGGCAAGGTGAACGTGGATGAAGTTGG

PCR primers for T2 sgRNA in vitro transcription
template
                                      (SEQ ID NO: 54)
T7-T2F: TAATACGACTCACTATAGGGTAACGGCAGACTTCTCCAC (SEQ ID NO: 55)
T7-R:   AAAAAGCACCGACTCGGTGCC
```

-continued

PCR primers for T1 sgRNA in vitro transcription
template
                                            (SEQ ID NO: 65)
T7-T1F: TAATACGACTCACTATAGGGTCTGCCGTTACTGCCCTG (SEQ ID NO: 55)
T7-R: AAAAAGCACCGACTCGGTGCC PCR primer for on-target Sanger sequencing
                                            (SEQ ID NO: 66)
R157: TCCACATGCCCAGTTTCTAT (SEQ ID NO: 67)
R158: AGTAGCAATTTGTACTGATGGTATG Engineered Positively Charged Cas9 RNPs/ssODN (Epc-Cas9 RNPs/ssODN) Efficiently Correct the Sickle Mutation in Human Patient iPSC (Induced Pluripotent Stem Cells)

Figure 11:
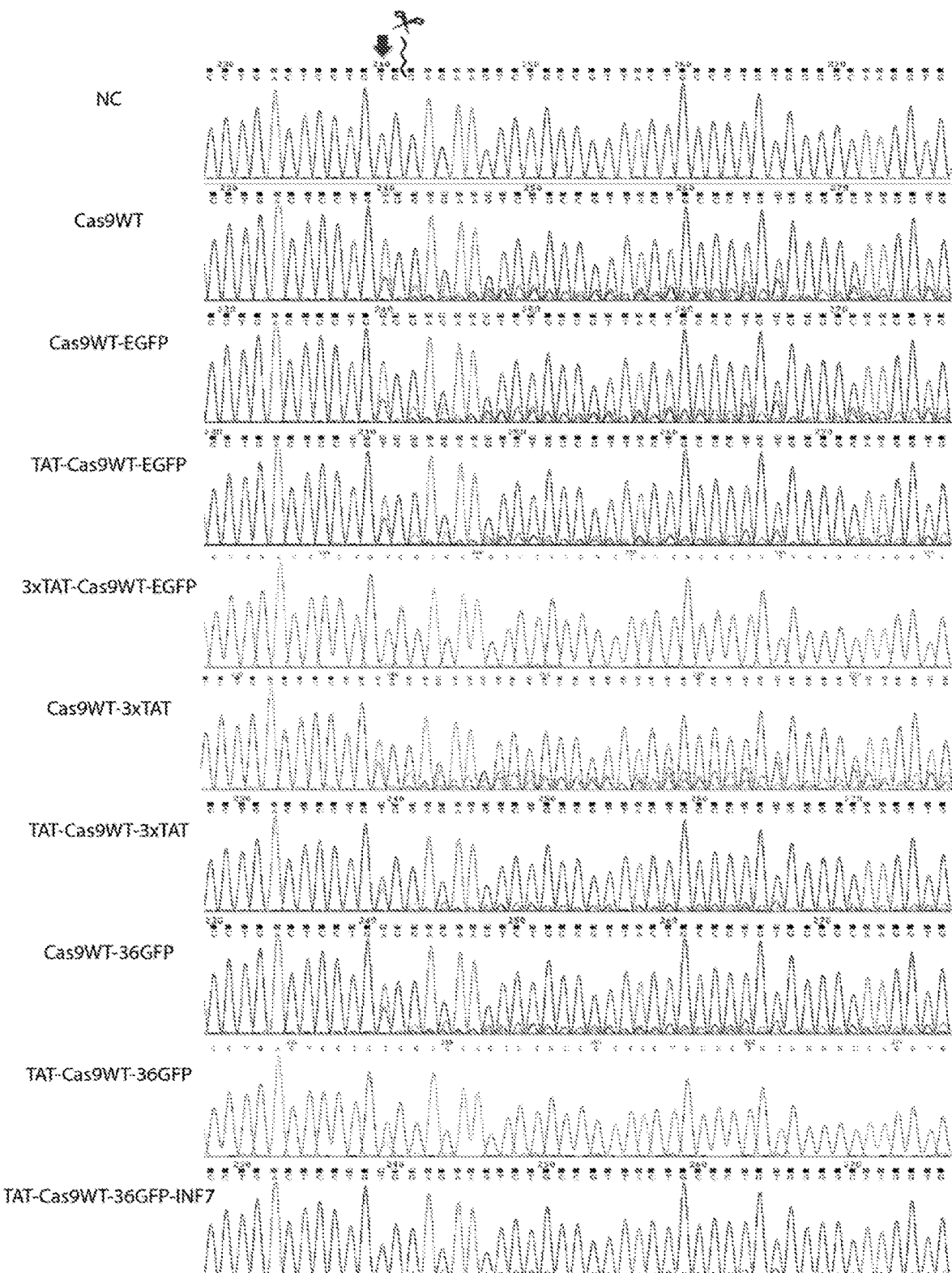
FIG. 11 shows that engineered positively charged Cas9 RNPs/ssODN (EpcCas9 RNPs/ssODN) efficiently correct the sickle mutation in human patient iPSCs. Wild type Cas9 (Cas9WT) RNP and eight engineered positively charged (EpcCas9) RNPs were co-nucleoporated with correction ssODN into human sickle iPSCs. Sickle correction efficiencies in the pooled cells were determined by Sanger sequencing at two days post nucleofection. The arrow indicates the position of sickle correction (T->A) and the scissors indicate the Cas9WT-36GFP RNP cutting site on the sickle HBB DNA.

To correct the sickle HBB gene, human sickle patient derived iPSCs were nucleoporated with Cas9WT/T2 RNP, Cas9WT-EGFP/T2 or 8 different EpcCas9/T2 RNPs (Engineered positively-charged Cas9/T2 RNPs) together with a 91-nt ssODN correction template (SEQ ID NO: 51). Cas9/T2 RNPs induce a double strand break near (2 bp downstream) the sickle mutation. The proximity of the cut site to the mutation enhances HDR of the sickle mutation (T->A) using the 91-nt ssODN correction template. On-target Sanger sequencing data for the population of iPSCs demonstrate correction of the sickle mutation at high efficiency in Cas9WT RNP/ssODN nucleoporated cells (FIG. 11). The addition of an EGFP (Enhanced Green Fluorescent Protein) domain at the C-terminus of Cas9WT did not affect the level of correction.

Correction efficiencies vary in cells nucleoporated with the 8 different EpcCas9s RNPs. The addition of a positively charged HIV TAT peptide at the N-terminus of the Cas9WT-EGFP (TAT-Cas9WT-EGFP) results in a small decrease in correction efficiency compared to the Cas9WT and Cas9WT-EGFP and a small decrease in indels. Addition of 3× tandem repeats of TAT at the N-term of the Cas9WT-EGFP (3×TAT-Cas9WT-EGFP) almost completely abolishes correction and indel levels, indicating loss of Cas9 enzymatic activity from this modification. This result suggests that a relatively high number of positive charges linked to the N-terminus of Cas9 severely inhibits enzymatic activity. Interestingly, addition of positive charges at the C-terminus of Cas9 (Cas9WT-3×TAT or Cas9WT-36GFP) results in a high level of correction and a relatively low level of indels. These results suggest that positive charges linked to the C-terminus of Cas9 significantly inhibit exonuclease digestion of cleaved ends and stimulate relegation of ends without formation of indels. Similar levels of correction and indels were observed from EpcCas9 with a C-terminal addition of 3× tandem repeats of TAT peptides or a positively charged +36GFP.

Figure 12:
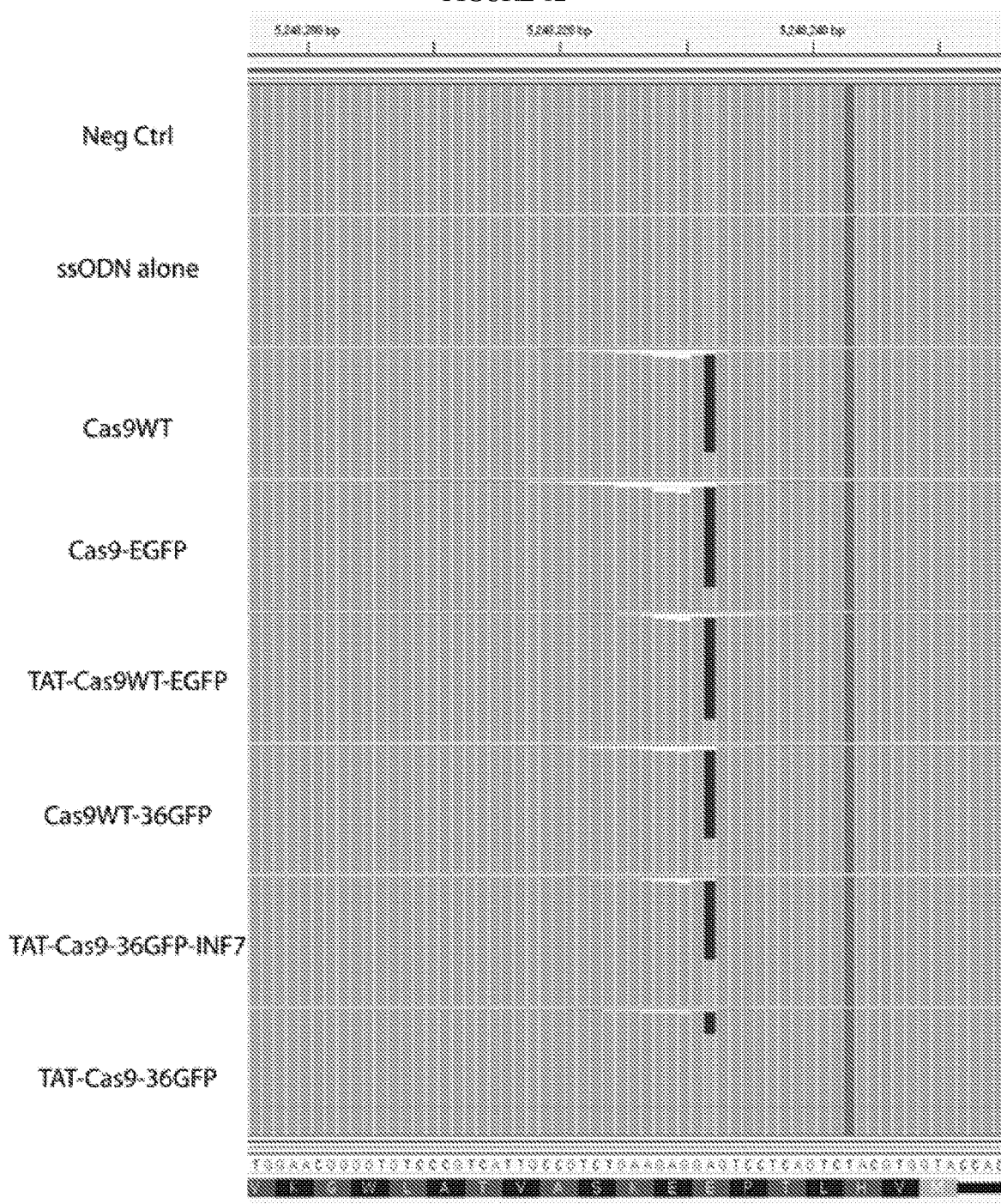
FIG. 12 shows the results of deep sequencing of on-target modifications in human sickle iPSC populations. On-target deep sequencing analysis of human sickle iPSCs nucleoporated with Cas9WT RNP/ssODN, Cas9WT-EGFP, or four EpcCas9 RNPs/ssODNs is shown. Black bars indicate the corrected base and the space below the black bars indicates the sickle cell mutation. The negative control and the ssODN alone both show only the sickle cell mutation. All iPSC samples also contain a SNP near the sickle mutation (column on right hand side).

EpcCas9s with both N-terminal and C-terminal positively charged modifications (TAT-Cas9WT-3×TAT and TAT-Cas9WT-36GFP) produce significantly less indels. Interestingly, further addition of a negatively charged INF7 peptide to the C-terminus of TAT-Cas9WT-36GFP (TAT-Cas9WT-36GFP-INF7) significantly enhances the correction efficiency compared to TAT-Cas9WT-36GFP. Sanger sequencing results were verified by deep sequencing analysis of on-target correction and indels for iPSC populations after nucleoporation with Cas9WT and selected EpcCas9 RNPs (FIG. 12).

EpcCas9 RNPs Suppress On-Target Indels in Human Sickle iPSC

Figure 13:
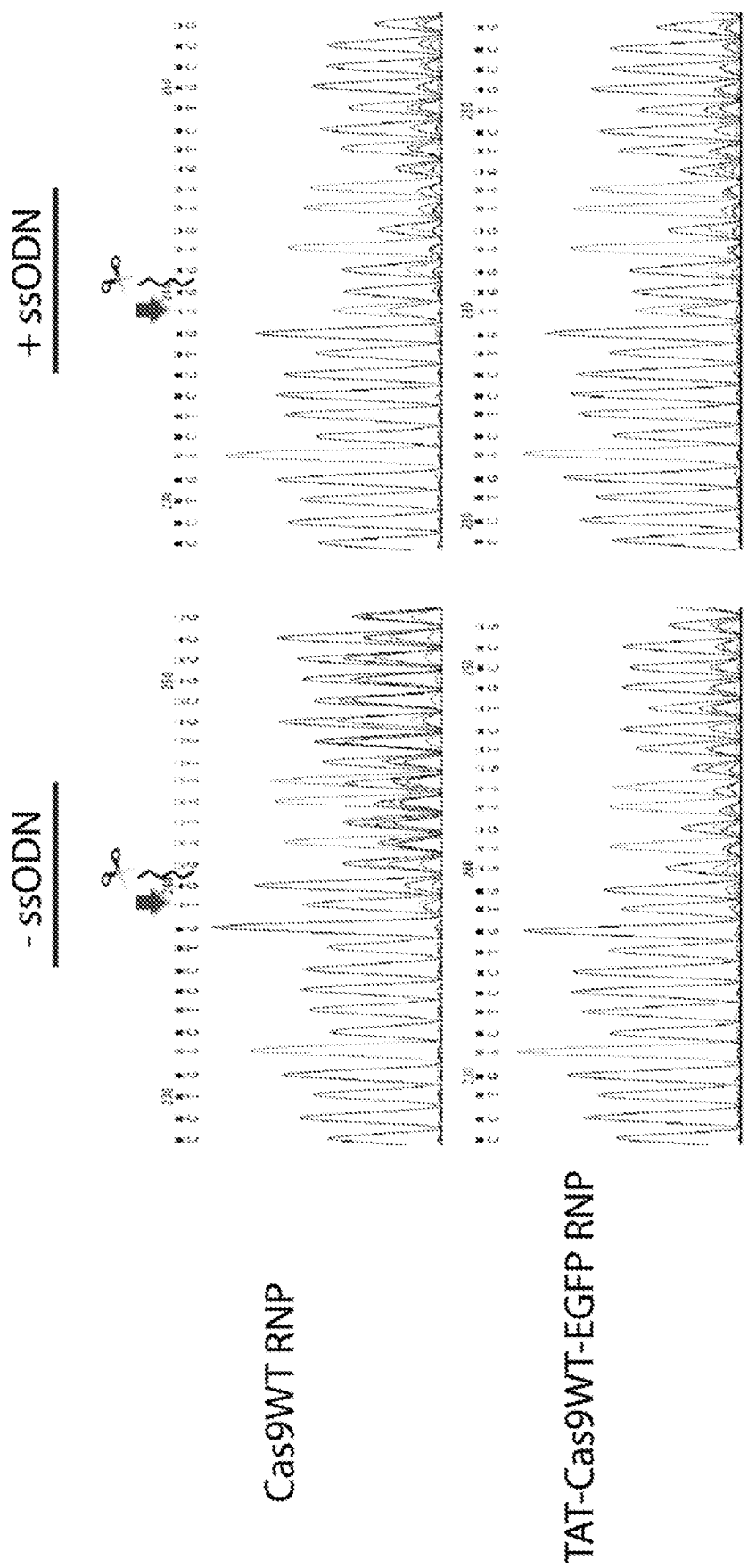
FIG. 13 shows that TAT-CAs9WT-EGFP RNP suppresses on-target indels. Human sickle iPSCs were nucleoporated with Cas9WT and TAT-Cas9WT-EGFP RNPs with (+ssODN) or without correction ssODN (–ssODN). Indel and correction efficiencies were analyzed by Sanger sequencing at two days post nucleoporation. The arrows indicate the position of sickle correction (T->A) and the scissors indicate the Cas9WT-36GFP RNP cutting site on the sickle HBB DNA.

To study further the effects of positively charged modifications on the efficiency of HDR based gene corrections and NHEJ based indels, human sickle iPSC were nucleoporated with Cas9 RNPs plus or minus a 91-nt ssODN correction template. On-target Sanger sequencing analysis demonstrated that addition of ssODN (+ssODN) to both Cas9WT RNP and TAT-Cas9WT-EGFP corrects the sickle mutation with a similar high efficiency (FIG. 13). However, in the absence of ssODN (−ssODN), indel formation is dramatically lower with TAT-Cas9WT-EGFP compared to Cas9WT. Since HDR requires DSBs (Double Strand Breaks), the enzymatic activity of Cas9 is apparently not lowered by the addition of 1×TAT. Therefore, the large discrepancy in indel formation is not due to lower transduction efficiency or lower enzymatic activity of TAT-Cas9WT-EGFP.

Figure 14:
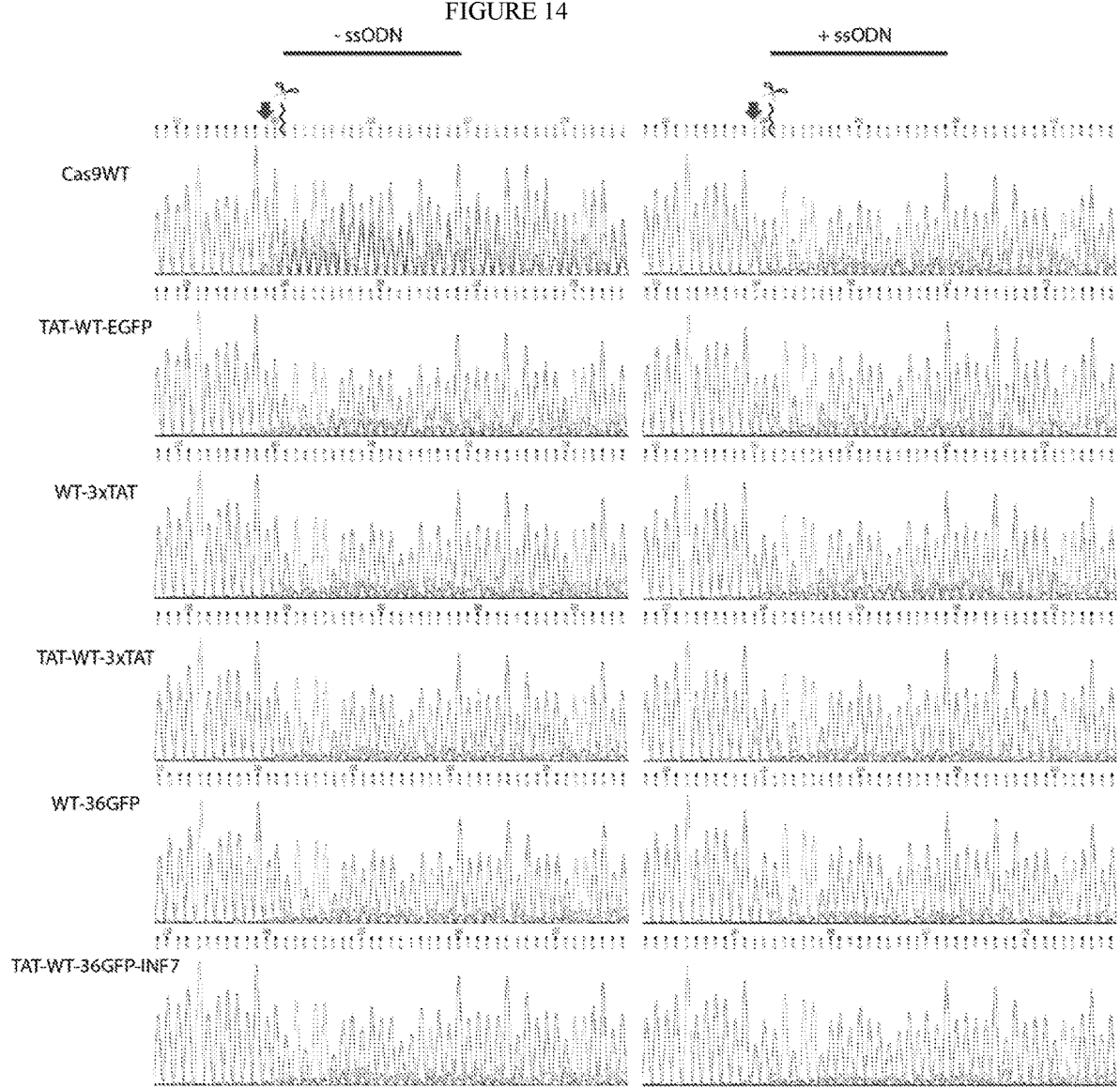
FIG. 14 shows that EpcCas9 RNPs suppress on-target indels in human sickle iPSCs. Human sickle iPSCs were nucleoporated with Cas9WT and five EpcCas9 RNPs, with or without correction ssODN. Indel and correction efficiencies were analyzed by Sanger sequencing at two days post nucleoporation. The arrows indicate the position of sickle correction (T->A) and the scissors indicate the Cas9WT-36GFP RNP cutting site on the sickle HBB DNA.

To confirm these observations, the correction and indel efficiencies in 5 other EpcCas9 RNPs with (+) or without (−) ssODN (FIG. 14) was evaluated. Sanger sequencing analyses confirmed that all EpcCas9 RNPs result in significantly fewer on-target indels in the absence of ssODN (−ssODN). Although the correction efficiencies of EpcCas9 RNPs/+ssODN vary with different positively charged modifications (FIG. 14), indel formation is suppressed by all positively charged Cas9 modifications.

EpcCas9 RNPs Enhance Cell Survival after Nucleoporation in Human Sickle iPSC

Figure 15:
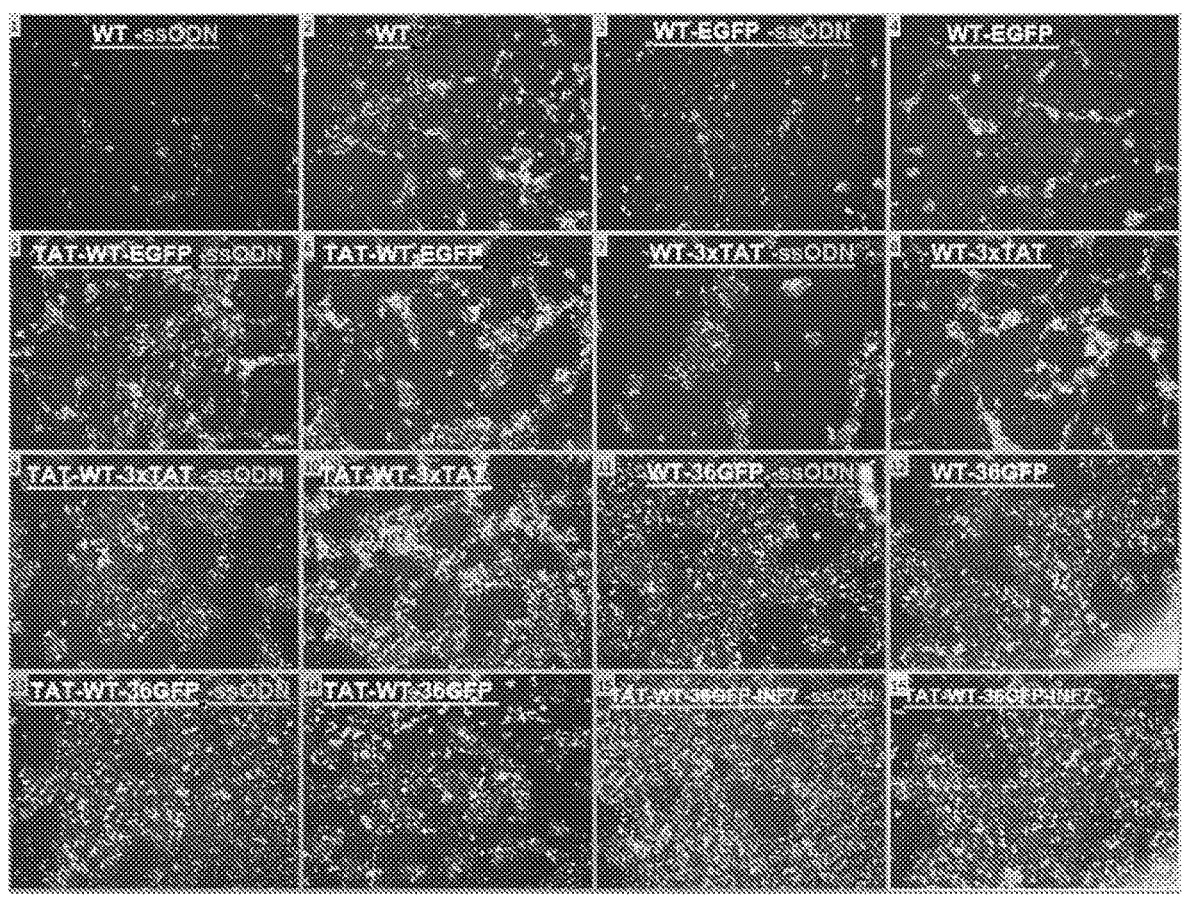
FIG. 15 shows that EpcCas9 RNPs enhance cell survival after nucleoporation in human sickle iPSCs. Human sickle iPSCs were nucleoporated with Cas9WT RNP and seven EpcCas9 RNPs with or without correction ssODN. Cell survival was assessed by light microscopy at two days post nucleofection.

To determine whether positively charged modifications affect cell survival, sickle iPSC were nucleoporated with Cas9WT RNP or 7 different EpcCas9s with (+) or without (−) a correction ssODN. Immediately after nucleoporation, cells were plated in culture dishes and growth was examined after 48 hours. Cell survival was poor with Cas9WT and increased dramatically with higher positively charged modifications (FIG. 15). Excellent cell survival was achieved with Cas9WT-36GFP and EpcCas9s containing both N-terminal and C-terminal positively charged modifications (FIG. 15). Considering cell survival and correction/indel efficiency, the optimum balance of high correction, low indel formation and excellent cell survival is achieved with Cas9WT-36GFP and TAT-Cas9-36GFP-INF7 RNPs in human sickle iPSCs.

ssODN: Cas9 RNP Ratios for Sickle Correction in Human iPSC

Figure 16:
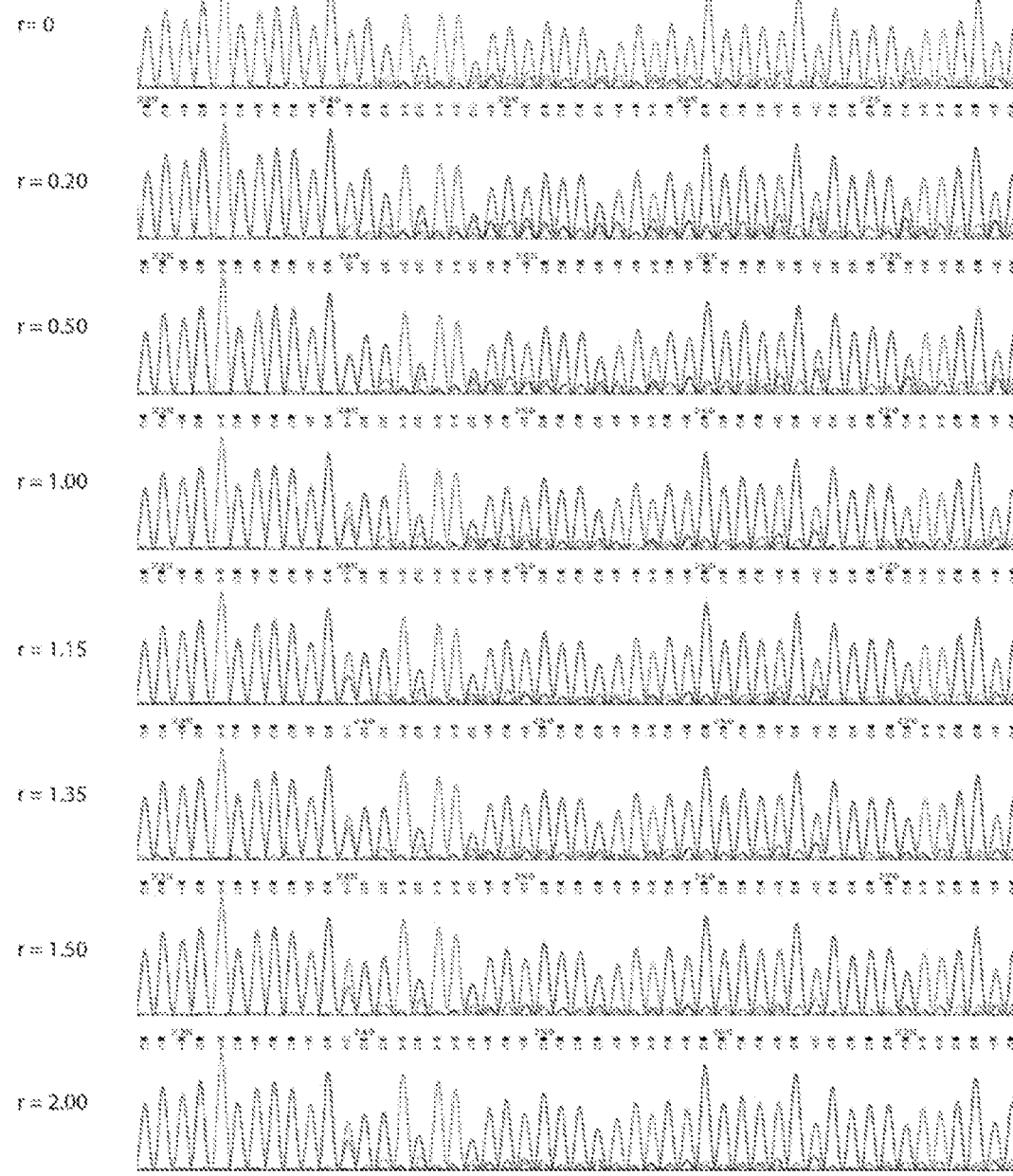
FIGS. 16A and 16B show ssODN:Cas9 RNP ratios for sickle correction in human iPSCs. Correction ssODN and Cas9WT-36GFP/T2 RNP were nucleoporated into sickle patient iPSC at molar ratios of 0, 0.2, 0.5, 1.0, 1.15, 1.35, 1.5 and 2.0. (A Cas9WT-36GFP:T2 gRNA molar ratio of 1:1.35 was fixed for these experiments. For example, the r=0.5 value in the graph below is 0.5 ssODN:1.0 Cas9WT-36GFP: 1.35 T2 gRNA.) Forty-eight hours after nucleoporation of the ssODN:Cas9WT-36GFP RNPs, sickle corrections were quantitated by digital droplet PCR (ddPCR) (FIG. 16A) and Sanger sequencing (FIG. 16B). The percent correction (betaA/betaS alleles×100) was plotted verses r (ssODN:Cas9WT-36GFP RNP). A dashed sigmoidal curve was fitted with the data points. (B) An arrow indicates the position of sickle correction (T->A) and scissors indicate the Cas9WT-36GFP RNP cutting site on sickle HBB DNA.

The ratio of ssODN correction template to Cas9 RNP (ssODN:Cas9 RNP) is important for HDR and cell survival. Single stranded ODN is toxic to cells; therefore, high ssODN:Cas9 RNP ratios may result in poor cell survival after nucleoporation. However, low ssODN:Cas9 RNP ratios may result in inefficient HDR. To achieve high correction efficiencies with high cell survival, ssODN:Cas9 RNP ratios were optimized. The efficiency of sickle mutation correction with increasing doses of ssODN in sickle patient iPSC was determined. A Cas9WT-36GFP:T2 sgRNA molar ratio of 1:1.35 was fixed for these experiments, and the molar ratios of ssODN:Cas9WT-36GFP RNP ranged from 0 to 2.0 (r=0, 0.2, 0.5, 1.0, 1.15, 1.35, 1.5 and 2.0). For example, the r=0.5 value in FIG. 6 is 0.5 ssODN:1.0 Cas9WT-36GFP:1.35 T2 sgRNA. Forty-eight hours after nucleoporation of the ssODN:Cas9WT-36GFP RNPs, sickle corrections were quantitated by digital droplet PCR (ddPCR) (FIG. 16A) and Sanger sequencing (FIG. 16B). The percent correction (betaA/betaS alleles×100) was plotted verses r (ssODN:Cas9WT-36GFP RNP). Correction efficiencies increased with r=0.2 to r=1.0 and reached a plateau at 1.15 (65.7%). Increasing r above 1.15 did not significantly increase correction efficiency and dramatically inhibited cell survival.

Cas9:sgRNA Ratios for Sickle Correction in Human iPSC

Figure 17:
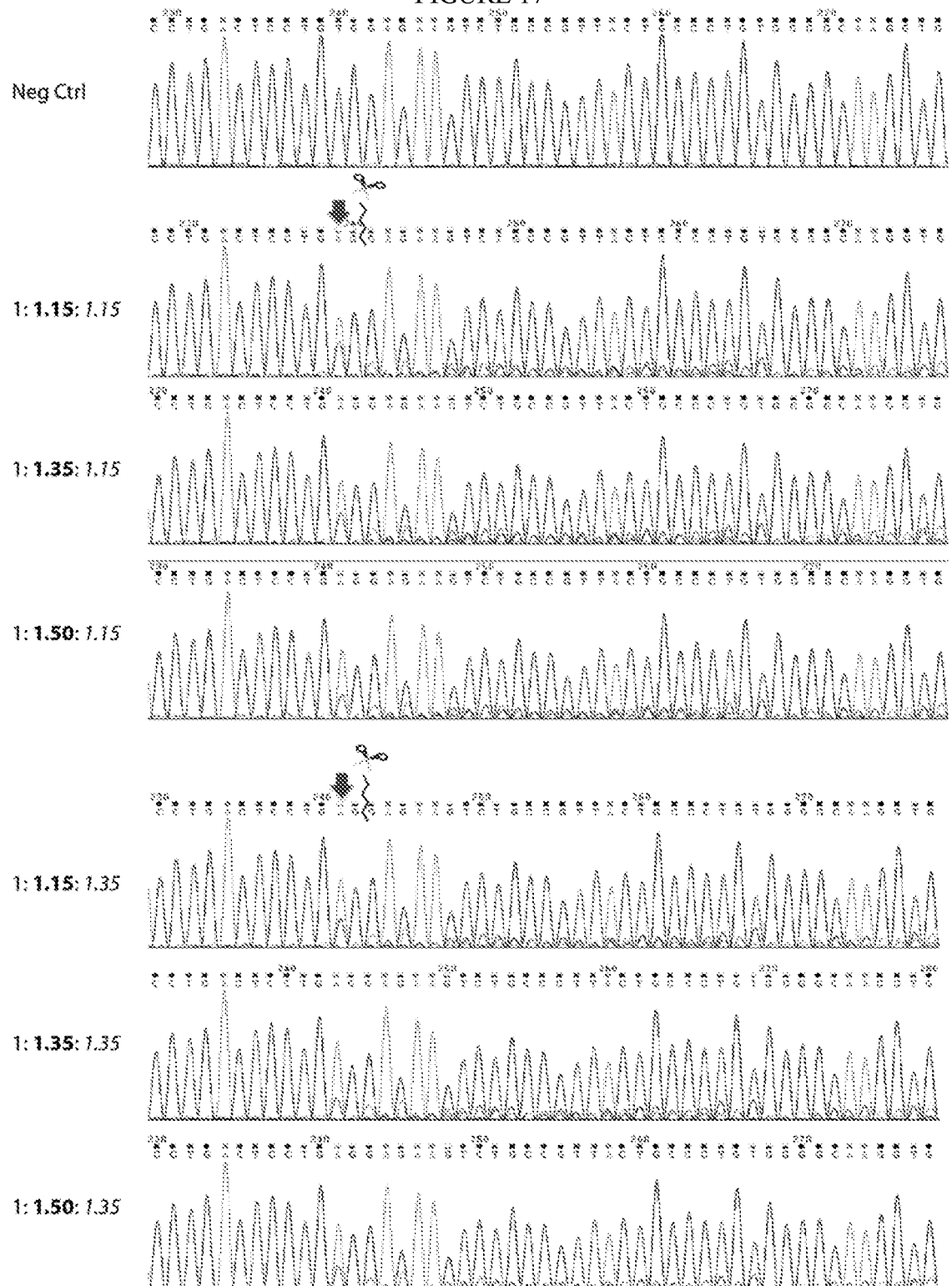
FIG. 17 shows Cas9:sgRNA ratios for sickle correction in human iPSCs. Cas9-36GFP:sgRNA molar ratios of 1:1.15, 1:1.35 and 1:1.50 with ssODN molar ratios of 1.15 or 1.35 were tested to determine optimal correction efficiency of the sickle mutation in patient iPSC. The mixtures were nucleoporated into human sickle iPS cells and the Sanger sequencing results for the pooled cells were analyzed at two days post nucleofection. Arrows indicate the position of sickle correction (T->A) and scissors indicate the Cas9WT-36GFP RNP cutting site on sickle HBB DNA.

Theoretically, the optimal Cas9:sgRNA molar ratio is 1:1. Saturation of the Cas9 protein with sgRNA ensures maximal Cas9 enzymatic activity and reduces the possibility of free Cas9 interactions with other small RNAs that may produce unpredictable off-target genome modifications. Small RNAs are sensitive to nucleases; therefore, molar ratios of Cas9:sgRNA greater than 1:1 may be necessary to saturate Cas9. Cas9-36GFP:sgRNA molar ratios of 1:1.15, 1:1.35 and 1:1.5 were tested with ssODN molar ratios of 1.15 or 1.35 to determine optimal correction efficiency of the sickle mutation in patient iPSC. Sanger sequencing results and cell survival analyses demonstrated that optimal correction efficiencies and cell survivals were achieved with a Cas9-36GFP:sgRNA:ssODN molar ratio of 1:1.35:1.15 (FIG. 17).

Colony Analysis for Sickle Correction in Human iPSC

Human sickle iPSC were nucleoporated with TAT-Cas9WT-36GFP-INF7:T2 sgRNA:ssODN at a molar ratio of 1.0:1.35:1.0 to investigate the correction efficiency in cell populations (FIG. 18) and, subsequently, at a single cell level (Table 3). For single cell analysis, nucleoporated iPSCs were plated in a 96-well plate after serial dilution. Two weeks later, single iPSC colonies were picked, genomic DNA isolated, and Sanger sequencing performed. Forty-three single iPSC colonies were analyzed for on-target modifications. Table 3 summarizes the Sanger sequencing results for these iPSC clones. Twenty-eight of the 43 colonies contained at least one corrected allele (A/A, A/S or A/indel); therefore, 65.1% of the clones contained at least one corrected allele. iPSC containing at least one corrected allele will produce red blood cells that do not sickle.

TABLE 3

Summary for Sanger sequencing results of iPSC colonies corrected by EpcCas9 RNP/ssODN

| | | |
|---|---|---|
| Total single colonies | 43 | |
| A/A | 14 | 32.6% |
| A/S | 4 | 9.3% |
| S/S | 3 | 7.0% |
| A/indel | 10 | 23.3% |
| S/indel | 6 | 14.0% |
| indel/indel | 6 | 14.0% |
| Colonies with at least 1 allele corrected | 28 | 65.1% |
| Colonies with indels | 22 | 51.2% |
| Colonies with genome modification | 40 | 93.0% |
| Total number of alleles | 86 | |
| Total "A" alleles (corrected) | 42 | 48.8% |
| Total "S" alleles (uncorrected) | 16 | 18.6% |
| Total "indel" alleles | 28 | 32.6% |

Genome-editing events were also assessed at the allele level for these iPSC clones. Forty-two of 86 alleles (48.8%) were corrected, 28 of 86 alleles (32.6%) contained indels and 16 of 86 alleles (18.6%) were unmodified. This high rate of genome modification (81.4% of alleles and 93% of cells) demonstrates highly efficient gene targeting with the biochemical complex is possible.

Correction of Human iPSC with EpcCas9 RNPs and Wobble ssODNs

Retargeting of corrected DNA is a potential pitfall for the CRISPR/Cas system in HDR based gene correction. Compared to plasmid or viral delivery, the risk of retargeting for Cas9 RNP is low due to the RNPs short half-life; however, retargeting is difficult to avoid completely. In this example, the sickle mutation is located within the T2 sgRNA targeting sequence and is only 2 base pairs from the PAM. After correction with the ssODN, the corrected DNA contains a 1 base mismatch with the sgRNA target sequence. This difference reduces but does not eliminate retargeting. One strategy to prevent retargeting is to introduce wobble base changes into the correction template. These base changes do not alter the translated protein sequence but alter the DNA sequences at or near the PAM sequence so that the corrected DNA will no longer be a target for the Cas9 RNP. Based on this strategy, sickle iPSC were nucleoporated with TAT-Cas9WT-36GFP-INF7/T1 sgRNA/T1wb-ssODN and TAT-Cas9WT-36GFP-INF7/T2sgRNA/T2wb-ssODN to determine whether EpcCas9 RNP could correct the sickle mutation at high efficiencies with wobble ssODNs.

Figure 18:
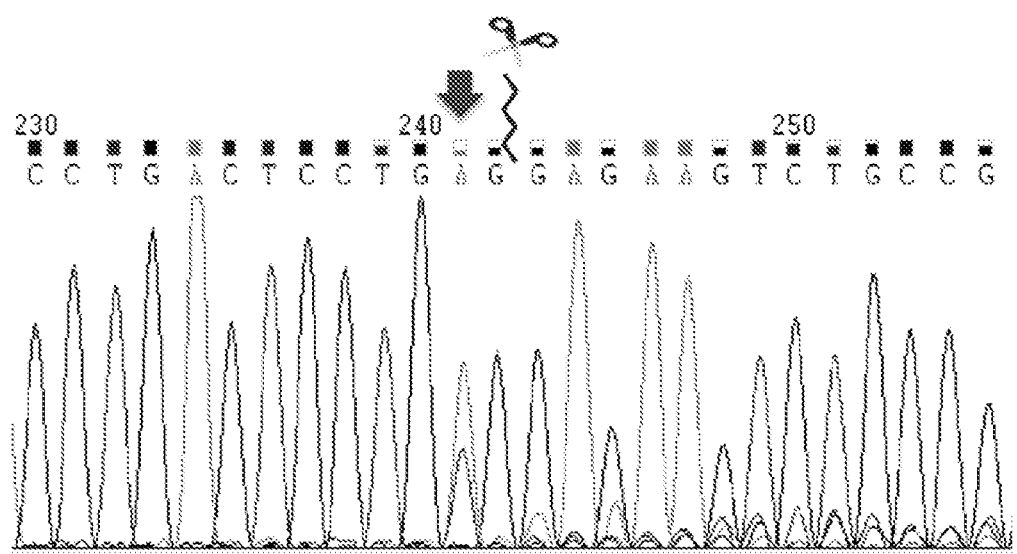
FIG. 18 shows correction of human sickle iPSCs by EpcCas9 RNP/ssODN. Sanger sequencing analysis of pooled human sickle iPS cells nucleofected with TAT-Cas9WT-36GFP-INF7 RNP/ssODN was performed. The arrow indicates the position of sickle correction (T->A) and the scissors indicate the position of EpcCas9 RNP induced DSB on the sickle HBB DNA.
Figure 19:
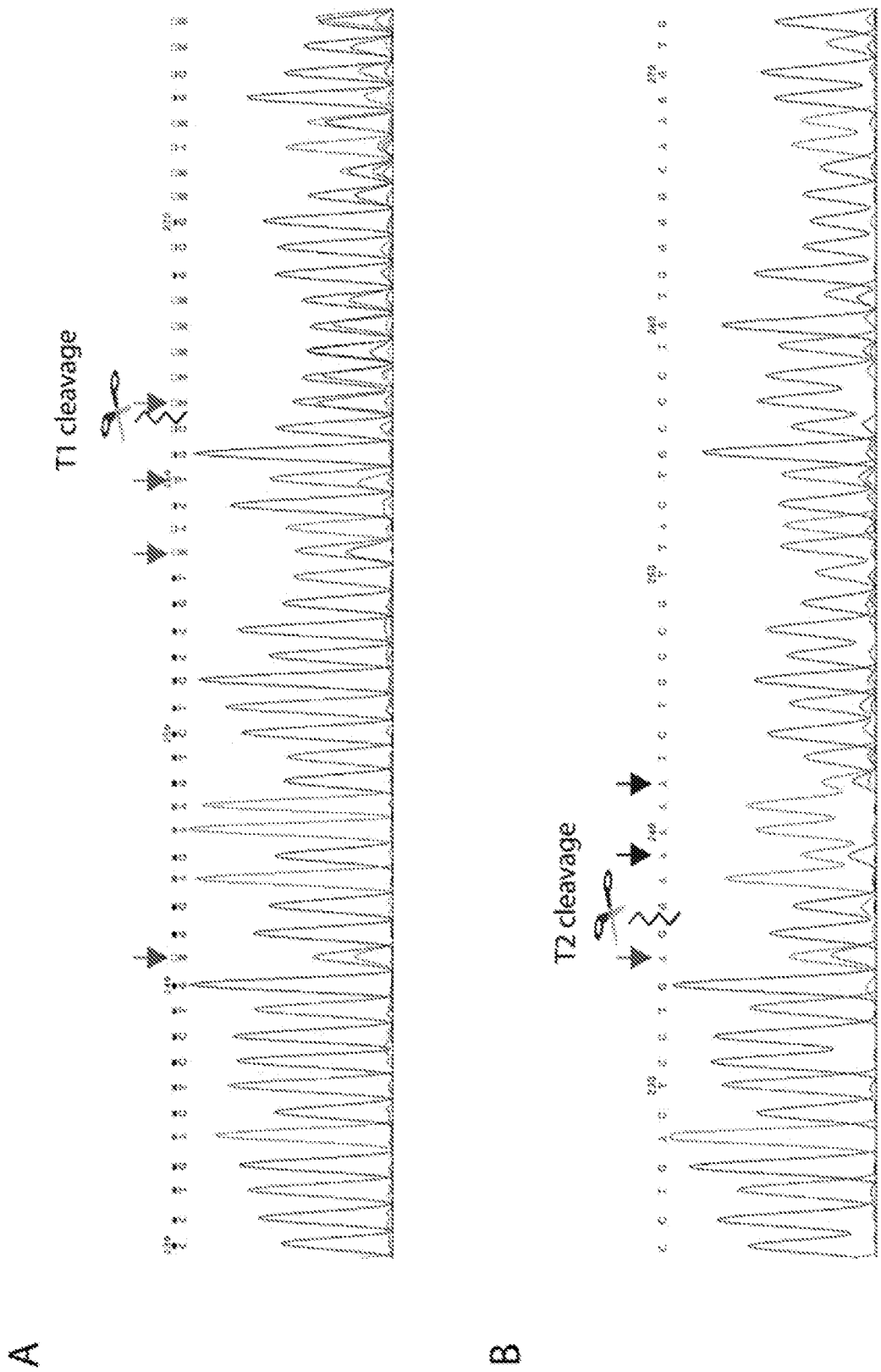
FIGS. 19A and 19B show correction of human iPSCs with EpcCas9 RNP and wobble ssODNs. Human sickle iPSC were nucleoporated with TAT-Cas9-36GFP-INF7 RNP and ssODNs containing wobble bases near the gRNA cleavage sites. (A) Sanger sequencing of iPSC populations nucleoporated with T1 gRNA and T1-wb ssODN was performed. The arrow on the left hand side of FIG. 19A indicates the position of sickle mutation and the 3 arrows located downstream of the sickle mutation indicate positions of wobble bases. Scissors point to the T1 cleavage site. (B) Sanger sequencing of iPSC populations nucleoporated with T2 gRNA and T2-wb ssODN was performed. The arrow on the left hand side indicates the position of the sickle mutation and the 2 arrows downstream of the sickle mutation indicate the positions of wobble bases. Scissors point to the T2 cleavage site.

Sanger sequencing results for the nucleoporated cell populations verified correction of the sickle mutation in both populations of nucleoporated cells (FIG. 19). The sickle correction efficiency with T2wb-ssODN (FIG. 19B) was similar to the correction efficiency of the ssODN without wobble bases (FIG. 18). However, the sickle correction efficiency with T1 sgRNA and T1wb ssODN is lower than T2wb-ssODN, probably due to differences in sgRNA targeting efficiencies, distance from the sickle mutation to the sgRNA cleavage sites and the number of wobble bases. Therefore, T2wb-ssODN is the preferred ssODN.

Whole Genome Sequencing Analysis of EpcCas9 Corrected iPSC Colonies

To determine the specificity of EpcCas9 RNP directed correction of human sickle patient iPSCs, Whole Genome Sequencing (WGS) was performed on uncorrected sickle iPSC and 4 homozygous corrected clones were produced with TAT-Cas9WT-36GFP-INF7 RNP. Within the 4 corrected iPSC clones, 2 (T2-cl1 and T2-cl2) were corrected with T2 sgRNA and the 91-nt ssODN without wobble bases; 1 clone (T1w) was corrected with T2 sgRNA and a 95-nt T2wb ssODN and 1 clone (T1w) was corrected with T1 sgRNA and a 90-nt T1wb ssODN (Table 4). These WGS data confirmed homozygous correction of the sickle mutation and the absence of on-target indels in the 4 homozygous corrected iPSC clones (FIG. 20A). Analysis of 4720 potential off-target sites with homology to the T1 sgRNA and 1476 potential off-target sites with homology to the T2 sgRNA (1-5 mismatches) demonstrated no off-target modifications (FIG. 20B). Furthermore, analysis of the whole genome sequence data as described in Chang et al. (*Cell Reports* 12(10): 1668-77 (2015), demonstrated no disease-causing variants in sequences with or without homology to the sgRNAs. Four homozygous corrected clones were produced with TAT-Cas9WT-36GFP-INF7 RNP.

TABLE 4

Whole Genome Sequencing analysis of EpcCas9 corrected iPSC colonies

| Clone ID | Cas9 protein | sgRNA | sgRNA sequence | Wobble donor ssODN |
|---|---|---|---|---|
| T1w | | T1 | GGTCTGCCGTTACTGCCCTG SEQ ID NO 68 | T1 wobble |
| T2w | TAT-Cas9WT-36GFP-INF7 | T2 | GTAACGGCAGACTTCTCCAC SEQ ID NO 69 | T2 wobble |

TABLE 4-continued

Whole Genome Sequencing analysis of EpcCas9 corrected iPSC colonies

| Clone ID | Cas9 protein | sgRNA | sgRNA sequence | Wobble donor ssODN |
|---|---|---|---|---|
| T2-cl1 | | T2 | GTAACGGCAGACTTCTCCAC | No wobble |
| T2-cl2 | | T2 | GTAACGGCAGACTTCTCCAC | No wobble |

Gene Correction of Sickle Patient Bone Marrow CD34+ HSPCs

Figure 21:
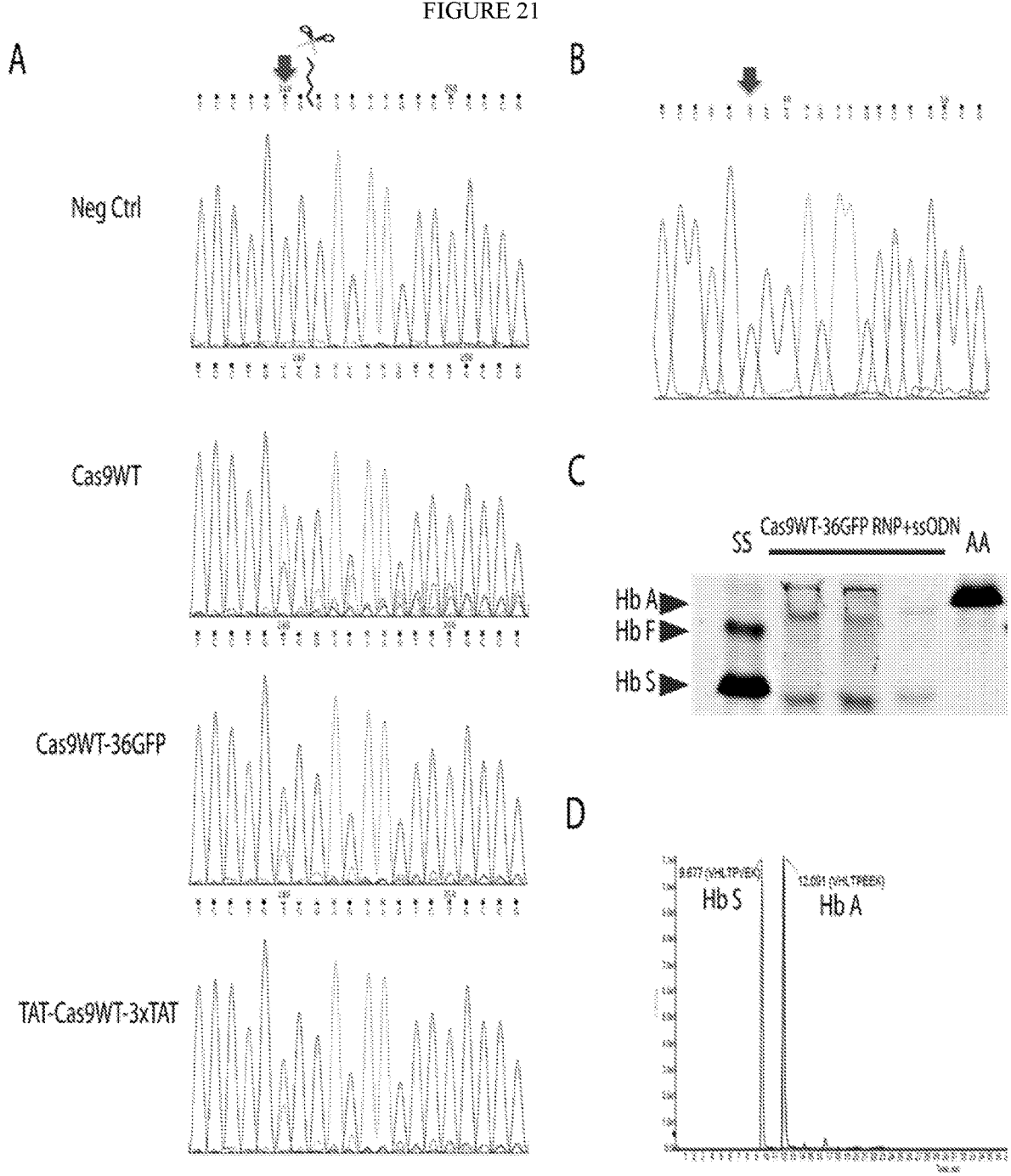
FIGS. 21A-D show gene correction of sickle patient bone marrow CD34+ HSPCs. (A) Human sickle bone marrow CD34+ cells were nucleoporated by Cas9WT, Cas9WT-36GFP and TAT-Cas9WT-3×TAT RNPs/ssODN. Gene correction efficiency for pooled populations cells was analyzed six days after nucleofection. The arrow indicates the position of sickle correction (T->A) and the scissor indicate the Cas9WT-36GFP RNP cutting site on the sickle HBB DNA. (B) mRNA correction by RT-PCR and Sanger sequencing in Cas9WT-36GFP nucleoporated sickle CD34+ cells that were harvested after 10-day culturing in erythroid differentiation media. (C) IEF Gel analysis of in vitro differentiated RBCs from Cas9WT-36GFP RNP/ssODN nucleofected sickle CD34+ cells. Human sickle child patient blood lysate (SS) and human normal adult blood lysate (AA) that represent HbF, HbS and HBA proteins were also loaded as controls. (D) Mass spectrometry analysis of in vitro differentiated RBCs derived from sickle CD34+ cells nucleofected with Cas9WT-36GFP RNP/ssODN. The peaks demonstrate signals from uncorrected HbS protein and corrected HbA protein.

Correction of primary CD34+ HSPCs from a sickle patient followed by autologous transplant is a powerful and simple approach for SCD gene therapy. To determine whether EpcCas9 RNP can also correct the sickle mutation in bone marrow progenitors, obtained CD34+ HSPCs were obtained from bone marrow of a consenting sickle cell patient. Sickle CD34+ cells were purified on anti-CD34 beads, and the cell cycle was activated by culture for 2 days in media with specific cytokines (SCF, TPO and FLT-3). Subsequently, the cells were nucleoporated with Cas9WT, Cas9-36GFP or TAT-Cas9-3×TAT plus T2 sgRNA and ssODN. The efficiency of sickle correction was determined 6 days after nucleoporation by the Sanger sequencing (FIG. 21A). The highest correction efficiency was obtained with Cas9WT; however, indel frequency was high. Although the correction efficiency with the 2 EpcCas9 RNPs was lower than with Cas9WT, the frequency of indels was dramatically lower.

Correction of the sickle mutation with one EpcCas9 (Cas9-36GFP) was verified at the mRNA and protein levels (FIG. 21B-D). After expansion of the nucleoporated cells in human erythroid expansion media for 10 days, RT-PCR and Sanger sequencing were performed (FIG. 21B). Approximately equal amounts of betaA and betaS mRNA were observed (peaks are essentially superimposed). Cells were also cultured in human erythroid differentiation media containing Erythropoietin (Epo) for 15-18 days. The red blood cells (RBCs) derived from this culture were lysed, and hemoglobins were resolved on an IEF gel (FIG. 21C). Approximately 35% of total hemoglobin was HbA (FIG. 21C), and this result was confirmed by mass spectrometry (FIG. 21D). In vivo, RBCs containing HbA survive 5-10 times longer than rbcs containing only HbS. Therefore, if about 30% of cells are corrected in the bone marrow after transplantation, HbA levels of 60-70% will be achieved in peripheral blood.

EpcCas9 RNPs Enhance the Correction/Indel Ratio in Sickle Patient Bone Marrow CD34+ HSPCs In addition to examining correction of the sickle mutation in populations of patient bone marrow CD34+ cells, we analyzed colonies derived from single CD34+ progenitors. After nucleoporation with TAT-Cas9WT-36GFP-INF7, CD34+ cells were mixed with semi-solid MethoCult media and plated into dishes. Two weeks after plating, colonies derived from single cells were isolated, DNA was extracted and Sanger sequence performed. The colonies that we examined were BFU-E (Burst Forming Units-Erythroid), CFU-E (Colony Forming Units-Erythroid) and CFU-GEMM (Colony Forming Units-Granulocyte, Erythrocyte, Monocyte, Megakaryocyte). FIG. 11 illustrates typical BFU-E and CFU-GEMM colonies (A) and representative Sanger Sequencing results of the six genotypes that were obtained (B). Table 5 summarizes of the Sanger sequencing results from 95, 96, and 96 colonies (BFU-E, CFU-E and CFU-GEMM) obtained after nucleoporation of Cas9WT, Cas9WT-36GFP, and TAT-Cas9WT-3×TAT RNPs and ssODNs, respectively. The highest correction efficiency was obtained with Cas9WT (51.6%); however, indel/indel frequency in cells treated with Cas9WT was also very high (40.0%). This level of indel/indel may result in beta-thalassemia because these HSCs will compete effectively for a limited number of bone marrow niches and red blood cells derived from these HSCs cannot synthesize HbA. Although the correction efficiency obtained with Cas9WT-36GFP RNP was lower (28.1%), this level of correction is sufficient to cure the disease as discussed above, and the frequency of indels (8.3%) is much safer. For TAT-Cas9WT-3×TAT RNP, the correction efficiency (32.3%) and indel frequency (14.6%) were intermediate. The correction/indel ratios after nucleoporation of Cas9WT, Cas9WT-36GFP, and TAT-Cas9WT-3×TAT RNPs plus ssODNs are 1.29 (51.6/40.0), 3.39 (28.1/8.3) and 2.21 (32.3/14.6), respectively. Therefore, Cas9WT-36GFP that has a correction/indel ratio of 3.39 is our preferred EpcCas9.

TABLE 5

Summary of the Sanger sequencing results from 95, 96, and 96 colonies (BFU-E, CFU-E and CFU-GEMM) obtained after nucleoporation of human sickle patient bone marrow CD34+ HSPC with Cas9WT, Cas9WT-36GFP, and TAT-Cas9WT-3xTAT RNPs and ssODNs, respectively.

| | Cas9WT RNP + ssODN | | Cas9WT-36GFP RNP + ssODN | | TAT-Cas9WT-3xTAT RNP + ssODN | |
|---|---|---|---|---|---|---|
| Total colonies | 95 | | 96 | | 96 | |
| GEMM/BFU-E/CFU-E colonies | 7/81/7 | | 16/80/0 | | 10/86/0 | |
| A/A | 13 | 18.9% | 3 | 3.1% | 10 | 10.4% |
| A/S | 2 | 2.1% | 14 | 14.6% | 4 | 4.2% |
| S/S | 5 | 5.3% | 46 | 47.9% | 27 | 28.1% |
| A/indel | 29 | 30.5% | 10 | 10.4% | 17 | 17.7% |
| S/indel | 3 | 3.2% | 15 | 15.6% | 24 | 25.0% |
| Indel/indel | 38 | 40.0% | 8 | 8.3% | 14 | 14.6% |
| Colonies with at least 1 allele corrected | 49 | 51.6% | 27 | 28.1% | 31 | 32.3% |
| Colonies with indels | 70 | 73.7% | 41 | 42.7% | 55 | 57.3% |
| Colonies with genome modification | 90 | 94.7% | 50 | 52.1% | 69 | 71.9% |

TABLE 5-continued

Summary of the Sanger sequencing results from 95, 96, and 96 colonies (BFU-E, CFU-E and CFU-GEMM) obtained after nucleoporation of human sickle patient bone marrow CD34+ HSPC with Cas9WT, Cas9WT-36GFP, and TAT-Cas9WT-3xTAT RNPs and ssODNs, respectively.

|  | Cas9WT RNP + ssODN | | Cas9WT-36GFP RNP + ssODN | | TAT-Cas9WT-3xTAT RNP + ssODN | |
|---|---|---|---|---|---|---|
| GEMM correction | 5 | 71.4% | 4 | 25.0% | 1 | 10.0% |
| Total number of alleles | 190 | | 192 | | 192 | |
| Total "A" alleles (corrected) | 67 | 35.3% | 30 | 15.6% | 41 | 21.4% |
| Total "S" alleles (uncorrected) | 15 | 7.9% | 121 | 63.7% | 82 | 43.2% |
| Total "indel" alleles | 108 | 56.8% | 41 | 21.6% | 69 | 36.3% |

As discussed above, the sickle correction efficiency of the Cas9WT-36GFP RNP/ssODN complex (28.1% of total CFU; 25% of CFU-GEMM) is high enough to cure the disease. This level of correction in the bone marrow after transplantation would result in 60-70% corrected RBC in peripheral blood. In addition, only 8.3% of colonies are homozygous indels (indel/indel); therefore, thalassemia is unlikely to result after transplantation.

EpcCas9 RNPs Enhance Cell Survival after Nucleoporation in Sickle Patient Bone Marrow CD34+ HSPCs The data in FIG. 22C demonstrate that EpcCas9 RNPs enhance cell survival after nucleoporation in sickle patient bone marrow CD34+ HSPCs. The number of erythroid colonies (BFU-E and CFU-E) obtained after nucleoporation of sickle patient bone marrow CD34+ HSPCs was compared with Cas9WT, Cas9WT-36GFP, and TAT-Cas9WT-3xTAT RNPs plus ssODNs. The number of colonies obtained with Cas9WT RPN/ssODN was normalized to 1. The number of colonies obtained with Cas9WT-36GFP RNP/ssODN was 2.5-fold higher than the Cas9WT control and TAT-Cas9WT-3xTAT RNP/ssODN was 1.6-fold higher. It was concluded that Epc (Engineered positive charge) protects human bone marrow progenitors/stem cells from the toxic effects of single stranded oligodeoxynucleotides (ssODNs).

These results are significant because the dose of CD34+ HPSCs is critical for bone marrow reconstitution after transplantation. In general, two million CD34+ cells/kg are transplanted into human recipients. Cell doses below this level result in poor long-term reconstitution. A 75 kg patient requires a dose of approximately 150 million cells. One liter of bone marrow can be harvested from a 75 kg patient under anesthesia and approximately 200 million CD34+ cells can be isolated for transplantation. As indicated above, 2.5-fold fewer cells are obtained after nucleoporation of CD34+ cells with Cas9WT RNP/ssODN compared to Cas9-36GFP RNP/ssODN. Therefore, our preferred complex for correction is Cas9WT-36GFP RNP/ssODN.

EpcCas9 Results in Higher Genome Editing Specificity

Figure 23:
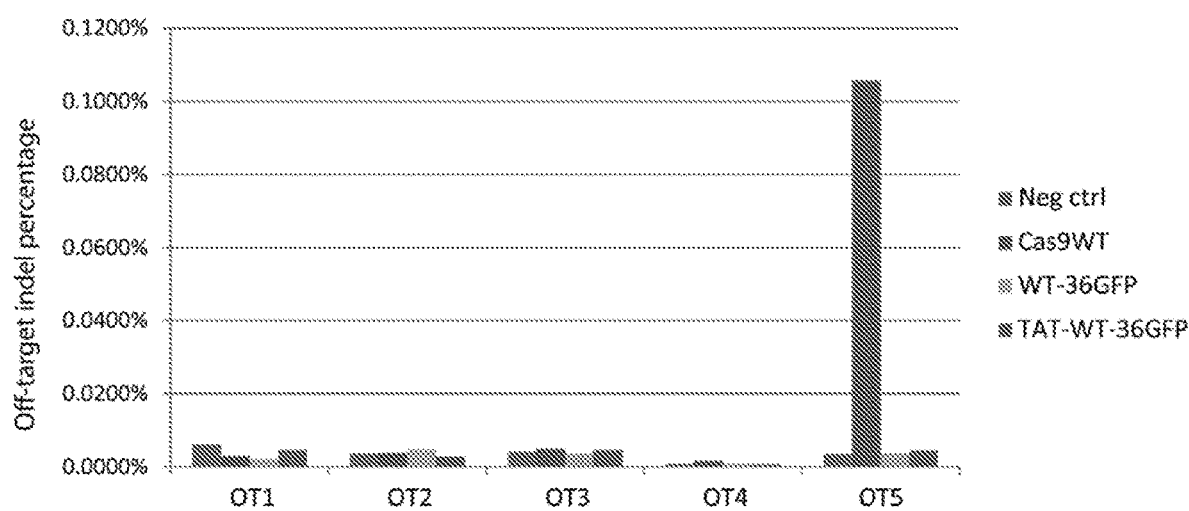
FIG. 23 is a graphical summary of deep sequencing data from Table 6.

To evaluate the specificity of genome editing by EpcCas9 RNPs in nucleoporated CD34+ cells, deep sequencing analysis was conducted at five potential off-target genomic loci. The five potential off-target sites were the top 5 sites predicted by the Zhang MIT server (http://crispr.mit.edu) based on sequence homology to the sgRNA. In Cas9 RNP/ssODN nucleoporated sickle patient CD34+ cells, deep sequencing measured approximately 0.1% off-target indels at OT5 site (Table 6). In contrast, in Cas9WT-36GFP or TAT-Cas9WT-3xTAT RNP/ssODN nucleoporated cells, no off-target modifications were observed (FIG. 23).

TABLE 6

Deep sequencing analysis of 5 potential off-target genomic loci to evaluate editing specificity of EpcCas9 RNPs in nucleoporated CD34+ cells

| | | OT1 chr3: 37684838 3MMs [1:5:7] | OT2 chr12: 112746615 3MMs [2:4:11] | OT3 chr11: 132762118 3MMs [2:5:19] | OT4 chr14: 101366447 4MMs [1:2:5:7] | OT5 chr10: 95158973 4MMs [1:2:3:7] |
|---|---|---|---|---|---|---|
| Neg ctrl | Indel reads | 13 | 34 | 28 | 4 | 8 |
| | Non-indel reads | 209990 | 900262 | 700844 | 449423 | 226882 |
| | Total reads | 210003 | 900296 | 700872 | 449427 | 226890 |
| | Indel percentage | 0.0062% | 0.0038% | 0.0040% | 0.0009% | 0.0035% |
| Cas9WT | Indel reads | 6 | 33 | 37 | 7 | 240 |
| | Non-indel reads | 199453 | 862095 | 754410 | 425039 | 226916 |
| | Total reads | 199459 | 862128 | 754447 | 425046 | 227156 |
| | Indel percentage | 0.0030% | 0.0038% | 0.0049% | 0.0016% | 0.1057% |
| Cas9WT-36GFP | Indel reads | 4 | 37 | 23 | 4 | 8 |
| | Non-indel reads | 189683 | 777630 | 615613 | 482843 | 207613 |
| | Total reads | 189687 | 777667 | 615636 | 482847 | 207621 |
| | Indel percentage | 0.0021% | 0.0048% | 0.0037% | 0.0008% | 0.0039% |
| TAT-Cas9WT-3xTAT | Indel reads | 9 | 24 | 32 | 3 | 9 |
| | Non-indel reads | 193690 | 843834 | 685044 | 458625 | 199515 |
| | Total reads | 193699 | 843858 | 685076 | 458628 | 199524 |
| | Indel percentage | 0.0046% | 0.0028% | 0.0047% | 0.0007% | 0.0045% |

In addition, in erythroid colonies derived from Cas9WT RNP/ssODN nucleoporated sickle CD34+ cells, 5 out of 95 colonies containing non-specific modifications near (upstream or downstream) the targeting site were observed (FIG. 24). These non-specific modifications are random gene replacements or indels that do not appear to be initiated at the expected Cas9 RNP cutting site. In contrast, 0 out of 96 colonies derived from EpcCas9 RNPs nucleoporated cells contain non-specific modifications.

Example 4

Correction of Sickle Cell Mutation in Mice

Figure 25:
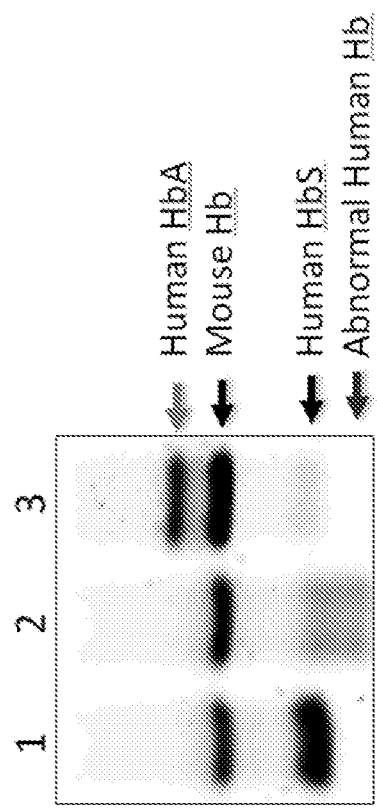
FIG. 25 shows isoelectric focusing (IEF) gel analysis of blood six weeks after primary transplantation of sickle mouse fetal liver c-kit+ cells nucleoporated with Cas9 RNP/ssODN into irradiated C57BI/6 mice to correct a sickle cell mutation. Mouse fetal liver c-kit+ cells are equivalent to human cord-blood Cd34+ cells.
Figure 26:
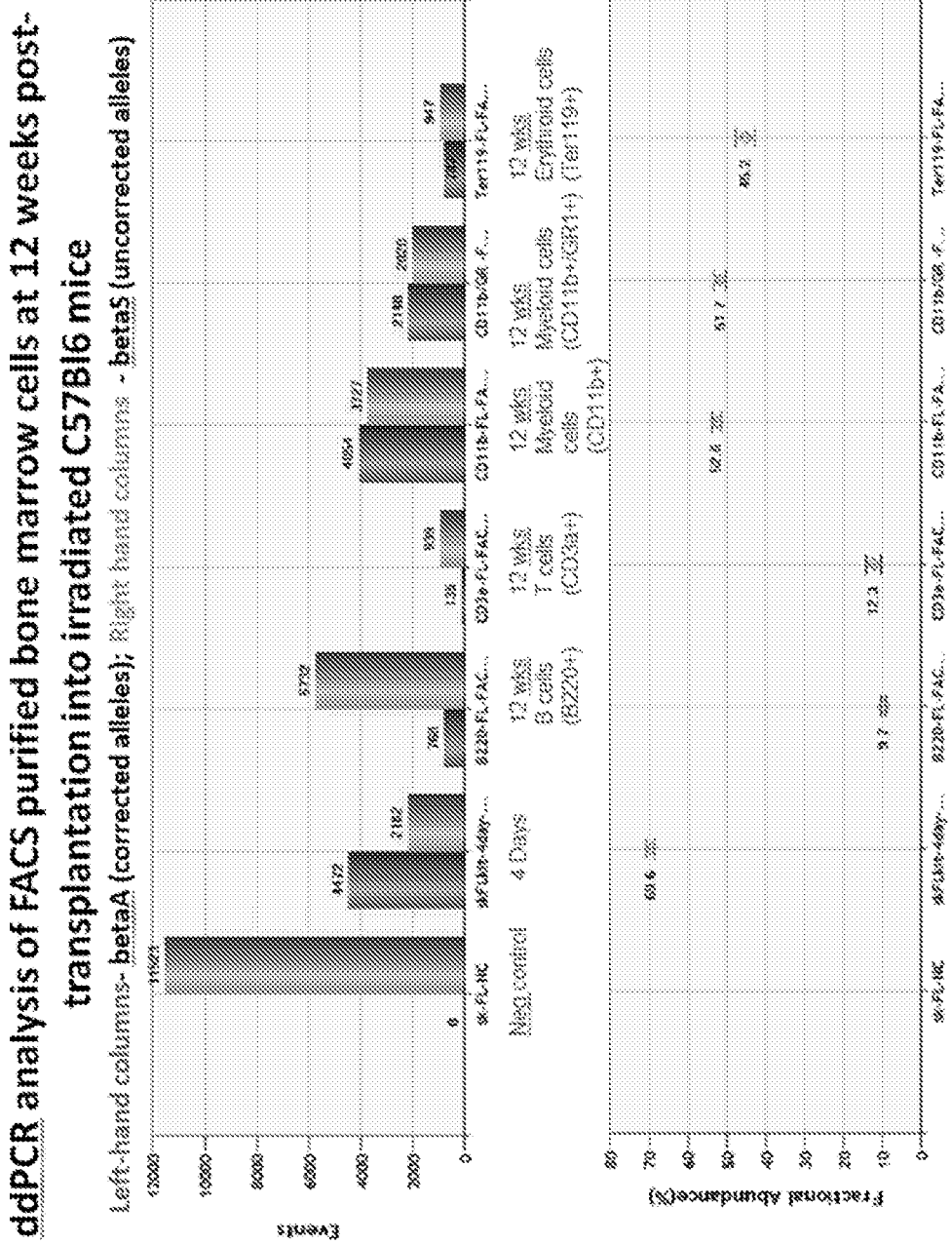
FIG. 26 shows ddPCR analysis of FACS purified bone marrow cells at twelve weeks post-transplantation into irradiated C57BI6 mice. Twelve weeks after nucleoporation and transplantation, approximately 50% of erythroid cells (Ter119+) and myeloid cells (CD11b+ and CD11b+/GR1+) are corrected. Erythroid and myeloid cells are relatively short lived; therefore, these cells are derived from transplanted HSCs. Correction levels in B and T cells can rise to approximately 50% after secondary transplantation at twelve weeks (twenty-four weeks total). After twenty-four weeks, most if not all hematopoietic cells will be derived from long-term HSCs.
Figure 27:
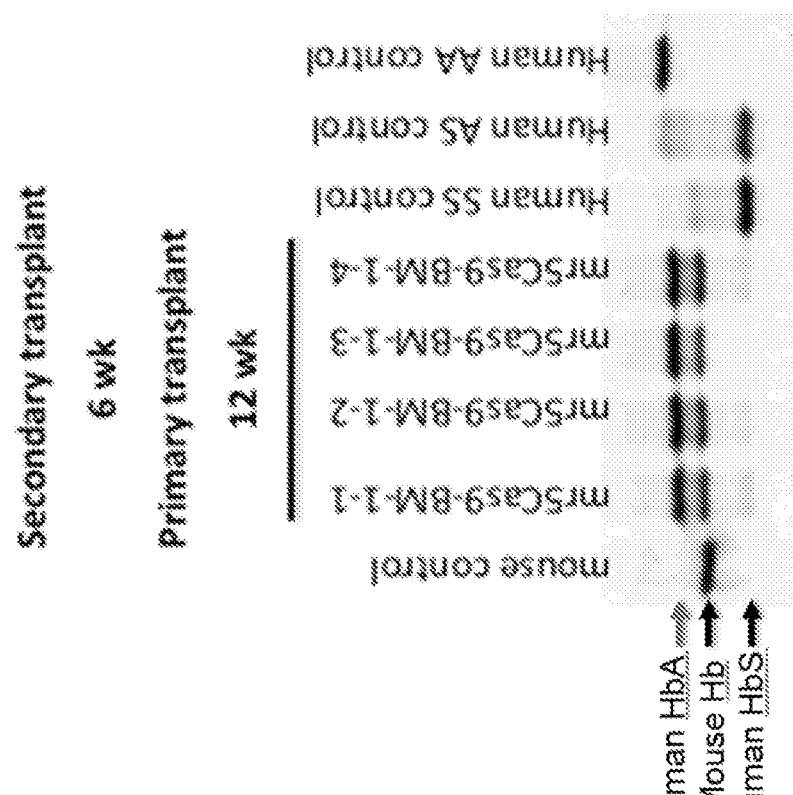
FIG. 27 shows IEF gel analysis of blood from mice twelve weeks after primary transplantation and six weeks after secondary transplantation of cells nucleoporated with Cas9 RNP/ssODN to correct a sickle cell mutation. Human HbA is produced in mice after transplantation of HSCs nucleoporated with Cas9 RNP/ssODN to correct a sickle cell mutation.

FIG. 25 shows an isoelectric focusing (IEF) gel analysis of blood six weeks after primary transplantation of Sickle Mouse Fetal Liver c-Kit+ cells nucleoporated with Cas9 RNP/ssODN to correct a sickle cell mutation. Mouse fetal liver c-kit+ cells are equivalent to human cord-blood Cd34+ cells. FIG. 26 shows ddPCR analysis of FACS purified bone marrow cells at twelve weeks post-transplantation into irradiated C57B16 mice. Twelve weeks after nucleoporation and transplantation, approximately 50% of erythroid cells (Ter119+) and myeloid cells (CD11b+ and CD11b+/GR1+) are corrected. Erythroid and myeloid cells are relatively short lived; therefore, these cells are derived from transplanted HSCs. Correction levels in B and T cells should rise to approximately 50% after secondary transplantation at twelve weeks (twenty-four weeks total). After twenty-four weeks, most if not all hematopoietic cells will be derived from long-term HSCs. FIG. 27 shows IEF gel analysis of the blood in mice twelve weeks after primary transplantation and six weeks after secondary transplantation of cells nucleoporated with Cas9 RNP/ssODN to correct a sickle cell mutation. Human HbA is produced in mice after transplantation of HSCs nucleoporated with Cas9 RNP/ssODN to correct a sickle cell mutation. The mouse hemoglobin band will disappear in six more weeks.

```
Sequences
                                                                     SEQ ID NO: 1
TAACGGCAGACTTCTCCAC

SEQ ID NO: 2
GTAACGGCAGACTTCTCCACGTTTTAGAGCTAGAAATAGCAAGTTAAAATAAGG

CTAGTCCGTTATCAACTTGAAAAAGTGGCACCGAGTCGGTGCTTTTTTT

Cas9-supercharged GFP construct
                                                                     SEQ ID NO: 3
mdykdhdgdykdhdidykddddkmapkkkrkvgihgvpaadkkysigldigtnsvgwavitdeykvpskkfkvlgntdrh sikknnligallfdsgetaeatrlkrtarrrytrrknricylqeifsnemakvddsffhrleesflveedkkherhpifgnivdevayhek yptiyhlrkklvdstdkadlrliylalahmikfrghfliegdlnpdnsdvdklfiqlvqtynqlfeenpinasgvdakailsarlsksrrl enliaqlpgekknglfgnlialslgltpnfksnfdlaedaklqlskdtydddldnllaqigdqyadlflaaknlsdaillsdilrvnteitk aplsasmikrydehhqdltllkalvrqqlpekykeiffdqskngyagyidggasqeefykfikpilekmdgteellvklnredllrk qrtfdngsiphqihlgelhailrrqedfypflkdnrekiekiltfripyyvgplargnsrfawmtrkseetitpwnfeevvdkgasaqs fiermtnfdknlpnekvlpkhsllyeyftvyneltkvkyvtegmrkpaflsgeqkkaivdllfktnrkvtvkqlkedyfkkiecfds veisgvedrfnaslgtyhdllkiikdkdfldneenediledivltltlfedremieerlktyahlfddkvmkqlkrrrytgwgrlsrkli ngirdkqsgktildflksdgfanrnfmqlihddsltfkediqkaqvsgqgdslhehianlagspaikkgilqtvkvvdelvkvmgr hkpeniviemarenqttqkgqknsrermkrieegikelgsqilkehpventqlqneklylyylqngrdmyvdqeldinrlsdydv dhivpqsflkddsidnkvltrsdknrgksdnvpseevvkkmknywrqllnaklitqrkfdnltkaergglseldkagfikrqlvetr qitkhvaqildsrmntkydendklirevkvitlksklvsdfrkdfqfykvreinnyhhahdaylnavvgtalikkypklesefvyg dykvydvrkmiakseqeigkatakyffysnimnffkteitlangeirkrplietngetgeivwdkgrdfatvrkvlsmpqvnivkk tevqtggfskesilpkrnsdkliarkkdwdpkkyggfdsptvaysvlvvakvekgkskklksvkellgitimerssfeknpidfle akgykevkkdliiklpkyslfelengrkrmlasagelqkgnelalpskyvnflylashyeklkgspedneqkqlfveqhkhyldei ieqisefskrviladanldkvlsaynkhrdkpireqaeniihlftltnlgapaafkyfdttidrkrytstkevldatlihqsitglyetridls qlggdkrpaatkkagqakkkkgsgsngssgsaskgerlfrgkvpilvelkgdvnghkfsvrgkgkgdatrgkltlkficttgklpv pwptlvttltygvqcfsrypkhmkrhdffksampkgyvqertisfkkdgkyktraevkfegrtlvnriklkgrdfkekgnilghkl rynfnshkvyitadkrkngikakfkirhnvkdgsvqladhyqqntpigrgpvllprnhylstrsklskdpkekrdhmvllefvtaa gikhgrderyk TAT-Cas9-supercharged GFP construct
                                                                     SEQ ID NO: 4
ygrkkrrqrrrppqaggsmdykdhdgdykdhdidykddddkmapkkkrkvgihgvpaadkkysigldigtnsvgwavitd eykvpskkfkvlgntdrhsikknnligallfdsgetaeatrlkrtarrrytrrknricylqeifsnemakvddsffhrleesflveedkkh erhpifgnivdevayhekyptiyhlrkklvdstdkadlrliylalahmikfrghfliegdlnpdnsdvdklfiqlvqtynqlfeenpin
```

-continued asgvdakailsarlsksrrlenliaqlpgekknglfgnlialslgltpnfksnfdlaedaklqlskdtydddldnllaqigdqyadlflaa knlsdaillsdilrvnteitkaplsasmikrydehhqdltllkalvrqqlpekykeiffdqskngyagyidggasqeefykfikpilek mdgteellvklnredllrkqrtfdngsiphqihlgelhailrrqedfypflkdnrekiekiltfripyyvgplargnsrfawmtrkseet itpwnfeevvdkgasaqsfiermtnfdknlpnekvlpkhsllyeyftvyneltkvkyvtegmrkpaflsgeqkkaivdllfktnrk vtvkqlkedyfkkiecfdsveisgvedrfnaslgtyhdllkiikdkdfldneenediledivltltlfedremieerlktyahlfddkv mkqlkrrrytgwgrlsrklingirdkqsgktildflksdgfanrnfmqlihddsltfkediqkaqvsgqgdslhehianlagspaikk gilqtvkvvdelvkvmgrhkpeniviemarenqttqkgqknsrermkrieegikelgsqilkehpventqlqneklylyylqngr dmyvdqeldinrlsdydvdhivpqsflkddsidnkvltrsdknrgksdnvpseevvkkmknywrqllnaklitqrkfdnitkaer gglseldkagfikrqlvetrqitkhvaqildsrmntkydendklirevkvitlksklvsdfrkdfqfykvreinnyhhahdaylnavv gtalikkypkleseefvygdykvydvrkmiakseqeigkatakyffysnimnffkteitlangeirkrplietngetgeivwdkgrdf atvrkvlsmpqvnivkktevqtggfskesilpkrnsdkliarkkdwdpkkyggfdsptvaysvlvvakvekgskklksvkell gitimerssfeknpidfleakgykevkkdliiklpkyslfelengrkrmlasagelqkgnelalpskyvnflylashyeklkgsped neqkqlfveqhkhyldeiieqisefskrviladanldkvlsaynkhrdkpireqaeniihlftltnlgapaafkyfdttidrkrytstke vldatlihqsitglyetridlsqlggdkrpaatkkagqakkkkgsgsngssgsaskgerlfrgkvpilvelkgdvnghkfsvrgkgk gdatrgkltlkficttgklpvpwptlvttltygvqcfsrypkhmkrhdffksampkgyvqertisfkkdgkyktraevkfegrtlvnr iklkgrdfkekgnilghklrynfnshkvyitadkrkngikakfkirhnvkdgsvqladhyqqntpigrgpvllprnhylstrsklsk dpkekrdhmvllefvtaagikhgrderykggsggsvdglfeaiegfiengwegmidgwyg

---

What is claimed is:

1. A complex for correcting a mutation associated with sickle cell anemia in the genome of a CD34+ human stem/progenitor cell (HSPC) comprising:
   a. a guide RNA (gRNA) comprising a first nucleotide sequence that hybridizes to a target DNA in the genome of the CD34+ HSPC, wherein the target DNA comprises the mutation associated with sickle cell anemia, and a second nucleotide sequence that interacts with a site-directed nuclease;
   b. a recombinant site-directed nuclease operably linked to a superpositively charged protein, wherein the site-directed nuclease comprises an RNA-binding portion that interacts with the second nucleotide sequence of the guide RNA and wherein the site-directed nuclease specifically binds and cleaves the target DNA to create a double stranded break, wherein the superpositively charged protein is a superpositively charged green fluorescent protein (GFP) that has an overall positive charge from about +5 to about +40, and wherein the superpositively charged protein is operably linked to the carboxy-terminus of the site-directed nuclease; and
   c. a single-stranded donor oligonucleotide (ssODN) that hybridizes to a genomic sequence flanking the double stranded break in the target DNA and integrates into the target DNA to correct mutation associated with sickle cell anemia in the target DNA.

2. The complex of claim 1, wherein the ssODN that hybridizes to the genomic sequence flanking the double stranded break in the target DNA is a template for homology directed repair of the mutation in the target DNA.

3. The complex of claim 1, wherein the ssODN hybridizes to the genomic sequence encoding hemoglobin.

4. The complex of claim 1, wherein the nuclease is Cas9.

5. The complex of claim 1, wherein the molar ratio of gRNA to site-directed nuclease operably linked to a superpositively charged protein to ssODN is from about 1:1:0.2 to about 1.5:1:2.0.

6. A CD34+ HSPC cell comprising the complex of claim 1.

7. A method of correcting a mutation associated with sickle cell anemia in a population of CD34+ HSPCs comprising introducing into the CD34+ the complex of claim 1, wherein the complex is introduced into the cells under conditions that allow homology-directed repair (HDR) and integration of the ssODN into the target DNA.

8. The method of claim 7, wherein the ratio of homology-directed repair to nonhomologous end joining (NHEJ) in the population of cells is from about 10 to about 0.5.

9. The method of claim 7, wherein the mutation is corrected in at least 5% of the cells.

10. The method of claim 9, wherein the cell survival rate for corrected cells is at least about 50%.

11. The complex of claim 1, wherein the CD34+ HSPC is a CD34+ peripheral blood HSPC, a CD34+ bone marrow HSPC or a CD34+ cord blood HSPC.

12. The complex of claim 1, wherein, following introduction of the complex into a population of CD34+ HSPCs, at least 50% of the CD34+ HSPCs are viable.

13. The complex of claim 1, wherein at least 5% of a population of CD34+ HSPCs, after introducing the complex into the population of the CD34+ HSPCs comprising a mutation associated with sickle cell anemia, comprise a corrected mutation.

14. The complex of claim 13, wherein at least 20% of a population of CD34+ HSPCs, after introducing the complex into the population of the CD34+ HSPCs comprising a mutation associated with sickle cell anemia, comprises a corrected mutation.

15. The complex of claim 1, wherein, after introducing the complex into a population of CD34+ HSPCs comprising a mutation associated with sickle cell anemia, the ratio of homology-directed repair to nonhomologous end joining in the population of CD34+ HSPCs is at least about 0.5.

* * * * *

UNITED STATES PATENT AND TRADEMARK OFFICE
CERTIFICATE OF CORRECTION

| | | |
|---|---|---|
| PATENT NO. | : 11,643,668 B2 | Page 1 of 1 |
| APPLICATION NO. | : 15/737132 | |
| DATED | : May 9, 2023 | |
| INVENTOR(S) | : Tim Townes, Lei Ding and Chia-Wei Chang | |

It is certified that error appears in the above-identified patent and that said Letters Patent is hereby corrected as shown below:

In the Claims

Column 82, Line 59, Delete:
"introducing into the CD34+ the complex of claim 1,"

And Insert:
--introducing into the CD34+ HSPCs the complex of claim 1,--

Signed and Sealed this
Seventh Day of November, 2023

Katherine Kelly Vidal
*Director of the United States Patent and Trademark Office*

SEQUENCE LISTING

<160> NUMBER OF SEQ ID NOS: 69

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
taacggcaga cttctccac                                            19

<210> SEQ ID NO 2
<211> LENGTH: 103
<212> TYPE: DNA
<213> ORGANISM: Artificial sequence
<220> FEATURE:
<223> OTHER INFORMATION: Synthetic construct

<400> SEQUENCE: 2
gtaacggcag acttctccac gttttagagc tagaaatagc aagttaaaat aaggctagtc    60
cgttatcaac ttgaaaaagt ggcaccgagt cggtgctttt ttt                    103

<210> SEQ ID NO 3
<211> LENGTH: 1671
<212> TYPE: PRT
<213> ORGANISM: Artificial sequence
<220> FEATURE:
<223> OTHER INFORMATION: SEQ ID NO: 4

<400> SEQUENCE: 3

Met Asp Tyr Lys Asp His Asp Gly Asp Tyr Lys Asp His Asp Ile Asp
1               5                   10                  15

```
Tyr Lys Asp Asp Asp Lys Met Ala Pro Lys Lys Arg Lys Val
            20              25              30

Gly Ile His Gly Val Pro Ala Ala Asp Lys Lys Tyr Ser Ile Gly Leu
        35              40              45

Asp Ile Gly Thr Asn Ser Val Gly Trp Ala Val Ile Thr Asp Glu Tyr
        50              55              60

Lys Val Pro Ser Lys Lys Phe Lys Val Leu Gly Asn Thr Asp Arg His
65              70              75              80

Ser Ile Lys Lys Asn Leu Ile Gly Ala Leu Leu Phe Asp Ser Gly Glu
                85              90              95

Thr Ala Glu Ala Thr Arg Leu Lys Arg Thr Ala Arg Arg Arg Tyr Thr
            100             105             110

Arg Arg Lys Asn Arg Ile Cys Tyr Leu Gln Glu Ile Phe Ser Asn Glu
        115             120             125

Met Ala Lys Val Asp Asp Ser Phe Phe His Arg Leu Glu Glu Ser Phe
130             135             140

Leu Val Glu Glu Asp Lys Lys His Glu Arg His Pro Ile Phe Gly Asn
145             150             155             160

Ile Val Asp Glu Val Ala Tyr His Glu Lys Tyr Pro Thr Ile Tyr His
                165             170             175

Leu Arg Lys Lys Leu Val Asp Ser Thr Asp Lys Ala Asp Leu Arg Leu
            180             185             190

Ile Tyr Leu Ala Leu Ala His Met Ile Lys Phe Arg Gly His Phe Leu
        195             200             205

Ile Glu Gly Asp Leu Asn Pro Asp Asn Ser Asp Val Asp Lys Leu Phe
        210             215             220

Ile Gln Leu Val Gln Thr Tyr Asn Gln Leu Phe Glu Glu Asn Pro Ile
225             230             235             240

Asn Ala Ser Gly Val Asp Ala Lys Ala Ile Leu Ser Ala Arg Leu Ser
                245             250             255

Lys Ser Arg Arg Leu Glu Asn Leu Ile Ala Gln Leu Pro Gly Glu Lys
            260             265             270

Lys Asn Gly Leu Phe Gly Asn Leu Ile Ala Leu Ser Leu Gly Leu Thr
        275             280             285

Pro Asn Phe Lys Ser Asn Phe Asp Leu Ala Glu Asp Ala Lys Leu Gln
        290             295             300

Leu Ser Lys Asp Thr Tyr Asp Asp Asp Leu Asp Asn Leu Leu Ala Gln
305             310             315             320

Ile Gly Asp Gln Tyr Ala Asp Leu Phe Leu Ala Ala Lys Asn Leu Ser
                325             330             335

Asp Ala Ile Leu Leu Ser Asp Ile Leu Arg Val Asn Thr Glu Ile Thr
            340             345             350

Lys Ala Pro Leu Ser Ala Ser Met Ile Lys Arg Tyr Asp Glu His His
        355             360             365

Gln Asp Leu Thr Leu Leu Lys Ala Leu Val Arg Gln Gln Leu Pro Glu
        370             375             380

Lys Tyr Lys Glu Ile Phe Phe Asp Gln Ser Lys Asn Gly Tyr Ala Gly
385             390             395             400

Tyr Ile Asp Gly Gly Ala Ser Gln Glu Glu Phe Tyr Lys Phe Ile Lys
                405             410             415

Pro Ile Leu Glu Lys Met Asp Gly Thr Glu Glu Leu Leu Val Lys Leu
            420             425             430

Asn Arg Glu Asp Leu Leu Arg Lys Gln Arg Thr Phe Asp Asn Gly Ser
```

```
              435                 440                 445
Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
        530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
        690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
        835                 840                 845

Lys Leu Tyr Leu Tyr Tyr Leu Gln Asn Gly Arg Asp Met Tyr Val Asp
    850                 855                 860
```

```
Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys  Leu Val Ser Asp Phe  Arg Lys Asp
        995                 1000                1005

Phe Gln Phe Tyr Lys Val Arg  Glu Ile Asn Asn Tyr  His His Ala
    1010                1015                1020

His Asp Ala Tyr Leu Asn Ala  Val Val Gly Thr Ala  Leu Ile Lys
    1025                1030                1035

Lys Tyr Pro Lys Leu Glu Ser  Glu Phe Val Tyr Gly  Asp Tyr Lys
    1040                1045                1050

Val Tyr Asp Val Arg Lys Met  Ile Ala Lys Ser Glu  Gln Glu Ile
    1055                1060                1065

Gly Lys Ala Thr Ala Lys Tyr  Phe Phe Tyr Ser Asn  Ile Met Asn
    1070                1075                1080

Phe Phe Lys Thr Glu Ile Thr  Leu Ala Asn Gly Glu  Ile Arg Lys
    1085                1090                1095

Arg Pro Leu Ile Glu Thr Asn  Gly Glu Thr Gly Glu  Ile Val Trp
    1100                1105                1110

Asp Lys Gly Arg Asp Phe Ala  Thr Val Arg Lys Val  Leu Ser Met
    1115                1120                1125

Pro Gln Val Asn Ile Val Lys  Lys Thr Glu Val Gln  Thr Gly Gly
    1130                1135                1140

Phe Ser Lys Glu Ser Ile Leu  Pro Lys Arg Asn Ser  Asp Lys Leu
    1145                1150                1155

Ile Ala Arg Lys Lys Asp Trp  Asp Pro Lys Lys Tyr  Gly Gly Phe
    1160                1165                1170

Asp Ser Pro Thr Val Ala Tyr  Ser Val Leu Val Val  Ala Lys Val
    1175                1180                1185

Glu Lys Gly Lys Ser Lys Lys  Leu Lys Ser Val Lys  Glu Leu Leu
    1190                1195                1200

Gly Ile Thr Ile Met Glu Arg  Ser Ser Phe Glu Lys  Asn Pro Ile
    1205                1210                1215

Asp Phe Leu Glu Ala Lys Gly  Tyr Lys Glu Val Lys  Lys Asp Leu
    1220                1225                1230

Ile Ile Lys Leu Pro Lys Tyr  Ser Leu Phe Glu Leu  Glu Asn Gly
    1235                1240                1245

Arg Lys Arg Met Leu Ala Ser  Ala Gly Glu Leu Gln  Lys Gly Asn
    1250                1255                1260
```

-continued

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asp Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Gly Ser Gly Ser Asn
1415                1420                1425

Gly Ser Ser Gly Ser Ala Ser Lys Gly Glu Arg Leu Phe Arg Gly
1430                1435                1440

Lys Val Pro Ile Leu Val Glu Leu Lys Gly Asp Val Asn Gly His
1445                1450                1455

Lys Phe Ser Val Arg Gly Lys Gly Lys Gly Asp Ala Thr Arg Gly
1460                1465                1470

Lys Leu Thr Leu Lys Phe Ile Cys Thr Thr Gly Lys Leu Pro Val
1475                1480                1485

Pro Trp Pro Thr Leu Val Thr Thr Leu Thr Tyr Gly Val Gln Cys
1490                1495                1500

Phe Ser Arg Tyr Pro Lys His Met Lys Arg His Asp Phe Phe Lys
1505                1510                1515

Ser Ala Met Pro Lys Gly Tyr Val Gln Glu Arg Thr Ile Ser Phe
1520                1525                1530

Lys Lys Asp Gly Lys Tyr Lys Thr Arg Ala Glu Val Lys Phe Glu
1535                1540                1545

Gly Arg Thr Leu Val Asn Arg Ile Lys Leu Lys Gly Arg Asp Phe
1550                1555                1560

Lys Glu Lys Gly Asn Ile Leu Gly His Lys Leu Arg Tyr Asn Phe
1565                1570                1575

Asn Ser His Lys Val Tyr Ile Thr Ala Asp Lys Arg Lys Asn Gly
1580                1585                1590

Ile Lys Ala Lys Phe Lys Ile Arg His Asn Val Lys Asp Gly Ser
1595                1600                1605

Val Gln Leu Ala Asp His Tyr Gln Gln Asn Thr Pro Ile Gly Arg
1610                1615                1620

Gly Pro Val Leu Leu Pro Arg Asn His Tyr Leu Ser Thr Arg Ser
1625                1630                1635

Lys Leu Ser Lys Asp Pro Lys Glu Lys Arg Asp His Met Val Leu
1640                1645                1650

Leu Glu Phe Val Thr Ala Ala Gly Ile Lys His Gly Arg Asp Glu

Arg Tyr Lys
    1670

<210> SEQ ID NO 4
<211> LENGTH: 1720
<212> TYPE: PRT
<213> ORGANISM: Artificial sequence
<220> FEATURE:
<223> OTHER INFORMATION: Synthetic construct

<400> SEQUENCE: 4

Tyr Gly Arg Lys Lys Arg Gln Arg Arg Pro Pro Gln Ala Gly
1               5                   10                  15

Gly Ser Met Asp Tyr Lys Asp His Asp Gly Asp Tyr Lys Asp His Asp
            20                  25                  30

Ile Asp Tyr Lys Asp Asp Asp Lys Met Ala Pro Lys Lys Arg
            35                  40                  45

Lys Val Gly Ile His Gly Val Pro Ala Ala Asp Lys Lys Tyr Ser Ile
50                  55                  60

Gly Leu Asp Ile Gly Thr Asn Ser Val Gly Trp Ala Val Ile Thr Asp
65                  70                  75                  80

Glu Tyr Lys Val Pro Ser Lys Lys Phe Lys Val Leu Gly Asn Thr Asp
                85                  90                  95

Arg His Ser Ile Lys Lys Asn Leu Ile Gly Ala Leu Leu Phe Asp Ser
                100                 105                 110

Gly Glu Thr Ala Glu Ala Thr Arg Leu Lys Arg Thr Ala Arg Arg Arg
            115                 120                 125

Tyr Thr Arg Arg Lys Asn Arg Ile Cys Tyr Leu Gln Glu Ile Phe Ser
130                 135                 140

Asn Glu Met Ala Lys Val Asp Asp Ser Phe Phe His Arg Leu Glu Glu
145                 150                 155                 160

Ser Phe Leu Val Glu Glu Asp Lys Lys His Glu Arg His Pro Ile Phe
                165                 170                 175

Gly Asn Ile Val Asp Glu Val Ala Tyr His Glu Lys Tyr Pro Thr Ile
            180                 185                 190

Tyr His Leu Arg Lys Lys Leu Val Asp Ser Thr Asp Lys Ala Asp Leu
        195                 200                 205

Arg Leu Ile Tyr Leu Ala Leu Ala His Met Ile Lys Phe Arg Gly His
    210                 215                 220

Phe Leu Ile Glu Gly Asp Leu Asn Pro Asp Asn Ser Asp Val Asp Lys
225                 230                 235                 240

Leu Phe Ile Gln Leu Val Gln Thr Tyr Asn Gln Leu Phe Glu Glu Asn
                245                 250                 255

Pro Ile Asn Ala Ser Gly Val Asp Ala Lys Ala Ile Leu Ser Ala Arg
            260                 265                 270

Leu Ser Lys Ser Arg Arg Leu Glu Asn Leu Ile Ala Gln Leu Pro Gly
        275                 280                 285

Glu Lys Lys Asn Gly Leu Phe Gly Asn Leu Ile Ala Leu Ser Leu Gly
    290                 295                 300

Leu Thr Pro Asn Phe Lys Ser Asn Phe Asp Leu Ala Glu Asp Ala Lys
305                 310                 315                 320

Leu Gln Leu Ser Lys Asp Thr Tyr Asp Asp Asp Leu Asp Asn Leu Leu
                325                 330                 335

Ala Gln Ile Gly Asp Gln Tyr Ala Asp Leu Phe Leu Ala Ala Lys Asn

```
                340                 345                 350
Leu Ser Asp Ala Ile Leu Leu Ser Asp Ile Leu Arg Val Asn Thr Glu
            355                 360                 365

Ile Thr Lys Ala Pro Leu Ser Ala Ser Met Ile Lys Arg Tyr Asp Glu
            370                 375                 380

His His Gln Asp Leu Thr Leu Leu Lys Ala Leu Val Arg Gln Gln Leu
385                 390                 395                 400

Pro Glu Lys Tyr Lys Glu Ile Phe Phe Asp Gln Ser Lys Asn Gly Tyr
                405                 410                 415

Ala Gly Tyr Ile Asp Gly Gly Ala Ser Gln Glu Glu Phe Tyr Lys Phe
            420                 425                 430

Ile Lys Pro Ile Leu Glu Lys Met Asp Gly Thr Glu Glu Leu Leu Val
            435                 440                 445

Lys Leu Asn Arg Glu Asp Leu Leu Arg Lys Gln Arg Thr Phe Asp Asn
        450                 455                 460

Gly Ser Ile Pro His Gln Ile His Leu Gly Glu Leu His Ala Ile Leu
465                 470                 475                 480

Arg Arg Gln Glu Asp Phe Tyr Pro Phe Leu Lys Asp Asn Arg Glu Lys
                485                 490                 495

Ile Glu Lys Ile Leu Thr Phe Arg Ile Pro Tyr Tyr Val Gly Pro Leu
            500                 505                 510

Ala Arg Gly Asn Ser Arg Phe Ala Trp Met Thr Arg Lys Ser Glu Glu
            515                 520                 525

Thr Ile Thr Pro Trp Asn Phe Glu Glu Val Val Asp Lys Gly Ala Ser
        530                 535                 540

Ala Gln Ser Phe Ile Glu Arg Met Thr Asn Phe Asp Lys Asn Leu Pro
545                 550                 555                 560

Asn Glu Lys Val Leu Pro Lys His Ser Leu Leu Tyr Glu Tyr Phe Thr
                565                 570                 575

Val Tyr Asn Glu Leu Thr Lys Val Lys Tyr Val Thr Glu Gly Met Arg
            580                 585                 590

Lys Pro Ala Phe Leu Ser Gly Glu Gln Lys Lys Ala Ile Val Asp Leu
            595                 600                 605

Leu Phe Lys Thr Asn Arg Lys Val Thr Val Lys Gln Leu Lys Glu Asp
        610                 615                 620

Tyr Phe Lys Lys Ile Glu Cys Phe Asp Ser Val Glu Ile Ser Gly Val
625                 630                 635                 640

Glu Asp Arg Phe Asn Ala Ser Leu Gly Thr Tyr His Asp Leu Leu Lys
                645                 650                 655

Ile Ile Lys Asp Lys Asp Phe Leu Asp Asn Glu Glu Asn Glu Asp Ile
            660                 665                 670

Leu Glu Asp Ile Val Leu Thr Leu Thr Leu Phe Glu Asp Arg Glu Met
            675                 680                 685

Ile Glu Glu Arg Leu Lys Thr Tyr Ala His Leu Phe Asp Asp Lys Val
        690                 695                 700

Met Lys Gln Leu Lys Arg Arg Tyr Thr Gly Trp Gly Arg Leu Ser
705                 710                 715                 720

Arg Lys Leu Ile Asn Gly Ile Arg Asp Lys Gln Ser Gly Lys Thr Ile
                725                 730                 735

Leu Asp Phe Leu Lys Ser Asp Gly Phe Ala Asn Arg Asn Phe Met Gln
            740                 745                 750

Leu Ile His Asp Asp Ser Leu Thr Phe Lys Glu Asp Ile Gln Lys Ala
        755                 760                 765
```

```
Gln Val Ser Gly Gln Gly Asp Ser Leu His Glu His Ile Ala Asn Leu
    770                 775                 780

Ala Gly Ser Pro Ala Ile Lys Lys Gly Ile Leu Gln Thr Val Lys Val
785                 790                 795                 800

Val Asp Glu Leu Val Lys Val Met Gly Arg His Lys Pro Glu Asn Ile
                805                 810                 815

Val Ile Glu Met Ala Arg Glu Asn Gln Thr Thr Gln Lys Gly Gln Lys
                820                 825                 830

Asn Ser Arg Glu Arg Met Lys Arg Ile Glu Glu Gly Ile Lys Glu Leu
        835                 840                 845

Gly Ser Gln Ile Leu Lys Glu His Pro Val Glu Asn Thr Gln Leu Gln
    850                 855                 860

Asn Glu Lys Leu Tyr Leu Tyr Tyr Leu Gln Asn Gly Arg Asp Met Tyr
865                 870                 875                 880

Val Asp Gln Glu Leu Asp Ile Asn Arg Leu Ser Asp Tyr Asp Val Asp
                885                 890                 895

His Ile Val Pro Gln Ser Phe Leu Lys Asp Asp Ser Ile Asp Asn Lys
                900                 905                 910

Val Leu Thr Arg Ser Asp Lys Asn Arg Gly Lys Ser Asp Asn Val Pro
                915                 920                 925

Ser Glu Glu Val Val Lys Lys Met Lys Asn Tyr Trp Arg Gln Leu Leu
    930                 935                 940

Asn Ala Lys Leu Ile Thr Gln Arg Lys Phe Asp Asn Leu Thr Lys Ala
945                 950                 955                 960

Glu Arg Gly Gly Leu Ser Glu Leu Asp Lys Ala Gly Phe Ile Lys Arg
                965                 970                 975

Gln Leu Val Glu Thr Arg Gln Ile Thr Lys His Val Ala Gln Ile Leu
                980                 985                 990

Asp Ser Arg Met Asn Thr Lys Tyr Asp Glu Asn Asp Lys Leu Ile Arg
        995                 1000                1005

Glu Val Lys Val Ile Thr Leu Lys Ser Lys Leu Val Ser Asp Phe
    1010                1015                1020

Arg Lys Asp Phe Gln Phe Tyr Lys Val Arg Glu Ile Asn Asn Tyr
    1025                1030                1035

His His Ala His Asp Ala Tyr Leu Asn Ala Val Val Gly Thr Ala
    1040                1045                1050

Leu Ile Lys Lys Tyr Pro Lys Leu Glu Ser Glu Phe Val Tyr Gly
    1055                1060                1065

Asp Tyr Lys Val Tyr Asp Val Arg Lys Met Ile Ala Lys Ser Glu
    1070                1075                1080

Gln Glu Ile Gly Lys Ala Thr Ala Lys Tyr Phe Phe Tyr Ser Asn
    1085                1090                1095

Ile Met Asn Phe Phe Lys Thr Glu Ile Thr Leu Ala Asn Gly Glu
    1100                1105                1110

Ile Arg Lys Arg Pro Leu Ile Glu Thr Asn Gly Glu Thr Gly Glu
    1115                1120                1125

Ile Val Trp Asp Lys Gly Arg Asp Phe Ala Thr Val Arg Lys Val
    1130                1135                1140

Leu Ser Met Pro Gln Val Asn Ile Val Lys Lys Thr Glu Val Gln
    1145                1150                1155

Thr Gly Gly Phe Ser Lys Glu Ser Ile Leu Pro Lys Arg Asn Ser
    1160                1165                1170
```

```
Asp Lys Leu Ile Ala Arg Lys Lys Asp Trp Asp Pro Lys Lys Tyr
1175                1180                1185

Gly Gly Phe Asp Ser Pro Thr Val Ala Tyr Ser Val Leu Val Val
1190                1195                1200

Ala Lys Val Glu Lys Gly Lys Ser Lys Lys Leu Lys Ser Val Lys
1205                1210                1215

Glu Leu Leu Gly Ile Thr Ile Met Glu Arg Ser Ser Phe Glu Lys
1220                1225                1230

Asn Pro Ile Asp Phe Leu Glu Ala Lys Gly Tyr Lys Glu Val Lys
1235                1240                1245

Lys Asp Leu Ile Ile Lys Leu Pro Lys Tyr Ser Leu Phe Glu Leu
1250                1255                1260

Glu Asn Gly Arg Lys Arg Met Leu Ala Ser Ala Gly Glu Leu Gln
1265                1270                1275

Lys Gly Asn Glu Leu Ala Leu Pro Ser Lys Tyr Val Asn Phe Leu
1280                1285                1290

Tyr Leu Ala Ser His Tyr Glu Lys Leu Lys Gly Ser Pro Glu Asp
1295                1300                1305

Asn Glu Gln Lys Gln Leu Phe Val Glu Gln His Lys His Tyr Leu
1310                1315                1320

Asp Glu Ile Ile Glu Gln Ile Ser Glu Phe Ser Lys Arg Val Ile
1325                1330                1335

Leu Ala Asp Ala Asn Leu Asp Lys Val Leu Ser Ala Tyr Asn Lys
1340                1345                1350

His Arg Asp Lys Pro Ile Arg Glu Gln Ala Glu Asn Ile Ile His
1355                1360                1365

Leu Phe Thr Leu Thr Asn Leu Gly Ala Pro Ala Ala Phe Lys Tyr
1370                1375                1380

Phe Asp Thr Thr Ile Asp Arg Lys Arg Tyr Thr Ser Thr Lys Glu
1385                1390                1395

Val Leu Asp Ala Thr Leu Ile His Gln Ser Ile Thr Gly Leu Tyr
1400                1405                1410

Glu Thr Arg Ile Asp Leu Ser Gln Leu Gly Gly Asp Lys Arg Pro
1415                1420                1425

Ala Ala Thr Lys Lys Ala Gly Gln Ala Lys Lys Lys Lys Gly Ser
1430                1435                1440

Gly Ser Asn Gly Ser Ser Gly Ser Ala Ser Lys Gly Glu Arg Leu
1445                1450                1455

Phe Arg Gly Lys Val Pro Ile Leu Val Glu Leu Lys Gly Asp Val
1460                1465                1470

Asn Gly His Lys Phe Ser Val Arg Gly Lys Gly Lys Gly Asp Ala
1475                1480                1485

Thr Arg Gly Lys Leu Thr Leu Lys Phe Ile Cys Thr Thr Gly Lys
1490                1495                1500

Leu Pro Val Pro Trp Pro Thr Leu Val Thr Thr Leu Thr Tyr Gly
1505                1510                1515

Val Gln Cys Phe Ser Arg Tyr Pro Lys His Met Lys Arg His Asp
1520                1525                1530

Phe Phe Lys Ser Ala Met Pro Lys Gly Tyr Val Gln Glu Arg Thr
1535                1540                1545

Ile Ser Phe Lys Lys Asp Gly Lys Tyr Lys Thr Arg Ala Glu Val
1550                1555                1560

Lys Phe Glu Gly Arg Thr Leu Val Asn Arg Ile Lys Leu Lys Gly
```

```
                1565                1570                1575
Arg Asp Phe Lys Glu Lys Gly Asn Ile Leu Gly His Lys Leu Arg
        1580                1585                1590

Tyr Asn Phe Asn Ser His Lys Val Tyr Ile Thr Ala Asp Lys Arg
        1595                1600                1605

Lys Asn Gly Ile Lys Ala Lys Phe Lys Ile Arg His Asn Val Lys
        1610                1615                1620

Asp Gly Ser Val Gln Leu Ala Asp His Tyr Gln Gln Asn Thr Pro
        1625                1630                1635

Ile Gly Arg Gly Pro Val Leu Leu Pro Arg Asn His Tyr Leu Ser
        1640                1645                1650

Thr Arg Ser Lys Leu Ser Lys Asp Pro Lys Glu Lys Arg Asp His
        1655                1660                1665

Met Val Leu Leu Glu Phe Val Thr Ala Ala Gly Ile Lys His Gly
        1670                1675                1680

Arg Asp Glu Arg Tyr Lys Gly Gly Ser Gly Gly Ser Val Asp Gly
        1685                1690                1695

Leu Phe Glu Ala Ile Glu Gly Phe Ile Glu Asn Gly Trp Glu Gly
        1700                1705                1710

Met Ile Asp Gly Trp Tyr Gly
        1715                1720

<210> SEQ ID NO 5
<211> LENGTH: 26
<212> TYPE: DNA
<213> ORGANISM: Artificial sequence
<220> FEATURE:
<223> OTHER INFORMATION: Synthetic construct

<400> SEQUENCE: 5
gctaattcac tcccaaagaa gacaag                                    26

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
cttcagcaag ccgagtcctg                                           20

<210> SEQ ID NO 7
<211> LENGTH: 60
<212> TYPE: DNA
<213> ORGANISM: Artificial sequence
<220> FEATURE:
<223> OTHER INFORMATION: Synthetic construct

<400> SEQUENCE: 7
gtcgacgtcg acgctcagtg aagctgaagt attccttctg cttcacaggg cgaccactac   60

<210> SEQ ID NO 8
<211> LENGTH: 49
<212> TYPE: DNA
<213> ORGANISM: Artificial sequence
<220> FEATURE:
<223> OTHER INFORMATION: Synthetic construct

<400> SEQUENCE: 8
atttaaatcc tccctcgaa cccttaccaa actcctatgc atactacag            49
```

<210> SEQ ID NO 9
<211> LENGTH: 60
<212> TYPE: DNA
<213> ORGANISM: Artificial sequence
<220> FEATURE:
<223> OTHER INFORMATION: Synthetic construct

<400> SEQUENCE: 9
ttaattaatt aattagcatt ttaggttcag gttgtgagaa cactagaaga gaacaagtca    60

<210> SEQ ID NO 10
<211> LENGTH: 52
<212> TYPE: DNA
<213> ORGANISM: Artificial sequence
<220> FEATURE:
<223> OTHER INFORMATION: Synthetic construct

<400> SEQUENCE: 10
gtatacgtat acgcatacct ggagagggga caaggtcttg agatgcgagg gt            52

<210> SEQ ID NO 11
<211> LENGTH: 52
<212> TYPE: DNA
<213> ORGANISM: Artificial sequence
<220> FEATURE:
<223> OTHER INFORMATION: Synthetic construct

<400> SEQUENCE: 11
agccacctta attaagccac catggcgcac gctgggagaa cggggtacga ta            52

<210> SEQ ID NO 12
<211> LENGTH: 60
<212> TYPE: DNA
<213> ORGANISM: Artificial sequence
<220> FEATURE:
<223> OTHER INFORMATION: Synthetic construct

<400> SEQUENCE: 12
taacagagag aagttcgtgg ctccggatcc cttgtggccc agataggcac ccagggtgat    60

<210> SEQ ID NO 13
<211> LENGTH: 24
<212> TYPE: DNA
<213> ORGANISM: Artificial sequence
<220> FEATURE:
<223> OTHER INFORMATION: Synthetic construct

<400> SEQUENCE: 13
caccgtgaga tacagataca gaca                                           24

<210> SEQ ID NO 14
<211> LENGTH: 24
<212> TYPE: DNA
<213> ORGANISM: ARtificial sequence
<220> FEATURE:
<223> OTHER INFORMATION: Synthetic construct

<400> SEQUENCE: 14
aaactgtctg tatctgtatc tcac                                           24

<210> SEQ ID NO 15
<211> LENGTH: 25
<212> TYPE: DNA
<213> ORGANISM: Artificial sequence
<220> FEATURE:

<223> OTHER INFORMATION: Synthetic construct

<400> SEQUENCE: 15
aaacggcatt ccaggcaaat cattc                                              25

<210> SEQ ID NO 16
<211> LENGTH: 25
<212> TYPE: DNA
<213> ORGANISM: Artificial sequence
<220> FEATURE:
<223> OTHER INFORMATION: Synthetic construct

<400> SEQUENCE: 16
caccgcagcc taggcaaagg cctgc                                              25

<210> SEQ ID NO 17
<211> LENGTH: 25
<212> TYPE: DNA
<213> ORGANISM: Artificial sequence
<220> FEATURE:
<223> OTHER INFORMATION: Synthetic construct

<400> SEQUENCE: 17
aaacgcaggc ctttgcctag gctgc                                              25

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
caccgtgcca acagaactgc ctgat                                              25

<210> SEQ ID NO 19
<211> LENGTH: 25
<212> TYPE: DNA
<213> ORGANISM: Artificial sequence
<220> FEATURE:
<223> OTHER INFORMATION: Synthetic construct

<400> SEQUENCE: 19
aaacatcagg cagttctgtt ggcac                                              25

<210> SEQ ID NO 20
<211> LENGTH: 24
<212> TYPE: DNA
<213> ORGANISM: Artificial sequence
<220> FEATURE:
<223> OTHER INFORMATION: Synthetic construct

<400> SEQUENCE: 20
caccgaccag ggtgcaagtg tgga                                               24

<210> SEQ ID NO 21
<211> LENGTH: 24
<212> TYPE: DNA
<213> ORGANISM: Artificial sequence
<220> FEATURE:
<223> OTHER INFORMATION: Synthetic construct

<400> SEQUENCE: 21
aaactccaca cttgcaccct ggtc                                               24

<210> SEQ ID NO 22
<211> LENGTH: 24
<212> TYPE: DNA
<213> ORGANISM: Artificial sequence
<220> FEATURE:
<223> OTHER INFORMATION: Synthetic construct

<400> SEQUENCE: 22
caccgctcct cagcctggca ttca                                              24

<210> SEQ ID NO 23
<211> LENGTH: 24
<212> TYPE: DNA
<213> ORGANISM: Artificial sequence
<220> FEATURE:
<223> OTHER INFORMATION: Synthetic construct

<400> SEQUENCE: 23
aaactgaatg ccaggctgag gagc                                              24

<210> SEQ ID NO 24
<211> LENGTH: 23
<212> TYPE: DNA
<213> ORGANISM: Artificial sequence
<220> FEATURE:
<223> OTHER INFORMATION: Synthetic construct

<400> SEQUENCE: 24
tgctaaagcg catgctccag act                                               23

<210> SEQ ID NO 25
<211> LENGTH: 21
<212> TYPE: DNA
<213> ORGANISM: Artificial sequence
<220> FEATURE:
<223> OTHER INFORMATION: Synthetic construct

<400> SEQUENCE: 25
gtcttcatct cagggtcggc t                                                 21

<210> SEQ ID NO 26
<211> LENGTH: 21
<212> TYPE: DNA
<213> ORGANISM: Artificial sequence
<220> FEATURE:
<223> OTHER INFORMATION: Synthetic construct

<400> SEQUENCE: 26
cctctctgtg cattatggca g                                                 21

<210> SEQ ID NO 27
<211> LENGTH: 19
<212> TYPE: DNA
<213> ORGANISM: Artificial sequence
<220> FEATURE:
<223> OTHER INFORMATION: Synthetic construct

<400> SEQUENCE: 27
gccttctatc gccttcttg                                                    19

<210> SEQ ID NO 28
<211> LENGTH: 20
<212> TYPE: DNA
<213> ORGANISM: Artificial sequence
<220> FEATURE:
<223> OTHER INFORMATION: Synthetic construct

<400> SEQUENCE: 28
actcctccac ctttgacgct                                            20

<210> SEQ ID NO 29
<211> LENGTH: 23
<212> TYPE: DNA
<213> ORGANISM: Artificial sequence
<220> FEATURE:
<223> OTHER INFORMATION: Synthetic construct

<400> SEQUENCE: 29
tcccctcttc aagggtctac atg                                        23

<210> SEQ ID NO 30
<211> LENGTH: 20
<212> TYPE: DNA
<213> ORGANISM: Artificial sequence
<220> FEATURE:
<223> OTHER INFORMATION: Synthetic construct

<400> SEQUENCE: 30
gtgcaaaatg gaagggtttc                                            20

<210> SEQ ID NO 31
<211> LENGTH: 20
<212> TYPE: DNA
<213> ORGANISM: Artificial sequence
<220> FEATURE:
<223> OTHER INFORMATION: Synthetic construct

<400> SEQUENCE: 31
ggagctccgt gaagttgttc                                            20

<210> SEQ ID NO 32
<211> LENGTH: 21
<212> TYPE: DNA
<213> ORGANISM: Artificial sequence
<220> FEATURE:
<223> OTHER INFORMATION: Synthetic construct

<400> SEQUENCE: 32
tgtttccttt cactggccac a                                          21

<210> SEQ ID NO 33
<211> LENGTH: 21
<212> TYPE: DNA
<213> ORGANISM: Artificial sequence
<220> FEATURE:
<223> OTHER INFORMATION: Synthetic construct

<400> SEQUENCE: 33
aacggcaact ggtgaacggt a                                          21

<210> SEQ ID NO 34
<211> LENGTH: 22
<212> TYPE: DNA
<213> ORGANISM: Artificial sequence
<220> FEATURE:
<223> OTHER INFORMATION: Synthetic construct

<400> SEQUENCE: 34
ggcgatgcca gaatagatgc cg                                         22

<210> SEQ ID NO 35
<211> LENGTH: 29

```
<212> TYPE: DNA
<213> ORGANISM: Artificial sequence
<220> FEATURE:
<223> OTHER INFORMATION: Synthetic construct

<400> SEQUENCE: 35
ccaggccact tggctcctct atctccaga                                      29

<210> SEQ ID NO 36
<211> LENGTH: 25
<212> TYPE: DNA
<213> ORGANISM: Artificial sequence
<220> FEATURE:
<223> OTHER INFORMATION: Synthetic construct

<400> SEQUENCE: 36
ccttactgtt gagactgcaa tatcc                                          25

<210> SEQ ID NO 37
<211> LENGTH: 26
<212> TYPE: DNA
<213> ORGANISM: Artificial sequence
<220> FEATURE:
<223> OTHER INFORMATION: Synthetic construct

<400> SEQUENCE: 37
ctgaagtccc agtatatact tcacac                                         26

<210> SEQ ID NO 38
<211> LENGTH: 25
<212> TYPE: DNA
<213> ORGANISM: Artificial sequence
<220> FEATURE:
<223> OTHER INFORMATION: Synthetic construct

<400> SEQUENCE: 38
cccagaagca gtaataatca tcgag                                          25

<210> SEQ ID NO 39
<211> LENGTH: 23
<212> TYPE: DNA
<213> ORGANISM: Artificial sequence
<220> FEATURE:
<223> OTHER INFORMATION: Synthetic construct

<400> SEQUENCE: 39
atgtgggatg tagtagatct tgc                                            23

<210> SEQ ID NO 40
<211> LENGTH: 21
<212> TYPE: DNA
<213> ORGANISM: Artificial sequence
<220> FEATURE:
<223> OTHER INFORMATION: Synthetic construct

<400> SEQUENCE: 40
gggtcttacc tcagcagtta c                                              21

<210> SEQ ID NO 41
<211> LENGTH: 20
<212> TYPE: DNA
<213> ORGANISM: Artificial sequence
<220> FEATURE:
<223> OTHER INFORMATION: synthetic construct

<400> SEQUENCE: 41
```
cctcacacag tgtgacgcag                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic construct

<400> SEQUENCE: 42
gactgagtac ctgaaccggc                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic construct

<400> SEQUENCE: 43
gggccaaact gagcagagtc                                                  20

<210> SEQ ID NO 44
<211> LENGTH: 20
<212> TYPE: DNA
<213> ORGANISM: Artificial sequence
<220> FEATURE:
<223> OTHER INFORMATION: Synthetic construct

<400> SEQUENCE: 44
aagaccaggg tggttgggac                                                  20

<210> SEQ ID NO 45
<211> LENGTH: 20
<212> TYPE: DNA
<213> ORGANISM: Artificial sequence
<220> FEATURE:
<223> OTHER INFORMATION: Synthetic construct

<400> SEQUENCE: 45
gtaagaaaaa tgcccacgtc                                                  20

<210> SEQ ID NO 46
<211> LENGTH: 20
<212> TYPE: DNA
<213> ORGANISM: Artificial sequence
<220> FEATURE:
<223> OTHER INFORMATION: Synthetic construct

<400> SEQUENCE: 46
agtcagacgt ctggagcttc                                                  20

<210> SEQ ID NO 47
<211> LENGTH: 22
<212> TYPE: DNA
<213> ORGANISM: Artificial sequence
<220> FEATURE:
<223> OTHER INFORMATION: Synthetic construct

<400> SEQUENCE: 47
gtgagcagtg aaggcatgag tc                                               22

<210> SEQ ID NO 48
<211> LENGTH: 20
<212> TYPE: DNA
<213> ORGANISM: Artificial sequence

```
<220> FEATURE:
<223> OTHER INFORMATION: Synthetic construct

<400> SEQUENCE: 48
gtgagataca gatacagaca                                                  20

<210> SEQ ID NO 49
<211> LENGTH: 20
<212> TYPE: DNA
<213> ORGANISM: Artificial sequence
<220> FEATURE:
<223> OTHER INFORMATION: Synthetic construct

<400> SEQUENCE: 49
aatgatttgc ctggaatgcc                                                  20

<210> SEQ ID NO 50
<211> LENGTH: 23
<212> TYPE: PRT
<213> ORGANISM: Artificial sequence
<220> FEATURE:
<223> OTHER INFORMATION: Synthetic construct

<400> SEQUENCE: 50

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 51
<211> LENGTH: 14
<212> TYPE: PRT
<213> ORGANISM: Artificial sequence
<220> FEATURE:
<223> OTHER INFORMATION: Synthetic construct

<400> SEQUENCE: 51

Tyr Gly Arg Lys Lys Arg Arg Gln Arg Arg Pro Pro Gln
1               5                   10

<210> SEQ ID NO 52
<211> LENGTH: 91
<212> TYPE: DNA
<213> ORGANISM: Artificial sequence
<220> FEATURE:
<223> OTHER INFORMATION: Synthetic construct

<400> SEQUENCE: 52
atccacgttc accttgcccc acagggcagt aacggcagac ttctcctcag gagtcaggtg      60
caccatggtg tctgtttgag gttgctagtg a                                     91

<210> SEQ ID NO 53
<211> LENGTH: 95
<212> TYPE: DNA
<213> ORGANISM: Artificial sequence
<220> FEATURE:
<223> OTHER INFORMATION: Synthetic construct

<400> SEQUENCE: 53
cttcatccac gttcaccttg ccccacaggg cagtaacggc agattttccc tcaggagtca      60
ggtgcaccat ggtgtctgtt tgaggttgct agtga                                 95

<210> SEQ ID NO 54
<211> LENGTH: 39
```

```
<212> TYPE: DNA
<213> ORGANISM: Artificial sequence
<220> FEATURE:
<223> OTHER INFORMATION: Synthetic construct

<400> SEQUENCE: 54
taatacgact cactataggg taacggcaga cttctccac                    39

<210> SEQ ID NO 55
<211> LENGTH: 21
<212> TYPE: DNA
<213> ORGANISM: Artificial sequence
<220> FEATURE:
<223> OTHER INFORMATION: Synthetic construct

<400> SEQUENCE: 55
aaaaagcacc gactcggtgc c                                      21

<210> SEQ ID NO 56
<211> LENGTH: 14
<212> TYPE: DNA
<213> ORGANISM: Artificial sequence
<220> FEATURE:
<223> OTHER INFORMATION: Synthetic construct

<400> SEQUENCE: 56
tcctgaggaa aaat                                              14

<210> SEQ ID NO 57
<211> LENGTH: 16
<212> TYPE: DNA
<213> ORGANISM: Artificial sequence
<220> FEATURE:
<223> OTHER INFORMATION: Synthetic construct

<400> SEQUENCE: 57
tgactcctga ggagaa                                            16

<210> SEQ ID NO 58
<211> LENGTH: 15
<212> TYPE: DNA
<213> ORGANISM: Artificial sequence
<220> FEATURE:
<223> OTHER INFORMATION: Synthetic construct

<400> SEQUENCE: 58
actcctgtgg agaag                                             15

<210> SEQ ID NO 59
<211> LENGTH: 25
<212> TYPE: DNA
<213> ORGANISM: Artificial sequence
<220> FEATURE:
<223> OTHER INFORMATION: Synthetic construct

<400> SEQUENCE: 59
cagagccatc tattgcttac atttg                                  25

<210> SEQ ID NO 60
<211> LENGTH: 20
<212> TYPE: DNA
<213> ORGANISM: Artificial sequence
<220> FEATURE:
<223> OTHER INFORMATION: Synthetic construct

<400> SEQUENCE: 60
```

```
ggcctcacca ccaacttcat                                                    20
```

<210> SEQ ID NO 61
<211> LENGTH: 60
<212> TYPE: PRT
<213> ORGANISM: Artificial sequence
<220> FEATURE:
<223> OTHER INFORMATION: Synthetic construct

<400> SEQUENCE: 61

```
Tyr Gly Arg Lys Lys Arg Arg Gln Arg Arg Pro Pro Gln Ala Gly
1               5                  10                  15

Gly Gly Ser Gly Gly Ser Tyr Gly Arg Lys Lys Arg Arg Gln Arg Arg
            20                  25                  30

Arg Pro Pro Gln Ala Gly Gly Gly Ser Gly Gly Ser Tyr Gly Arg Lys
        35                  40                  45

Lys Arg Arg Gln Arg Arg Arg Pro Pro Gln Ala Gly
    50                  55                  60
```

<210> SEQ ID NO 62
<211> LENGTH: 104
<212> TYPE: RNA
<213> ORGANISM: Artificial sequence
<220> FEATURE:
<223> OTHER INFORMATION: Synthetic construct

<400> SEQUENCE: 62

```
gggucugccg uuacugcccu gguuuuagag cuagaaauag caaguuaaaa uaaggcuagu        60
ccguuaucaa cuugaaaaag uggcaccgag ucggugcuuu uuuu                       104
```

<210> SEQ ID NO 63
<211> LENGTH: 105
<212> TYPE: RNA
<213> ORGANISM: Artificial sequence
<220> FEATURE:
<223> OTHER INFORMATION: Synthetic construct

<400> SEQUENCE: 63

```
ggguaacggc agacuucucc acguuuuaga gcuagaaaua gcaaguuaaa auaaggcuag        60
uccguuauca acuugaaaaa guggcaccga gucggugcuu uuuuu                      105
```

<210> SEQ ID NO 64
<211> LENGTH: 90
<212> TYPE: DNA
<213> ORGANISM: Artificial sequence
<220> FEATURE:
<223> OTHER INFORMATION: Synthetic construct

<400> SEQUENCE: 64

```
acctcaaaca gacaccatgg tgcacctgac tcctgaggag aagtctgccg tcacagctct        60
gtggggcaag gtgaacgtgg atgaagttgg                                         90
```

<210> SEQ ID NO 65
<211> LENGTH: 38
<212> TYPE: DNA
<213> ORGANISM: Artificial sequence
<220> FEATURE:
<223> OTHER INFORMATION: Synthetic construct

<400> SEQUENCE: 65

```
taatacgact cactataggg tctgccgtta ctgccctg                                38
```

```
<210> SEQ ID NO 66
<211> LENGTH: 20
<212> TYPE: DNA
<213> ORGANISM: Artificial sequence
<220> FEATURE:
<223> OTHER INFORMATION: Synthetic construct

<400> SEQUENCE: 66
tccacatgcc cagtttctat                                                   20

<210> SEQ ID NO 67
<211> LENGTH: 25
<212> TYPE: DNA
<213> ORGANISM: Artificial sequence
<220> FEATURE:
<223> OTHER INFORMATION: Synthetic construct

<400> SEQUENCE: 67
agtagcaatt tgtactgatg gtatg                                             25

<210> SEQ ID NO 68
<211> LENGTH: 20
<212> TYPE: DNA
<213> ORGANISM: Artificial sequence
<220> FEATURE:
<223> OTHER INFORMATION: Synthetic construct

<400> SEQUENCE: 68
ggtctgccgt tactgccctg                                                   20

<210> SEQ ID NO 69
<211> LENGTH: 20
<212> TYPE: DNA
<213> ORGANISM: Artificial sequence
<220> FEATURE:
<223> OTHER INFORMATION: Synthetic construct

<400> SEQUENCE: 69
gtaacggcag acttctccac                                                   20
```